US011396644B2

(12) United States Patent
Ko

(10) Patent No.: US 11,396,644 B2
(45) Date of Patent: Jul. 26, 2022

(54) METHOD FOR PROMOTING DIFFERENTIATION OF PLURIPOTENT STEM CELLS BY REDUCING UNDIFFERENTIATED STATE THEREOF

(71) Applicant: KEIO UNIVERSITY, Tokyo (JP)

(72) Inventor: Minoru Ko, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 477 days.

(21) Appl. No.: 16/072,610

(22) PCT Filed: Jan. 31, 2017

(86) PCT No.: PCT/JP2017/003325
§ 371 (c)(1),
(2) Date: Jul. 25, 2018

(87) PCT Pub. No.: WO2017/131238
PCT Pub. Date: Aug. 3, 2017

(65) Prior Publication Data

US 2019/0048320 A1 Feb. 14, 2019

(30) Foreign Application Priority Data

Jan. 31, 2016 (JP) ............................ JP2016-016785

(51) Int. Cl.

| | |
|---|---|
| ***C12N 5/077*** | (2010.01) |
| ***C12N 15/09*** | (2006.01) |
| ***C12N 5/0793*** | (2010.01) |
| ***C12N 5/071*** | (2010.01) |
| ***C12N 15/113*** | (2010.01) |

(52) U.S. Cl.
CPC ........... *C12N 5/0658* (2013.01); *C12N 5/067* (2013.01); *C12N 5/0619* (2013.01); *C12N 15/09* (2013.01); *C12N 15/113* (2013.01); *C12N 2310/14* (2013.01); *C12N 2506/02* (2013.01)

(58) Field of Classification Search
CPC .............. C12N 5/0658; C12N 2506/02; C12N 2501/60; C12N 5/0606
See application file for complete search history.

(56) References Cited

U.S. PATENT DOCUMENTS

2014/0370537 A1* 12/2014 Sakurai .............. G01N 33/5061 435/29

FOREIGN PATENT DOCUMENTS

JP 2004-236607 A 8/2004

OTHER PUBLICATIONS

Zhou, 2009 Cell Stem Cell, 4:381-384).*
Kodaka (2017, Stem Cells International, Article ID 1376151, pp. 1-16).*
Warren, 2010. Cell Stem Cell, 7:618-630.*
Takada (2005, Biochemical and Biophysical Research Communications 331(4):1039-1044).*
International Search Report issued in corresponding International Patent Application No. PCT/JP2017/003325 dated May 9, 2017 (6 pages).
Barberi et al., "Derivation of engraftable skeletal myoblasts from human embryonic stem cells," Nature Medicine, 2007, pp. 642-648, vol. 13, No. 5.
Bi et al., "Sox9 is required for cartilage formation," Nature Genetics, 1999, pp. 85-89, vol. 22.
Correa-Cerro et al., "Generation of mouse ES cell lines engineered for the forced induction of transcription factors," Scientific Reports, 2011, pp. 1-6, vol. 1, No. 167.
Darabi et al., "Human ES- and iPS-Derived Myogenic Progenitors Restore Dystrophin and Improve Contractility upon Transplantation in Dystrophic Mice," Cell Stem Cell, 2012, pp. 610-619, vol. 10, No. 5.
Fisher et al., "Normal Myeloid Development Requires Both the Glutamine-Rich Transactivation Domain and the PEST Region of Transcription Factor PU.1 but Not the Potent Acidic Transactivation Domain," Molecular and Cellular Biology, 1998, pp. 4347-4357, vol. 18, No. 7.
Goudenege et al., "Myoblasts Derived From Normal hESCs and Dystrophic hiPSCs Efficiently Fuse With Existing Muscle Fibers Following Transplantation," Molecular Therapy, 2012, pp. 2153-2167, vol. 20, No. 11.
Hamada et al., "Introduction of the MASH1 gene into mouse embryonic stem cells leads to differentiation of motoneuron precursors lacking Nogo receptor expression that can be applicable for transplantation to spinal cord injury," Neurobiology of Disease, 2006, pp. 509-522, vol. 22.
Ikeda et al., "Transplantation of motoneurons dervied from MASH 1-transfected mouse ES cells reconstitutes neural networks and improves motor function in hemiplegic mice," Experimental Neurology, 2004, pp. 280-292, vol. 189.

(Continued)

*Primary Examiner* — Valarie E Bertoglio
(74) *Attorney, Agent, or Firm* — Kilyk & Bowersox, P.L.L.C.

(57) ABSTRACT

In related-art methods of differentiating pluripotent stem cells into a desired cell type, there has not been established a differentiation induction method using human ES/iPS cells and being highly efficient. Many attempts have been made, including a stepwise differentiation induction method based on the control of culture conditions or the addition of, for example, various cell growth factors/differentiation factors to a culture solution, but the use of complicated culture steps is a big problem. A method of inducing differentiation into a desired cell type within a short period of time and with high efficiency by use of a pluripotent stem cell that actively undergoes cell differentiation, which is obtained by reducing an undifferentiated state of the pluripotent stem cell, has been developed, and thus the present invention has been completed.

2 Claims, 9 Drawing Sheets

Specification includes a Sequence Listing.

(56) References Cited

OTHER PUBLICATIONS

Ivanova et al., "Dissecting self-renewal in stem cells with RNA interference," Nature, 2006, pp. 533-538, vol. 442.
Lee et al., "Oct-4 controls cell-cycle progression of embryonic stem cells," Biochemical Journal, 2010, pp. 171-181, vol. 426, No. 2.
Liu et al., "Epigenetic silencing of HDAC1 by miR-449a upregulates Runx2 and promotes osteoblast differentiation," International Journal of Molecular Medicine, 2015, pp. 238-246, vol. 35, No. 1.
Livigni et al., "A Conserved Oct4/POUV-Dependent Network Links Adhesion and Migration to Progenitor Maintenance," Current Biology, 2013, pp. 2233-2244, vol. 23.
Nishiyama et al., "Uncovering Early Response of Gene Regulatory Networks in ESCs by Systematic Induction of Transcription Factors," Cell Stem Cell, 2009, pp. 420-433, vol. 5.
Niwa et al., "Quantitative expression of Oct-3/4 defines differentiation, dedifferentiation of self-renewal of ES cells," Nature Genetics, 2000, pp. 372-376, vol. 24, No. 4.
Sharov et al., "Identification of Pou5fl, Sox2, and Nanog downstream target genes with statistical confidence by applying a novel algorithm to time course microarray and genome-wide chromatin immunoprecipitation data," BMC Genomics, 2008, pp. 1-19, vol. 9, No. 269.
Sakurai, "Modeling muscular diseases using patient-derived iPS cells," Journal of Pharmaceutical Science, 2015, p. S37, vol. 128.
Tanaka et al., "Efficient and Reproducible Myogenic Differentiation from Human iPS Cells: Prospects for Modeling Miyoshi Myopathy In Vitro," PLOS One, 2013, pp. 1-14, vol. 8, Issue 4, e61540.
Tashiro et al., "Efficient Adipocyte and Osteoblast Differentiation from Mouse Induced Pluripotent Stem Cells by Adenoviral Transduction," Stem Cells, 2009, pp. 1802-1811, vol. 27, No. 8.
Yamamizu et al., "Identification of Transcription Factors for Lineage-Specific ESC Differentiation," Stem Cell Reports, 2013, pp. 1-15, vol. 1.
Ying et al., "Oct4 Coordinates with WNT Signaling to Pre-pattern Chromatin at the SOX17 Locus during Human ES Cell Differentiation into Definitive Endoderm," Stem Cell Reports, 2015, pp. 490-498, vol. 5, No. 4.
Takayama, "Establishment of a Method of Hepatocyte Differentiation from Human Pluripotent Stem Cells for Innovation Drug Development," Journal of the Pharmaceutical Society of Japan, 2015, pp. 1141-1146, vol. 135, No. 10 (machine translation of Abstract only attached).
Zhao et al., "Parallel Expression of Sox9 and Col2a1 in Cells Undergoing Chondrogenesis," Developmental Dynamics, 1997, pp. 377-386, vol. 209.
Cao, H3k27ME3 demethylases JMJD3 and/or UTX contribute to activating expression of endoderm and early lung development transcription factors FOXA2 and GATA6, American Journal of Respiratory and Critical Care Medicine, 2012, vol. 185, Supp. MeetingAbstracts, Abstract No. A3483 (abstract only).
Extended European Search Report issued in corresponding European Patent Application No. 17744467.6 dated Jul. 3, 2019 (8 pages).
Hough et al., "Differentiation of Mouse Embryonic Stem Cells after RNA Interference-Mediated Silencing of OCT4 and Nanog," XP-002791960, Stem Cells, 2006, vol. 24, pp. 1467-1475.
Zhang et al., "Oct4 Maintains the Pluripotency of Human Embryonic Stem Cells by Inactivating p53 Through Sirt1-Mediated Deacetylation," XP-002791961, Stem Cells, 2014, vol. 32, pp. 157-165.
Nishiyama et al., "Systematic repression of transcription factors reveals limited patterns of gene expression change in ES cells," XP-002791962, Scientific Reports, 2013, vol. 3, No. 1390, pp. 1-6.
Kushwaha et al., "Interrogation of a Context-Specific Transcription Factor Network Identifies Novel Regulators of Pluripotency," XP-002791963, Stem Cells, 2015, vol. 33, pp. 367-377.

* cited by examiner

METHOD FOR PROMOTING DIFFERENTIATION OF PLURIPOTENT STEM CELLS BY REDUCING UNDIFFERENTIATED STATE THEREOF

TECHNICAL FIELD

The present application claims priority from Japanese Patent Application No. 2016-016785, which is incorporated herein by reference.

The present invention relates to a method of reducing an undifferentiated state of a pluripotent stem cell, and more specifically, to a method of differentiating a pluripotent stem cell into a desired cell type with high efficiency and a differentiation induction kit to be used for the differentiation method.

BACKGROUND ART (On Induction of Differentiation of Pluripotent Stem Cells)

Regenerative medicine using cells obtained by inducing differentiation of pluripotent stem cells, such as embryonic stem cells (ES cells) or induced pluripotent stem cells (iPS cells) is a therapeutic method for which all peoples of the world have high expectations and which are desired to be realized soon. As regenerative medicine, a transplantation therapy with retinal pigment epithelial cells derived from iPS cells is fresh in our memory. However, a technology for rapidly generating mature differentiated cells suited for cell transplantation in a sufficient amount is still under development and has much room for development.

A current mainstream method of inducing differentiation of pluripotent stem cells into a desired cell type is a method involving sequentially adding cytokines/growth factors suited for respective differentiation stages to a medium to cause differentiation via an embryoid body and progenitor cells. This method has problems in, for example, that a culture period until differentiated cells of interest are obtained is long, that differentiation induction efficiency is not high, and that cells of different cell lineages are mixed with each other.

In recent years, attempts have been actively made to direct cell differentiation by forcibly expressing, in ES/iPS cells, one or a combination of a plurality of tissue-specifically expressed transcription factors. This differentiation induction method using transcription factors can directly induce ES/iPS cells into differentiated cells of interest, and hence is expected to be extremely effective means. However, even with this technique, differentiation induction efficiency for some cell types is still low, and thus, it is difficult to obtain a sufficient number of differentiated cells required for regenerative medicine.

In view of the foregoing, there has been a demand for development of a novel differentiation induction method for producing differentiated cells of interest from pluripotent stem cells more rapidly and more uniformly with higher efficiency.

(Current Situation of Induction of Differentiation of Pluripotent Stem Cells in Related Art)

Non Patent Literatures 1 to 4, which are related art, are each directed to a system for facilitating induction of differentiation of ES/iPS cells. For an example, there was a disclosure that ES/iPS cells were induced into skeletal muscle differentiation.

However, those differentiation induction methods are clearly different from a differentiation induction method of the present invention.

In Non Patent Literature 5, there was a disclosure that "in research using mouse ES cells, when expression of a transcription factor Oct3/4 is repressed, trophectoderm can be derived from the ES cells." In addition, in Patent Literature 1, there was a disclosure that "differentiation of neural stem cells into neurons, glial cells, and the like can be regulated by controlling an expression amount of an Oct-3/4 protein in the neural stem cells."

However, there was no disclosure or suggestion of a method of efficiently inducing differentiation into a desired cell type by introducing a transcription factor required for induction of differentiation into the desired cell type into a pluripotent stem cell.

CITATION LIST

Patent Literature

[PTL 1] JP 2004-236607 A

Non Patent Literature

[NPL 1] Nature medicine 13: 642-648.
[NPL 2] Cell stem cell 10: 610-619.
[NPL 3] Mol Ther. November; 20(11): 2153-67.
[NPL 4] PLoS One. 2013 Apr. 23; 8(4): e61540.
[NPL 5] Nat. Genet. 24(4): 372-6.

SUMMARY OF INVENTION

Technical Problem

In related-art methods of differentiating pluripotent stem cells into a desired cell type, there has not been established a differentiation induction method using human ES/iPS cells and being stable and highly efficient. Many attempts have been made, including a stepwise differentiation induction method based on the control of culture conditions or the addition of, for example, various cell growth factors/differentiation factors to a culture solution, but the use of complicated culture steps is a big problem. In addition, there are also big problems in, for example, that the speed of cell differentiation is low, and hence long-period culture is required, and that the differentiation efficiency is low, and hence it is difficult to obtain a sufficient number of required cells.

Solution to Problem

The inventors of the present invention have presumed that the above-mentioned problems are partly due to the fact that pluripotent stem cells have a property of maintaining the undifferentiated state of the cells by various mechanisms. In view of this, the inventors have developed a method of inducing differentiation into a desired cell type within a short period of time and with high efficiency by reducing undifferentiated state maintenance of a pluripotent stem cell to generate a pluripotent stem cell that actively proceeds to a differentiated cell type.

Further, the inventors have developed a method of more potently inducing differentiation into a desired cell type within a short period of time and with high efficiency by not only reducing undifferentiated state maintenance of a pluripotent stem cell but also reducing differentiation resistance thereof.

Thus, the present invention has been completed.

That is, the present invention includes the following.

1. A differentiation induction kit for differentiating a pluripotent stem cell into a desired cell type, including at least any one of the following items (1) to (8):

(1) a pluripotent stem cell and a gene for a compound having an action of substantially removing or reducing an expression amount of a POU5F1 protein;

(2) a pluripotent stem cell in which an expression amount of a POU5F1 protein has been substantially removed or reduced;

(3) a pluripotent stem cell in which a gene for a compound having an action of substantially removing or reducing an expression amount of a POU5F1 protein is forcibly expressed;

(4) a gene construct carrying a gene for a compound having an action of substantially removing or reducing an expression amount of a POU5F1 protein, and a pluripotent stem cell;

(5) a pluripotent stem cell having a gene construct carrying a gene for a compound having an action of substantially removing or reducing an expression amount of a POU5F1 protein inserted into a genome thereof;

(6) a pluripotent stem cell in which a POU5F1 gene has been disrupted;

(7) a pluripotent stem cell in which an expression amount of a POU5F1 protein has been substantially removed or reduced and which has a histone in which H3K27me3 modification has been substantially removed or reduced; and (8) a pluripotent stem cell, and a gene for a compound having an action of substantially removing or reducing an expression amount of a POU5F1 protein and a demethylase gene.

2. A differentiation induction kit according to the above-mentioned item 1, wherein the gene for the compound having an action of substantially removing or reducing an expression amount of a POU5F1 protein includes a gene expressing siRNA of POU5F1, a gene expressing shRNA of POU5F1, a gene expressing an antisense strand of POU5F1, and/or a gene for an antibody against POU5F1.

3. A differentiation induction kit according to the above-mentioned item 1 or 2, further including a transcription factor required for induction of differentiation into the desired cell type.

4. A differentiation induction kit according to the above-mentioned item 3, wherein a transcription factor gene for the transcription factor is carried on a Sendai virus vector.

5. A differentiation induction kit for differentiating a pluripotent stem cell into a skeletal muscle cell, including at least any one of the following items (1) to (8):

(1) a pluripotent stem cell in which an expression amount of a POU5F1 protein has been substantially removed or reduced, and a transcription factor MYOD1;

(2) a gene for a compound having an action of substantially removing or reducing an expression amount of a POU5F1 protein, a transcription factor MYOD1, and a pluripotent stem cell;

(3) a pluripotent stem cell in which a gene for a compound having an action of substantially removing or reducing an expression amount of a POU5F1 protein is forcibly expressed, and a transcription factor MYOD1;

(4) a gene construct carrying a gene for a compound having an action of substantially removing or reducing an expression amount of a POU5F1 protein, a transcription factor MYOD1, and a pluripotent stem cell;

(5) a pluripotent stem cell having a gene construct carrying a gene for a compound having an action of substantially removing or reducing an expression amount of a POU5F1 protein inserted into a genome thereof, and a transcription factor MYOD1;

(6) a pluripotent stem cell in which a POU5F1 gene has been disrupted, and a transcription factor MYOD1;

(7) a transcription factor MYOD1, and a pluripotent stem cell in which an expression amount of a POU5F1 protein has been substantially removed or reduced and which has a histone in which H3K27me3 modification has been substantially removed or reduced; and (8) a pluripotent stem cell, and a transcription factor MYOD1, a gene for a compound having an action of substantially removing or reducing an expression amount of a POU5F1 protein, and a demethylase gene.

6. A differentiation induction kit for differentiating a pluripotent stem cell into a neuron, including at least any one of the following items (1) to (8):

(1) a pluripotent stem cell in which an expression amount of a POU5F1 protein has been substantially removed or reduced, and transcription factors NEUROG1, NEUROG2, NEUROG3, NEUROD1, and NEUROD2;

(2) a gene for a compound having an action of substantially removing or reducing an expression amount of a POU5F1 protein, transcription factors NEUROG1, NEUROG2, NEUROG3, NEUROD1, and NEUROD2, and a pluripotent stem cell;

(3) a pluripotent stem cell in which a gene for a compound having an action of substantially removing or reducing an expression amount of a POU5F1 protein is forcibly expressed, and transcription factors NEUROG1, NEUROG2, NEUROG3, NEUROD1, and NEUROD2;

(4) a gene construct carrying a gene for a compound having an action of substantially removing or reducing an expression amount of a POU5F1 protein, transcription factors NEUROG1, NEUROG2, NEUROG3, NEUROD1, and NEUROD2, and a pluripotent stem cell;

(5) a pluripotent stem cell having a gene construct carrying a gene for a compound having an action of substantially removing or reducing an expression amount of a POU5F1 protein inserted into a genome thereof, and transcription factors NEUROG1, NEUROG2, NEUROG3, NEUROD1, and NEUROD2;

(6) a pluripotent stem cell in which a POU5F1 gene has been disrupted, and transcription factors NEUROG1, NEUROG2, NEUROG3, NEUROD1, and NEUROD2;

(7) transcription factors NEUROG1, NEUROG2, NEUROG3, NEUROD1, and NEUROD2, and a pluripotent stem cell in which an expression amount of a POU5F1 protein has been substantially removed or reduced and which has a histone in which H3K27me3 modification has been substantially removed or reduced; and (8) a pluripotent stem cell, and transcription factors NEUROG1, NEUROG2, NEUROG3, NEUROD1, and NEUROD2, a gene for a compound having an action of substantially removing or reducing an expression amount of a POU5F1 protein, and a demethylase gene.

7. A differentiation induction kit for differentiating a pluripotent stem cell into a hepatocyte, including at least any one of the following items (1) to (8):

(1) a pluripotent stem cell in which an expression amount of a POU5F1 protein has been substantially removed or reduced, and a transcription factor HNF1A;

(2) a gene for a compound having an action of substantially removing or reducing an expression amount of a POU5F1 protein, a transcription factor HNF1A, and a pluripotent stem cell;

(3) a pluripotent stem cell in which a gene for a compound having an action of substantially removing or reducing an expression amount of a POU5F1 protein is forcibly expressed, and a transcription factor HNF1A;

(4) a gene construct carrying a gene for a compound having an action of substantially removing or reducing an expression amount of a POU5F1 protein, a transcription factor HNF1A, and a pluripotent stem cell;

(5) a pluripotent stem cell having a gene construct carrying a gene for a compound having an action of substantially removing or reducing an expression amount of a POU5F1 protein inserted into a genome thereof, and a transcription factor HNF1A;

(6) a pluripotent stem cell in which a POU5F1 gene has been disrupted, and a transcription factor HNF1A;

(7) a transcription factor HNF1A, and a pluripotent stem cell in which an expression amount of a POU5F1 protein has been substantially removed or reduced and which has a histone in which H3K27me3 modification has been substantially removed or reduced; and (8) a pluripotent stem cell, a transcription factor HNF1A, a demethylase gene, and a gene for a compound having an action of substantially removing or reducing an expression amount of a POU5F1 protein.

8. A differentiation induction kit according to the above-mentioned item 3 or 4, wherein the differentiation induction kit is as described in any one of the following items (1) to (6):

(1) the transcription factor required for induction of differentiation into the desired cell type includes MYOD1, and the desired cell type includes a skeletal muscle cell;

(2) the transcription factor required for induction of differentiation into the desired cell type includes HNF1A, and the desired cell type includes a hepatocyte;

(3) the transcription factor required for induction of differentiation into the desired cell type includes SOX9, and the desired cell type includes a chondrocyte;

(4) the transcription factor required for induction of differentiation into the desired cell type includes RUNX2, and the desired cell type includes a bone cell;

(5) the transcription factor required for induction of differentiation into the desired cell type includes SPI1, and the desired cell type includes a hematopoietic cell; and (6) the transcription factor required for induction of differentiation into the desired cell type includes ASCL1, and the desired cell type includes a neuron.

9. A method of differentiating a pluripotent stem cell into a desired cell type, including any one of the following steps (1) to (9):

(1) a step of adding a gene for a compound having an action of substantially removing or reducing an expression amount of a POU5F1 protein, and a transcription factor required for induction of differentiation into the desired cell type to a pluripotent stem cell;

(2) a step of inserting a gene construct carrying a gene for a compound having an action of substantially removing or reducing an expression amount of a POU5F1 protein, and a transcription factor gene required for induction of differentiation into the desired cell type into a genome of a pluripotent stem cell;

(3) a step of inserting a gene construct carrying a gene for a compound having an action of substantially removing or reducing an expression amount of a POU5F1 protein, and a gene construct carrying a transcription factor required for induction of differentiation into the desired cell type into a genome of a pluripotent stem cell;

(4) a step of adding a transcription factor required for induction of differentiation into the desired cell type to a pluripotent stem cell, in which an expression amount of a POU5F1 protein has been substantially removed or reduced;

(5) a step of adding a transcription factor required for induction of differentiation into the desired cell type to a pluripotent stem cell, in which a compound having an action of substantially removing or reducing an expression amount of a POU5F1 protein is forcibly expressed;

(6) a step of adding a compound having an action of substantially removing or reducing an expression amount of a POU5F1 protein, and a transcription factor required for differentiation into the desired cell type to a pluripotent stem cell;

(7) a step of adding a transcription factor required for induction of differentiation into the desired cell type to a pluripotent stem cell, in which a POU5F1 gene has been disrupted;

(8) a step of adding a gene for a compound having an action of substantially removing or reducing an expression amount of a POU5F1 protein, a demethylase gene, and a transcription factor required for induction of differentiation into the desired cell type to a pluripotent stem cell; and (9) a step of adding a transcription factor required for induction of differentiation into the desired cell type to a pluripotent stem cell in which an expression amount of a POU5F1 protein has been substantially removed or reduced and which has a histone in which H3K27me3 modification has been substantially removed or reduced.

10. A differentiation method according to the above-mentioned item 9, wherein the gene for the compound having an action of substantially removing or reducing an expression amount of a POU5F1 protein includes a gene expressing siRNA of POU5F1, a gene expressing shRNA of POU5F1, a gene expressing an antisense strand of POU5F1, and/or a gene for an antibody against POU5F1.

11. A differentiation method according to the above-mentioned item 9 or 10, wherein a gene for the transcription factor is carried on a Sendai virus vector.

12. A method of differentiating a pluripotent stem cell into a skeletal muscle cell, including any one of the following steps (1) to (9):

(1) a step of adding a gene for a compound having an action of substantially removing or reducing an expression amount of a POU5F1 protein and a transcription factor MYOD1 to a pluripotent stem cell;

(2) a step of inserting a gene construct carrying a gene for a compound having an action of substantially removing or reducing an expression amount of a POU5F1 protein and a gene for a transcription factor MYOD1 into a genome of a pluripotent stem cell;

(3) a step of inserting a gene construct carrying a gene for a compound having an action of substantially removing or reducing an expression amount of a POU5F1 protein and a gene construct carrying a transcription factor MYOD1 into a genome of a pluripotent stem cell;

(4) a step of adding a transcription factor MYOD1 to a pluripotent stem cell in which an expression amount of a POU5F1 protein has been substantially removed or reduced;

(5) a step of adding a transcription factor MYOD1 to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and a transcription factor MYOD1 to a pluripotent stem cell;

(7) a step of adding a transcription factor MYOD1 to a pluripotent stem cell in which a POU5F1 gene has been disrupted;

(8) a step of adding a gene for a compound having an action of substantially removing or reducing an expression amount of a POU5F1 protein, a demethylase gene, and a transcription factor MYOD1 to a pluripotent stem cell; and (9) a step of adding a transcription factor MYOD1 to a pluripotent stem cell in which an expression amount of a POU5F1 protein has been substantially removed or reduced and which has a histone in which H3K27me3 modification has been substantially removed or reduced.

13. A method of differentiating a pluripotent stem cell into a neuron, including any one of the following steps (1) to (9):

(1) a step of adding a gene for a compound having an action of substantially removing or reducing an expression amount of a POU5F1 protein and transcription factors NEUROG1, NEUROG2, NEUROG3, NEUROD1, and/or NEUROD2 to a pluripotent stem cell;

(2) a step of inserting a gene construct carrying a gene for a compound having an action of substantially removing or reducing an expression amount of a POU5F1 protein and genes for transcription factors NEUROG1, NEUROG2, NEUROG3, NEUROD1, and/or NEUROD2 into a genome of a pluripotent stem cell;

(3) a step of inserting a gene construct carrying a gene for a compound having an action of substantially removing or reducing an expression amount of a POU5F1 protein and a gene construct carrying transcription factors NEUROG1, NEUROG2, NEUROG3, NEUROD1, and/or NEUROD2 into a genome of a pluripotent stem cell;

(4) a step of adding transcription factors NEUROG1, NEUROG2, NEUROG3, NEUROD1, and/or NEUROD2 to a pluripotent stem cell in which an expression amount of a POU5F1 protein has been substantially removed or reduced;

(5) a step of adding transcription factors NEUROG1, NEUROG2, NEUROG3, NEUROD1, and/or NEUROD2 to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and transcription factors NEUROG1, NEUROG2, NEUROG3, NEUROD1, and/or NEUROD2 to a pluripotent stem cell;

(7) a step of adding transcription factors NEUROG1, NEUROG2, NEUROG3, NEUROD1, and/or NEUROD2 to a pluripotent stem cell in which a POU5F1 gene has been disrupted;

(8) a step of adding a gene for a compound having an action of substantially removing or reducing an expression amount of a POU5F1 protein, a demethylase gene, and transcription factors NEUROG1, NEUROG2, NEUROG3, NEUROD1, and/or NEUROD2 to a pluripotent stem cell; and (9) a step of adding transcription factors NEUROG1, NEUROG2, NEUROG3, NEUROD1, and/or NEUROD2 to a pluripotent stem cell in which an expression amount of a POU5F1 protein has been substantially removed or reduced and which has a histone in which H3K27me3 modification has been substantially removed or reduced.

14. A method of differentiating a pluripotent stem cell into a hepatocyte, including any one of the following steps (1) to (9):

(1) a step of adding a gene for a compound having an action of substantially removing or reducing an expression amount of a POU5F1 protein and a transcription factor HNF1A to a pluripotent stem cell;

(2) a step of inserting a gene construct carrying a gene for a compound having an action of substantially removing or reducing an expression amount of a POU5F1 protein and a gene for a transcription factor HNF1A into a genome of a pluripotent stem cell;

(3) a step of inserting a gene construct carrying a gene for a compound having an action of substantially removing or reducing an expression amount of a POU5F1 protein and a gene construct carrying a transcription factor HNF1A into a genome of a pluripotent stem cell;

(4) a step of adding a transcription factor HNF1A to a pluripotent stem cell in which an expression amount of a POU5F1 protein has been substantially removed or reduced;

(5) a step of adding a transcription factor HNF1A to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and a transcription factor HNF1A to a pluripotent stem cell;

(7) a step of adding a transcription factor HNF1A to a pluripotent stem cell in which a POU5F1 gene has been disrupted;

(8) a step of adding a gene for a compound having an action of substantially removing or reducing an expression amount of a POU5F1 protein, a demethylase gene, and a transcription factor HNF1A to a pluripotent stem cell; and (9) a step of adding a transcription factor HNF1A to a pluripotent stem cell in which an expression amount of a POU5F1 protein has been substantially removed or reduced and which has a histone in which H3K27me3 modification has been substantially removed or reduced.

15. A differentiation method according to any one of the above-mentioned items 9 to 11, wherein the differentiation method is as described in any one of the following items (1) to (6):

(1) the transcription factor required for induction of differentiation into the desired cell type includes MYOD1, and the desired cell type includes a skeletal muscle cell;

(2) the transcription factor required for induction of differentiation into the desired cell type includes HNF1A, and the desired cell type includes a hepatocyte;

(3) the transcription factor required for induction of differentiation into the desired cell type includes SOX9, and the desired cell type includes a chondrocyte;

(4) the transcription factor required for induction of differentiation into the desired cell type includes RUNX2, and the desired cell type includes a bone cell;

(5) the transcription factor required for induction of differentiation into the desired cell type includes SPI1, and the desired cell type includes a hematopoietic cell; and (6) the transcription factor required for induction of differentiation into the desired cell type includes ASCL1, and the desired cell type includes a neuron.

Advantageous Effects of Invention

The method of differentiating a pluripotent stem cell into a desired cell type with high efficiency and differentiation induction kit for differentiating a pluripotent stem cell into a desired cell type with high efficiency of the present invention each have at least any one or more of the following effects.

(1) The period of time required for cell differentiation starting with the pluripotent stem cell is shortened and the differentiation induction efficiency is improved.

(2) As modified synthetic mRNA for a gene is used to introduce the gene into the pluripotent stem cell, the introduced gene is not incorporated into the genome of the pluripotent stem cell, and the result is that there is no risk of cancellation or the like after cell differentiation induction.

(3) In the introduction of the gene into the pluripotent stem cell using the modified synthetic mRNA, the timing and number of times of the addition of the mRNA for the gene can be easily changed, and hence optimal conditions specific to each of cell types can be selected.

(4) A method of reducing undifferentiated state maintenance of a pluripotent stem cell and a method of reducing differentiation resistance thereof are combined with each other to shorten the period of time required for cell differentiation starting with the pluripotent stem cell and improve the differentiation induction efficiency in a synergistic manner.

DESCRIPTION OF EMBODIMENTS

A method of reducing an undifferentiated state of a pluripotent stem cell of the present invention (hereinafter sometimes referred to as "method of the present invention") is described below, though the method is not particularly limited as long as the method is a method capable of reducing undifferentiated state maintenance of a pluripotent stem cell, and further, is a method capable of not only reducing undifferentiated state maintenance of a pluripotent stem cell but also reducing differentiation resistance thereof as required.

(Pluripotent Stem Cell)

The pluripotent stem cell to be used in the method of the present invention is not particularly limited, but is preferably derived from a mammal, particularly preferably derived from a human. The pluripotent stem cell is, for example, a human ES cell, a human iPS cell, or any combination thereof, is not particularly limited, and encompasses tissue stem cells derived from tissues and organs, dermal fibroblasts, and all kinds of cells derived from tissues or organs.

(Reducing Undifferentiated State Maintenance of Pluripotent Stem Cell)

Figure 1:
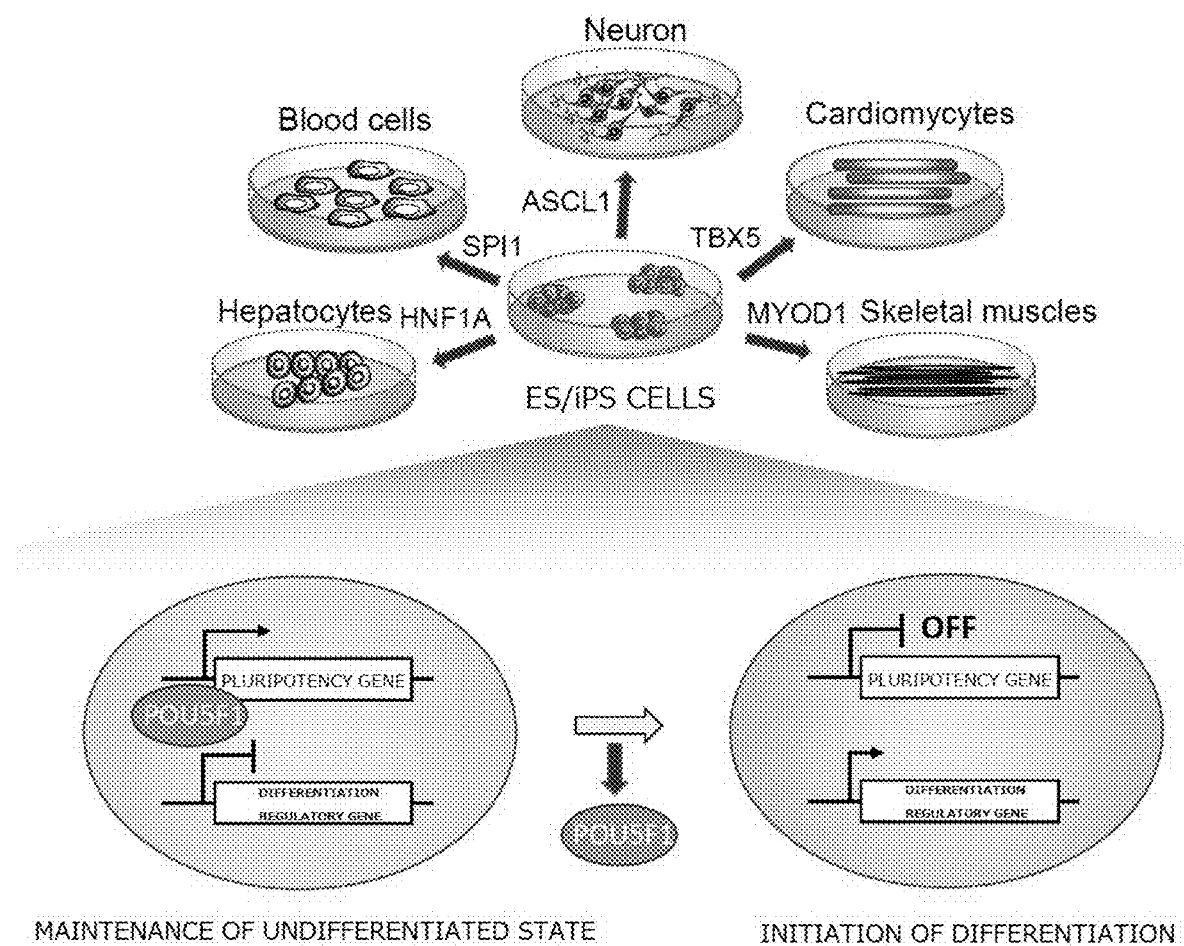
FIG. 1 A schematic diagram of a method of inducing differentiation of a pluripotent stem cell in which an expression amount of a POU5F1 protein has been reduced of the present invention. It is illustrated that differentiation into desired cells can be induced by introducing (adding) modified synthetic RNAs for tissue-specific transcription factors to pluripotent stem cells in which the function of POU5F1, a gene responsible for an undifferentiated state, has been suppressed by an RNA interference method.
Figure 2A:
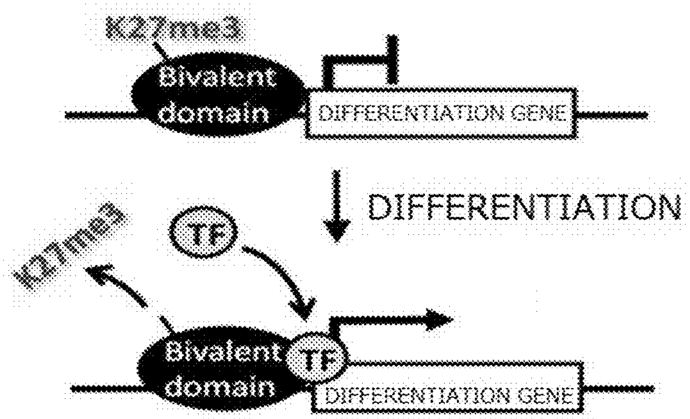
FIG. 2A A schematic diagram of a method of reducing differentiation resistance of a pluripotent stem cell to a desired cell type of the present invention.
Figure 2B:
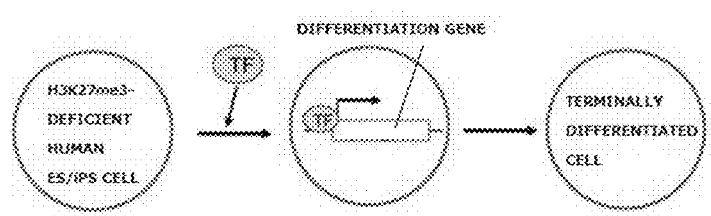
FIG. 2B When H3K27me3 modification in a human ES or iPS cell is reduced or removed, a transcription factor (TF) binds to the promoter site of a downstream gene to enhance the expression of a group of development/differentiation-related genes, resulting in differentiation.
Figure 2C:
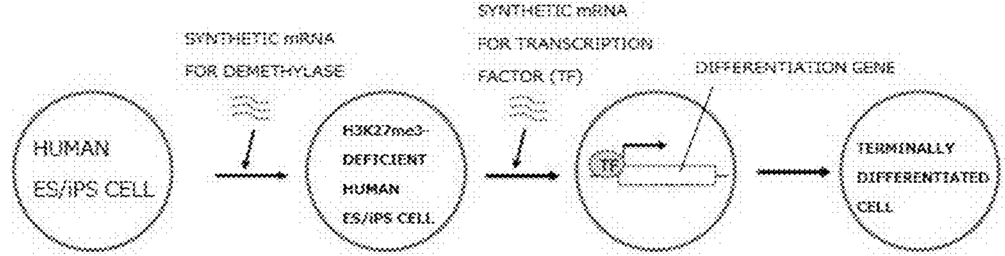
FIG. 2C A method of inducing differentiation of a human ES cell or iPS cell by introducing modified synthetic mRNA for a demethylase, and then introducing modified synthetic mRNA for the transcription factor (TF).
Figure 2D:
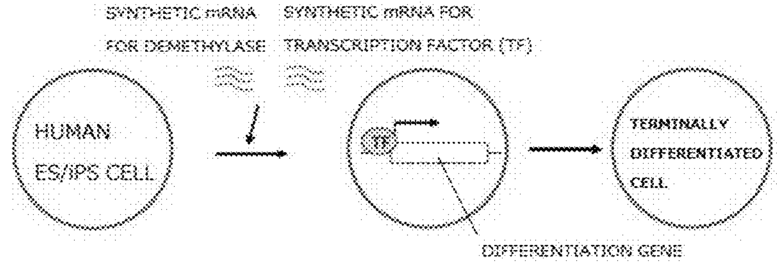
FIG. 2D A method of inducing differentiation of a human ES cell or iPS cell by simultaneously introducing the modified synthetic mRNAs for the demethylase and the transcription factor (TF).

In pluripotent stem cells, the expression of a transcription factor POU5F1 (SEQ ID NOS: 1 and 2: POU domain, class 5, transcription factor 1 isoform 1: http://www.ncbi.nlm.nih.gov/protein/NP_002692, other names: OCT3, OCT4, OTF3, OTF4, OTF-3, Oct-3, Oct-4, MGC22487) is essential to the undifferentiated state maintenance of the pluripotent stem cells. POU5F1 is specifically expressed in pluripotent cells, such as reproductive cells and a preimplantation early embryo. In Examples of the present invention, it has been confirmed that differentiation into a desired cell type can be efficiently induced by introducing a transcription factor required for induction of differentiation into the desired cell type into a pluripotent stem cell in which an expression amount of a POU5F1 protein has been reduced (see FIG. 1). That is, the "reducing undifferentiated state maintenance of a pluripotent stem cell" of the present invention means substantially removing or reducing an expression amount of a POU5F1 protein in the pluripotent stem cell. The substantially removing or reducing an expression amount of a POU5F1 protein encompasses inhibiting the process of any one of the transcription and translation stages of POU5F1 and/or inhibiting the activity of the translated POU5F1 protein, and is not particularly limited.

In addition, a state in which the expression amount of the POU5F1 protein in the pluripotent stem cell has been substantially removed or reduced may be confirmed by a comparison to the degree of the expression amount of the POU5F1 protein (or expression amount of the POU5F1 gene) in a pluripotent stem cell that has not been subjected to the removing or the reducing. For example, the state (degree) in which the expression amount of the POU5F1 protein in the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 15, from 30 to 20, or about 25 when compared to the expression amount of the POU5F1 protein in the pluripotent stem cell that has not been removed or reduced, which is defined as 100. The degree of the expression amount of the POU5F1 protein in the pluripotent stem cell may be easily measured by using a commercially available anti-POU5F1 antibody, and the gene expression amount of POU5F1 may be measured by a method known per se.

(Reducing Differentiation Resistance of Pluripotent Stem Cell to Desired Cell Type)

In pluripotent stem cells, a special chromatin structure called a "bivalent domain" is formed in each promoter region of a group of genes involved in differentiation, and under a stemness-maintaining state, the group of genes involved in development/differentiation are in a standby state so as not to be easily expressed. The inventors of the present invention have confirmed that "as a methyl group modification of a histone called H3K27me3 is removed or reduced in the "bivalent domain", the expression of differentiation genes required for induction of differentiation into the desired cell type is rapidly and efficiently facilitated" (see FIGS. 2A-2D).

Namely, the "reducing differentiation resistance of a pluripotent stem cell to a desired cell type" of the present invention means that the H3K27me3 modification of the pluripotent stem cell is substantially removed or reduced.

In addition, a state in which the H3K27me3 modification of the pluripotent stem cell has been substantially removed or reduced may be confirmed by a comparison to the degree of the H3K27me3 modification of a pluripotent stem cell that has not been subjected to the removing or the reducing. For example, the state (degree) in which the H3K27me3 modification of the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 20, or about 30 when compared to the degree of the H3K27me3 modification of the pluripotent stem cell that has not been removed or reduced, which is defined as 100. The degree of the H3K27me3 modification of the pluripotent stem cell may be easily measured by using a commercially available anti-Histone H3K27me3 antibody, and the gene expression amount of H3K27me3 may be measured by a method known per se.

(Method of Inducing Differentiation of Pluripotent Stem Cell into Desired Cell Type with High Efficiency of the Present Invention)

As described above, the method of the present invention is not particularly limited as long as the method is a method of reducing undifferentiated state maintenance of a pluripotent stem cell, and further, is a method capable of reducing differentiation resistance of a pluripotent stem cell to the desired cell type as required, and may be exemplified by the following.

(Use of Modified Synthetic mRNA for Target Gene)

The method of the present invention includes adding (introducing, transfecting), to a pluripotent stem cell, a gene for a compound having an action of substantially removing or reducing an expression amount of a POU5F1 protein (gene expressing small interfering RNA (siRNA) against POU5F1, gene expressing shRNA against POU5F1, gene expressing an antisense strand of POU5F1, or antibody gene), and further, a gene for a transcription factor required for induction of differentiation into the desired cell type.

Similarly, the method of the present invention includes adding (introducing, transfecting), to a pluripotent stem cell, a gene for a compound having an action of substantially removing or reducing H3K27me3 modification as required, and further, a gene for a transcription factor required for induction of differentiation of the pluripotent stem cell into the desired cell type.

The term "gene" as used herein encompasses not only double-stranded nucleic acids, but also their respective constituent single strands, such as plus strands (or sense strands) or complementary strands (or antisense strands), linear nucleic acids, and circular nucleic acids, and encompasses DNA, RNA, mRNA, cDNA, and the like, unless otherwise stated.

In addition, the term "target gene" is meant to encompass both of: the gene for the compound having an action of substantially removing or reducing an expression amount of a POU5F1 protein and/or the gene for the compound having an action of substantially removing or reducing H3K27me3 modification; and the transcription factor required for induction of differentiation into the desired cell type.

Figure 3:
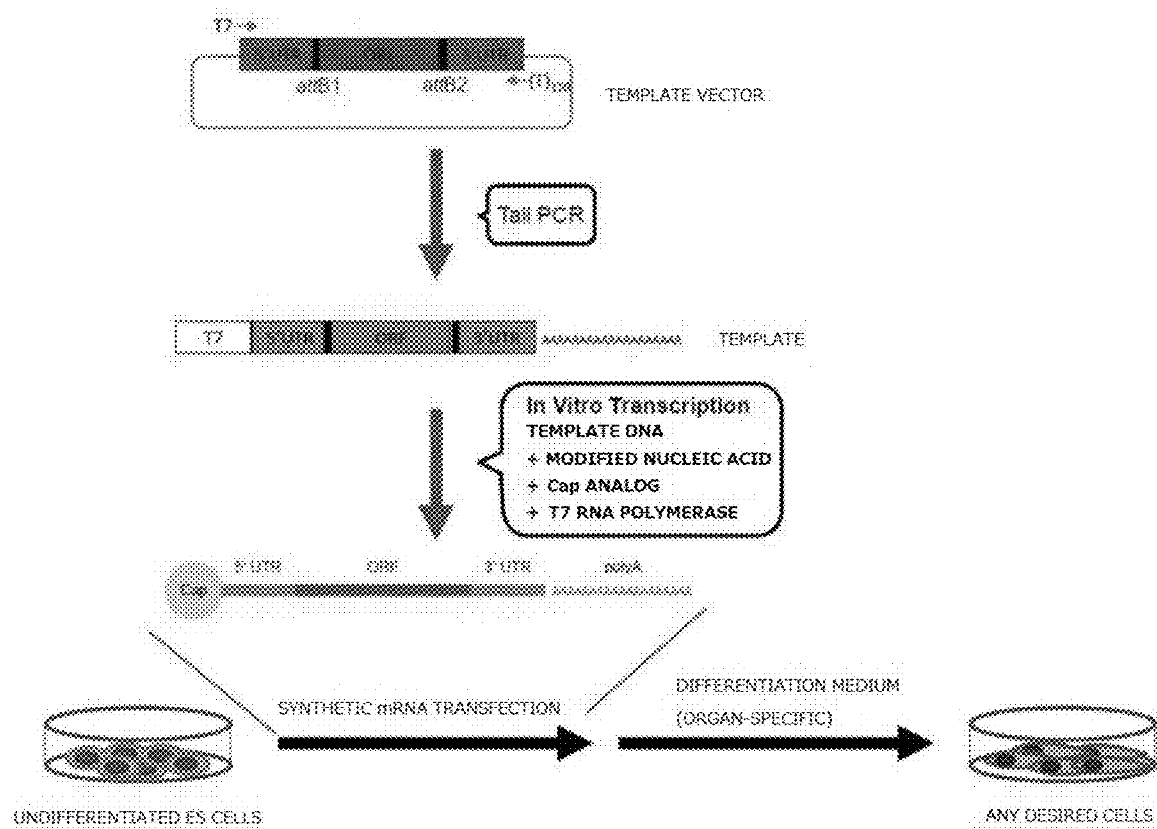
FIG. 3 A schematic view of a differentiation induction method using modified synthetic mRNA for a target gene.

In a step of the method of the present invention, a method known per se may be used without any particular limitation as a method of adding (introducing), to the pluripotent stem cell, the gene for the compound having an action of substantially removing or reducing an expression amount of a POU5F1 protein (or the gene for the compound having an action of substantially removing or reducing H3K27me3 modification) and/or the transcription factor required for induction of differentiation into the desired cell type. There is preferably used a method of inducing differentiation by efficiently introducing synthetic mRNA for a transcription factor into human pluripotent stem cells through use of a gene expression method involving using synthetic mRNA developed by Warren, Rossi, et al. (reference: Cell Stem Cell 7: 618-630, 2010), which is a footprint-free forced gene expression method causing no gene incorporation into a host genome (see FIG. 3).

The timing at which the gene for the compound having an action of substantially removing or reducing an expression amount of a POU5F1 protein (or the gene for the compound having an action of substantially removing or reducing H3K27me3 modification) and the transcription factor required for induction of differentiation into the desired cell type are added to the pluripotent stem cell is not particularly limited, but it is preferred that the gene for the compound having an action of substantially removing or reducing an expression amount of a POU5F1 protein (or the gene for the compound having an action of substantially removing or reducing H3K27me3 modification) be added to the pluripotent stem cell before the addition of the transcription factor required for differentiation induction.

Further, with regard to the addition timing of each gene (mRNA), the addition may be performed, for example, one or more times, preferably two to five times, two to four times, two or three times, or two times every 12 hours to 64 hours, but the addition timing is not particularly limited thereto. A more specific method may be exemplified by the following.

(Synthesis of Modified mRNA Encoding Amino Acid Sequence of Transcription Factor)

Modified mRNA is synthesized with a referred method described in the literature "Warren et al., Cell Stem Cell, 2010 Nov. 5; 7(5): 618-30." More specifically, mRNA is synthesized by in vitro transcription using a mixture of dNTPs {(dNTPs: 3-0-Me-m$^7$G(5')ppp(5')G ARCA cap analog, 5-methylcytidine triphosphate, and pseudouridine triphosphate)} obtained by modifying template DNA encoding the amino acid sequence of the transcription factor required for induction of differentiation into the desired cell type.

(Generation of Sendai Virus Vector Encoding Amino Acid Sequence of Transcription Factor)

In order to express a mammalian (in particular, human) transcription factor, a Sendai virus vector capable of expressing a human transcription factor is preferably used. In particular, a mutant of a Sendai virus vector, such as an F protein-deficient mutant, has no infectivity, and is easy to handle (see Inoue et al., J Virol. 77: 23238-3246, 2003).

(Method of Inducing Differentiation of Pluripotent Stem Cell into Desired Cell Type with High Efficiency)

A single transcription factor or a cocktail of two or more transcription factors required for induction of differentiation into the desired cell type is prepared. The form of the transcription factors is not particularly limited, and may be any of synthetic mRNAs, a Sendai virus vector having incorporated therein a transcription factor (or a plurality of transcription factors), and nanoparticle capsules containing synthetic mRNAs.

Figure 4:
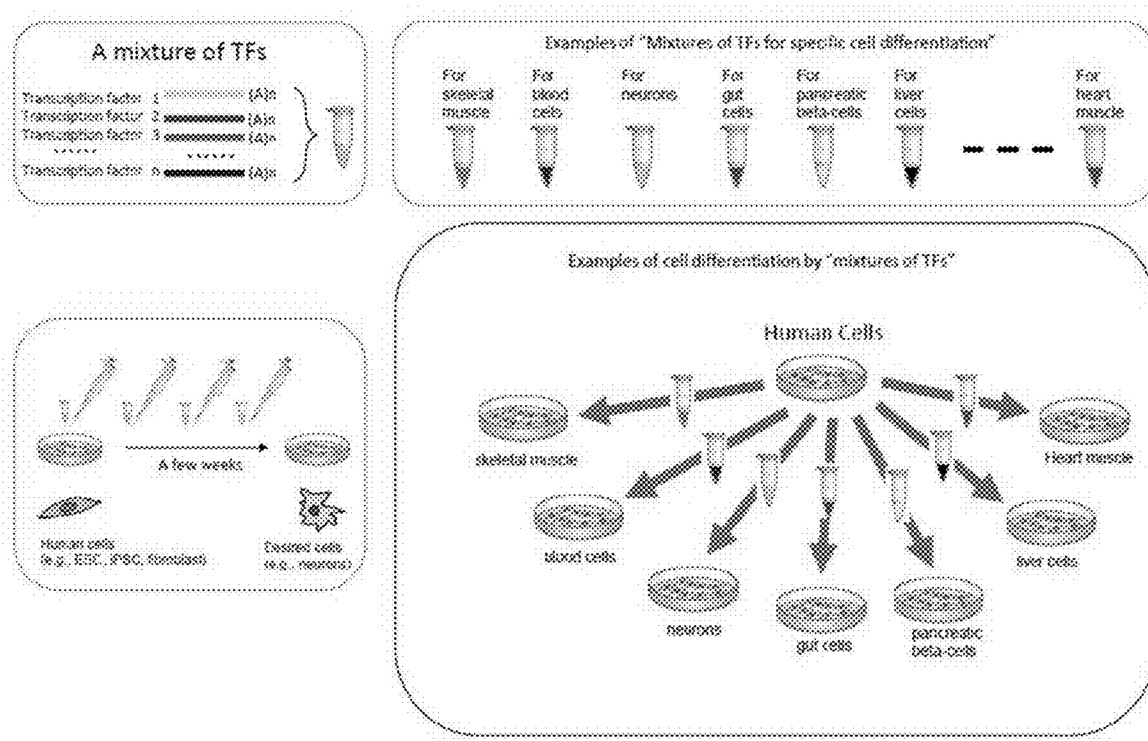
FIG. 4 A schematic view of a differentiation step using modified synthetic mRNA for a target gene.

A method of introducing the single transcription factor or cocktail of two or more transcription factors described above into cells is not particularly limited, and transfection with Lipofectamine, viral infection, or the like is utilized. A schematic view of one example of the differentiation induction step that may be utilized in the method of the present invention is illustrated in FIG. 4.

(Use of Expression Vector)

In a step of the method of the present invention, an expression vector known per se having introduced therein the gene for the compound having an action of substantially removing or reducing an expression amount of a POU5F1 protein (or the gene for the compound having an action of substantially removing or reducing H3K27me3 modification) and/or the transcription factor required for induction of differentiation into the desired cell type may be used. Examples of the expression vector to be used in the present invention may include, but not particularly limited to, an animal cell expression plasmid vector, a Sendai virus vector and others.

A method of introducing the synthetic mRNA and the expression vector into the pluripotent stem cell is not particularly limited, but examples thereof may include a lipofection method, a liposome method, an electroporation method, a calcium phosphate coprecipitation method, a diethylaminoethyl (DEAE)-dextran method, a microinjection method, a gene gun method and others. A particularly preferred example is a lipofection method.

Another method may involve using an expression vector for the gene for the compound having an action of substantially removing or reducing an expression amount of a POU5F1 protein (or the gene for the compound having an action of substantially removing or reducing H3K27me3 modification), and using synthetic mRNA for the transcription factor required for induction of differentiation into the desired cell type, or may adopt the opposite pattern.

(Compound Having Action of Substantially Removing or Reducing Expression Amount of POU5F1 Protein)

The compound having an action of substantially removing or reducing an expression amount of a POU5F1 protein of the present invention is not particularly limited, but is, for example, siRNA against POU5F1, shRNA against POU5F1, an antisense strand of POU5F1, an antibody that specifically binds to the POU5F1 protein, or an inhibitor.

In addition, not only by using those compounds alone, but also by using a plurality of kinds of compounds and/or a low-molecular-weight compound in combination, it is possible to efficiently "reduce an undifferentiated state of a pluripotent stem cell (substantially remove or reduce an expression amount of a POU5F1 protein in a pluripotent stem cell)."

(Compound Having Action of Substantially Removing or Reducing H3K27Me3 Modification)

The compound having an action of substantially removing or reducing H3K27me3 modification of the present invention is not particularly limited, but is, for example, a demethylase (in particular, a demethylase having an action of removing a methyl group of H3K27me3), an antibody that specifically binds to H3K27me3, an antibody for Polycomb-group proteins (PcG proteins) having an H3K27me3 modification action, siRNA (in particular, cationic siRNA), or an inhibitor. The cationic siRNA does not require a reagent for transfection.

Examples of the low-molecular-weight compound may include, but not particularly limited to, histone deacetylase (HDAC) inhibitors, such as valproic acid.

Examples of the demethylase include AOF (LSD1), AOF1 (LSD2), FBXL11 (JHDM1A), Fbxl10 (JHDM1B), FBXL19 (JHDM1C), KIAA1718 (JHDM1D), PHF2 (JHDM1E), PHF8 (JHDM1F), JMJD1A (JHDM2A), JMJD1B (JHDM2B), JMJD1C (JHDM2C), JMJD2A (JHDM3A), JMJD2B (JHDM3B), JMJD2C (JHDM3C), JMJD2D (JHDM3D), RBP2 (JARID1A), PLU1 (JARID1B), SMCX (JARID1C), SMCY (JARID1D), Jumonji (JARID2), UTX (UTX), UTY (UTY), JMJD3 (JMJD3), JMJD4 (JMJD4), JMJD5 (JMJD5), JMJD6 (JMJD6), JMJD7 (JMJD7), and JMJD8 (JMJD8). Of those, JMJD3, UTX, or the like is preferred as a demethylase having an action of removing a methyl group of H3K27me3.

In addition, the demethylase of the present invention also includes the following:

(1) a protected derivative, sugar chain-modified derivative, acylated derivative, or acetylated derivative of any one of the demethylases described above;

(2) an enzyme that has 90% (or 92%, 94%, 96%, 98%, or 99%) or more homology to any one of the demethylases described above and has a substantially equivalent action of substantially removing or reducing H3K27me3 modification to that of the demethylase; and (3) an enzyme that has 100 to 10, 50 to 30, 40 to 20, 10 to 5, or 5 to 1 amino acid substituted, deleted, inserted, and/or added in any one of the demethylases described above and has a substantially equivalent action of substantially removing or reducing H3K27me3 modification to that of the demethylase.

Further, the gene of the demethylase of the present invention includes the following:

(1) a gene encoding a polypeptide formed of the amino acid sequence of any one or more of the enzymes described above;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence of any one or more of the enzymes described above and has a substantially equivalent action of substantially removing or reducing H3K27me3 modification to that of the demethylase; and (3) a gene encoding a polypeptide that has 90% (or 92%, 94%, 96%, 98%, or 99%) or more homology to the amino acid sequence of any one or more of the enzymes described above and has a substantially equivalent action of substantially removing or reducing H3K27me3 modification to that of the demethylase.

An enzyme having a mutation may be a naturally occurring one, or may be one obtained by introducing a mutation on the basis of a gene of natural origin. Means for introducing a mutation is known per se, and for example, a site-directed mutagenesis method, a homologous gene recombination method, a primer extension method, a polymerase chain reaction (hereinafter abbreviated as PCR), and the like may be used alone or in combination thereof as appropriate.

The method may be performed in conformity with any of methods described in the literatures ("Molecular Cloning: A Laboratory Manual, second edition" edited by Sambrook et al., 1989, Cold Spring Harbor Laboratory; and "Lab Manual: Genetic Engineering" edited by Masami Muramatsu, 1988, Maruzen), or by modifying these methods, and Ulmer's technology (Ulmer, K. M., "Science", 1983, volume 219, p. 666-671) may also be utilized. In the case of a peptide, from the viewpoint of preventing alteration of basic properties of the peptide (e.g., physical properties, function, physiological activity, or immunological activity) in the introduction of a mutation, for example, mutual substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable.

(JMJD3)

JMJD3 is known as a demethylase for H3K27me3 of a histone (mouse NP_001017426, human NP_001073893), and even in its full length (NP_001073893, SEQ ID NO: 3), has an action of substantially removing or reducing the H3K27me3 modification of pluripotent stem cells. Surprisingly, the inventors of the present invention have confirmed that JMJD3c having the JmjC domain {SEQ ID NO: 4, catalytic domain: SEQ ID NO: 5 (amino acids 1376-1484)} has a stronger action of substantially removing or reducing H3K27me3 modification as compared to full-length JMJD3.

A preferred base sequence of JMJD3 is a base sequence set forth in SEQ ID NO: 32.

In addition, the JMJD3 of the present invention includes the following embodiments as well:

(1) a protected derivative, sugar chain-modified derivative, acylated derivative, or acetylated derivative of an amino acid sequence set forth in SEQ ID NO: 3;

(2) an amino acid sequence that has 90% (or 92%, 94%, 96%, 98%, or 99%) or more homology to the amino acid sequence set forth in SEQ ID NO: 3 and has a substantially equivalent action of substantially removing or reducing H3K27me3 modification to that of the JMJD3;

(3) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 3 and has a substantially equivalent action of substantially removing or reducing H3K27me3 modification to that of the JMJD3;

(4) a protected derivative, sugar chain-modified derivative, acylated derivative, or acetylated derivative of an amino acid sequence set forth in SEQ ID NO: 4;

(5) an amino acid sequence that has 90% (or 92%, 94%, 96%, 98%, or 99%) or more homology to the amino acid sequence set forth in SEQ ID NO: 4 and has a substantially equivalent action of substantially removing or reducing H3K27me3 modification to that of the JMJD3c;

(6) an amino acid sequence that has 100 to 10, 50 to 30, 40 to 20, 10 to 5, or 5 to 1 amino acid substituted, deleted, inserted, and/or added in the amino acid sequence set forth in SEQ ID NO: 4 and has a substantially equivalent action of substantially removing or reducing H3K27me3 modification to that of the JMJD3c; and (7) an amino acid sequence that includes the amino acid sequence set forth in SEQ ID NO: 5 and has a substantially equivalent action of substantially removing or reducing H3K27me3 modification to the JMJD3c.

It is appropriate that the "sequence homology" be generally 70% or more, preferably 80%, more preferably 85% or more, still more preferably 90% or more, even more preferably 95% or more, most preferably 98% or more of an entire amino acid sequence.

In addition, the JMJD3 gene of the present invention includes the following:

(1) a gene encoding a polypeptide consisted of an amino acid sequence set forth in any one of SEQ ID NOS: 3 to 5;

(2) a gene encoding a polypeptide that has 1 to 20 (or 1 to 15, 1 to 10, 1 to 7, 1 to 5, or 1 to 3) amino acids substituted, deleted, inserted, and/or added in the amino acid sequence set forth in any one of SEQ ID NOS: 3 to 5 and has a substantially equivalent action of substantially removing or reducing H3K27me3 modification to that of the amino acid sequence set forth in any one of SEQ ID NOS: 3 to 5;

(3) a gene encoding a polypeptide that has 90% (or 92%, 94%, 96%, 98%, or 99%) or more homology to the amino acid sequence set forth in any one of SEQ ID NOS: 3 to 5 and has a substantially equivalent action of substantially removing or reducing H3K27me3 modification to that of the amino acid sequence set forth in any one of SEQ ID NOS: 3 to 5;

(4) a gene consisted of a base sequence set forth in any one of SEQ ID NOS: 6 to 8 and 32;

(5) a gene encoding a polypeptide that hybridizes with a base sequence complementary to the base sequence set forth in any one of SEQ ID NOS: 6 to 8 and 32 under stringent conditions and has a substantially equivalent action of substantially removing or reducing H3K27me3 modification to that of the amino acid sequence set forth in any one of SEQ ID NOS: 3 to 5;

(6) a gene that has a sequence of 1 to 50 (or 1 to 40, 1 to 30, 1 to 20, 1 to 15, 1 to 10, 1 to 5, or 1 to 3 bases substituted, deleted, inserted, and/or added in the DNA consisted of the base sequence set forth in any one of SEQ ID NOS: 6 to 8 and 32; and (7) a gene having 90% (or 92%, 94%, 96%, 98%, or 99%) or more homology to the gene formed of the base sequence set forth in any one of SEQ ID NOS: 6 to 8 and 32.

(Transcription Factor Required for Highly Efficient Induction of Differentiation into Desired Cell Type)

The embodiment of the "transcription factor required for highly efficient induction of differentiation into the desired cell type" to be used in the method of the present invention is not particularly limited, but examples thereof may include, but not particularly limited to, nucleic acids, such as RNA and DNA, synthetic nucleic acids, and proteins.

In addition, in the method of the present invention, examples of the desired cell type may include a skeletal muscle, the liver (hepatocytes), neurons, chondrocytes, bone cells, and hematopoietic cells.

{Transcription Factor Required for Induction of Differentiation into Skeletal Muscle (in Particular, Cells Present in Skeletal Muscle)}

A method of inducing differentiation into a skeletal muscle is as described below.

A single transcription factor, or two or more transcription factors selected from the group of MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, PITX2, JUNB, KLF4, ESX1, TFAP2C, FOS, TFE3, FOSL1, GRHL2, TBX2, NFIB, and IRF4 are introduced into pluripotent stem cells. In particular, MYOD1 is preferably introduced into pluripotent stem cells.

{Transcription Factor Required for Induction of Differentiation into Liver (in Particular, Cells Present in Liver, i.e., Hepatoblasts)}

A method of inducing differentiation into the liver (in particular, the liver or the fetal liver) is as described below.

Liver: A single transcription factor, or two or more transcription factors selected from HNF1A, TCF-1, SALL4, TGIF1, MAB21L3, ZIC1, EGFLAM, PITX2, HNF4A, NRF1, ZNF281, CTCFL, TP73, TFE3, DLX6, and TCF4 are introduced into human pluripotent stem cells.

Fetal liver: A single transcription factor, or two or more transcription factors selected from HNF1A, TCF-1, SIX5, HNF4A, SIN3A, ID1, and HNF1A are introduced into human pluripotent stem cells.

In particular, HNF1A is preferably introduced into pluripotent stem cells.

(Transcription Factor Required for Induction of Differentiation into Neurons)

A method of inducing differentiation into neurons is as described below.

A single transcription factor, or two or more, three or more, four or more, or five transcription factors selected from NEUROG1, NEUROG2, NEUROG3, NEUROD1, and NEUROD2 are introduced into human pluripotent stem cells.

(Method of Introducing Target Gene into Genome of Pluripotent Stem Cell)

Figure 5:
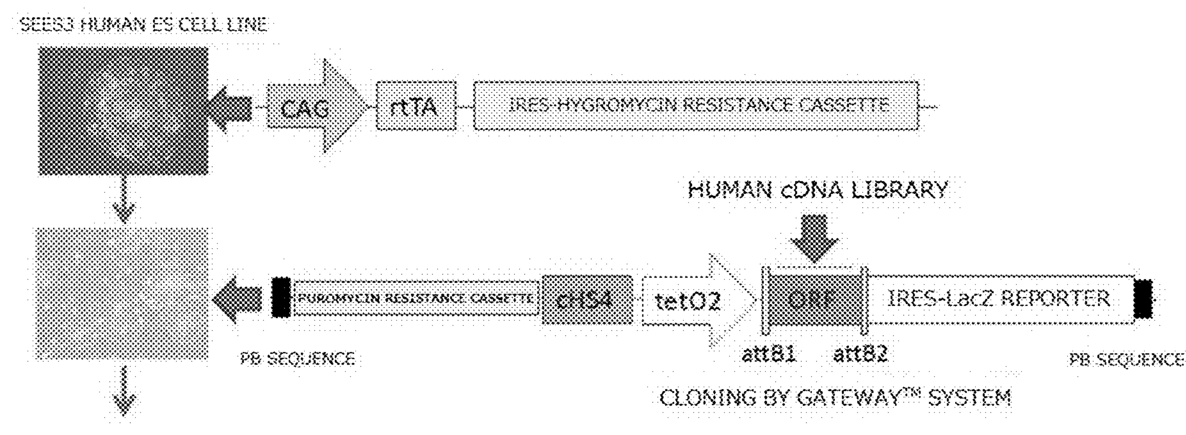
FIG. 5 A method of introducing a target gene into the genome of a pluripotent stem cell.

In a step of the method of the present invention, a method known per se may be used without any particular limitation as a method of introducing the gene for the compound having an action of substantially removing or reducing an expression amount of a POU5F1 protein (or the gene for the compound having an action of substantially removing or reducing H3K27me3 modification) and/or the transcription factor required for highly efficient induction of differentiation into the desired cell type into the genome of the pluripotent stem cell. There may be preferably used an expression cassette inserted between PiggyBac transposase recognition sequences (PB sequences) developed by Woltjen et al. (reference: Nature 458: 766-770, 2009), which is a mechanism by which a gene to be introduced is actively incorporated into pluripotent stem cells (in particular, the genome of human ES cells). The expression cassette is a system capable of efficiently establishing a genetically modified pluripotent stem cell line by introducing a drug selection cassette (see FIG. 5).

(Method of Introducing Target Protein into Pluripotent Stem Cell)

In a step of the method of the present invention, a method known per se may be used as a method of introducing the compound having an action of substantially removing or reducing an expression amount of a POU5F1 protein (or the compound having an action of substantially removing or reducing H3K27me3 modification) (in particular, protein) and/or the transcription factor (protein) required for highly efficient induction of differentiation into the desired cell type into the genome of the pluripotent stem cell, and examples thereof may include: a method involving using a protein transfection reagent; a method involving using a fusion protein having added thereto a cell-penetrating peptide; and a microinjection method.

The "cell-penetrating peptide" of the present invention is a peptide having a property of migrating into a cell, more specifically a property of penetrating a cell membrane, still more specifically a property of penetrating a cell membrane or a nuclear membrane to penetrate into cytoplasm or a nucleus. The amino acid sequence of the peptide is not particularly limited, but examples thereof may include TAT (GRKKRRQRRRPQ: SEQ ID NO: 9), r8 {rrrrrrrr (D-form-R): SEQ ID NO: 10}, and MPG-8 (βAFLGWLGAWGTMGWSPKKKRK: SEQ ID NO: 11).

The target protein encompasses both of the compound having an action of substantially removing or reducing an expression amount of a POU5F1 protein (or the compound having an action of substantially removing or reducing H3K27me3 modification) (in particular, protein) and/or the transcription factor (protein) required for highly efficient induction of differentiation into the desired cell type.

(Gene Knockout Method)

A gene knockout method is available as a method other than the foregoing. A "pluripotent stem cell in which a POU5F1 gene has been disrupted" may be generated by the gene knockout method. The "pluripotent stem cell in which a POU5F1 gene has been disrupted" means that normal expression of the POU5F1 gene is inhibited due to artificial modification of the sequence of a POU5F1 gene region, and as a result, the expression of POU5F1 is suppressed and a POU5F1 protein is not normally expressed.

In addition, the "whole" in "modification or deletion of part or the whole of the POU5F1 gene" refers to the protein-coding region of POU5F1 genomic DNA.

In addition, the "part" refers to a region that is part of the protein-coding region and that has a length required for inhibiting normal expression of the POU5F1 gene.

Further, the "modification" refers to modification of the base sequence of a target region in genomic DNA into another base sequence by substituting, deleting, inserting, and/or adding a single nucleotide or two or more of nucleotides.

(Differentiation Induction Kit for Inducing Differentiation of Pluripotent Stem Cell into Desired Cell Type with High Efficiency)

A differentiation induction kit for inducing differentiation of a pluripotent stem cell into a desired cell type with high efficiency of the present invention (hereinafter sometimes referred to as "kit of the present invention") includes any one or more of the following modes.

(1) Pluripotent Stem Cell in which Expression Amount of POU5F1 Protein has been Substantially Removed or Reduced and/or H3K27Me3 Modification has been Substantially Removed or Reduced A pluripotent stem cell in which an expression amount of a POU5F1 protein has been substantially removed or reduced and/or H3K27me3 modification has been substantially removed or reduced can be easily generated by the method of the present invention described above.

A implementer can easily induce differentiation into the desired cell type by introducing the transcription factor required for induction of differentiation into the desired cell type as described above into the pluripotent stem cell.

In addition, such pluripotent stem cell encompasses a pluripotent stem cell having a gene construct inducible with doxycycline or the like inserted into the genome thereof so that a gene for a compound having an action of substantially removing or reducing an expression amount of a POU5F1 protein, a demethylase, or the like can be transiently forcibly expressed therein.

(2) Gene for Compound Having Action of Substantially Removing or Reducing Expression Amount of POU5F1 Protein and/or Demethylase Gene for Kit of the Present Invention The implementer can easily generate the pluripotent stem cell in which an expression amount of a POU5F1 protein has been substantially removed or reduced and/or H3K27me3 modification has been substantially removed or reduced by adding a gene for a compound having an action of substantially removing or reducing an expression amount of a POU5F1 protein and/or a demethylase gene for a kit to a pluripotent stem cell.

Examples of the anti-POU5F1 antibody gene for a kit may include, but not particularly limited to, commercially available antibody genes.

Examples of the demethylase gene for a kit may include, but not particularly limited to, mRNAs, DNAs, and proteins of demethylase genes (e.g., JMJD3c).

(3) Gene for Compound Having Action of Substantially Removing or Reducing Expression Amount of POU5F1 Protein and/or Demethylase Gene, and Gene Containing Transcription Factor Required for Induction of Differentiation into Desired Cell Type for Kit of the Present Invention The implementer can easily generate the pluripotent stem cell in which an expression amount of a POU5F1 protein has been substantially removed or reduced and/or H3K27me3 modification has been substantially removed or reduced, and further, can induce differentiation thereof into the desired cell type with high efficiency by adding a gene for a compound having an action of substantially removing or reducing an expression amount of a POU5F1 protein and/or a demethylase gene, and a gene containing a transcription factor required for induction of differentiation into the desired cell type for a kit to a pluripotent stem cell.

Those genes may be present on one gene, or on separate genes. When the genes are present on separate genes, the gene for the compound having an action of substantially removing or reducing an expression amount of a POU5F1 protein (or demethylase gene) and the transcription factor required for induction of differentiation into the desired cell type may be added to the pluripotent stem cell simultaneously or at separate times.

(4) Compound Having Action of Substantially Removing or Reducing Expression Amount of POU5F1 Protein and/or Demethylase for Kit of the Present Invention The implementer can easily generate the pluripotent stem cell in which an expression amount of a POU5F1 protein has been substantially removed or reduced and/or H3K27me3 modification has been substantially removed or reduced by adding a compound having an action of substantially removing or reducing an expression amount of a POU5F1 protein and/or a demethylase for a kit to a pluripotent stem cell.

(5) Gene Construct Carrying Gene for Compound Having Action of Substantially Removing or Reducing Expression Amount of POU5F1 Protein and/or Demethylase Gene The user can easily generate the pluripotent stem cell in which an expression amount of a POU5F1 protein has been substantially removed or reduced and/or H3K27me3 modification has been substantially removed or reduced by introducing a gene construct carrying a gene for a compound having an action of substantially removing or reducing an expression amount of a POU5F1 protein and/or a demethylase gene into the genome of a pluripotent stem cell.

The gene construct may contain a promoter sequence, a gene expression-enhancing sequence, a marker gene, a reporter sequence, a drug resistance gene, and the like as required in addition to the gene for the compound having an action of substantially removing or reducing an expression amount of a POU5F1 protein and/or the demethylase gene.

(6) Gene Construct Carrying: Gene for Compound Having Action of Substantially Removing or Reducing Expression Amount of POU5F1 Protein and/or Demethylase Gene; and Transcription Factor Required for Induction of Differentiation into Desired Cell Type The implementer can easily generate the pluripotent stem cell in which an expression amount of a POU5F1 protein has been substantially removed or reduced and/or H3K27me3 modification has been substantially removed or reduced, and further, can induce differentiation thereof into the desired cell type by introducing a gene construct carrying: a gene for a compound having an action of substantially removing or reducing an expression amount of a POU5F1 protein and/or a demethylase gene; and a transcription factor required for induction of differentiation into the desired cell type into the genome of a pluripotent stem cell.

Those genes may be present on one gene, or on separate genes. When the genes are present on separate genes, the gene for the compound having an action of substantially removing or reducing an expression amount of a POU5F1 protein and/or the demethylase gene, and the transcription factor required for induction of differentiation into the desired cell type may be expressed in the genome of the pluripotent stem cell simultaneously or at separate times.

The gene construct may contain a promoter sequence, a gene expression-enhancing sequence, a marker gene, a reporter sequence, a drug resistance gene, and the like as required in addition to the gene for the compound having an action of substantially removing or reducing an expression amount of a POU5F1 protein and/or the demethylase gene, and the transcription factor required for induction of differentiation into the desired cell type.

(Proteins Associated with Undifferentiated State Maintenance Other than POU5F1)

NANOG, SOX2, SOX3, KLF2, KLF4, KLF5, TBX3, ESRRB, SALL4, STAT3, ZIC3, LIN28, and TCF3 are known as proteins associated with undifferentiated state maintenance. Accordingly, it is considered that pluripotent stem cells in which expression amounts of the proteins of NANOG, SOX2, SOX3, KLF2, KLF4, KLF5, TBX3, ESRRB, SALL4, STAT3, ZIC3, LIN28, and TCF3 have been substantially removed or reduced can be differentiated into the desired cell type with high efficiency.

Further, a pluripotent stem cell in which an expression amount of any one or more of the above-mentioned proteins has been substantially removed or reduced and an expression amount of a POU5F1 protein has been substantially removed or reduced (pluripotent stem cell in which an expression amount of any one or more of the above-mentioned proteins has been substantially removed or reduced and an expression amount of a POU5F1 protein has been substantially removed or reduced, and which has a histone in which H3K27me3 modification has been substantially removed or reduced) is also included in the present invention.

In addition, a method of differentiating a pluripotent stem cell into a desired cell type including a step of adding a gene for a compound having an action of substantially removing or reducing an expression amount of any one or more of the above-mentioned proteins, a gene for a compound having an action of substantially removing or reducing an expression amount of a POU5F1 protein (further, a demethylase gene or the like), and a transcription factor required for induction of differentiation into the desired cell type to a pluripotent stem cell is also encompassed in the present invention.

A method of differentiating a pluripotent stem cell into a desired cell type of the present disclosure may be exemplified by, but not particularly limited to, a method including any one of the following steps (1) to (9):

(1) a step of adding a gene for a compound having an action of substantially removing or reducing an expression amount of a POU5F1 protein and a transcription factor required for induction of differentiation into the desired cell type to a pluripotent stem cell;

(2) a step of inserting a gene construct carrying a gene for a compound having an action of substantially removing or reducing an expression amount of a POU5F1 protein and a transcription factor gene required for induction of differentiation into the desired cell type, into a genome of a pluripotent stem cell;

(3) a step of inserting a gene construct carrying a gene for a compound having an action of substantially removing or reducing an expression amount of a POU5F1 protein and a gene construct carrying a transcription factor required for induction of differentiation into the desired cell type, into a genome of a pluripotent stem cell;

(4) a step of adding a transcription factor required for induction of differentiation into the desired cell type to a pluripotent stem cell in which an expression amount of a POU5F1 protein has been substantially removed or reduced;

(5) a step of adding a transcription factor required for induction of differentiation into the desired cell type to a pluripotent stem cell in which a compound having an action of substantially removing or reducing an expression amount of a POU5F1 protein is forcibly expressed;

(6) a step of adding a compound having an action of substantially removing or reducing an expression amount of a POU5F1 protein and a transcription factor required for differentiation into the desired cell type to a pluripotent stem cell;

(7) a step of adding a transcription factor required for induction of differentiation into the desired cell type to a pluripotent stem cell in which a POU5F1 gene has been disrupted;

(8) a step of adding a gene for a compound having an action of substantially removing or reducing an expression amount of a POU5F1 protein, a demethylase gene, and a transcription factor required for induction of differentiation into the desired cell type to a pluripotent stem cell; and (9) a step of adding a transcription factor required for induction of differentiation into the desired cell type to a pluripotent stem cell in which an expression amount of a POU5F1 protein has been substantially removed or reduced and which has a histone in which H3K27me3 modification has been substantially removed or reduced.

The present disclosure also includes any one of the following pluripotent stem cells for differentiation into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present disclosure also includes a use of any one of the following pluripotent stem cells for differentiation into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present disclosure also includes a use of any one of the following pluripotent stem cells for differentiation into a desired cell type, in production of a differentiation induction kit for differentiating a pluripotent stem cell into a desired cell type:

(1) a pluripotent stem cell for differentiation into a desired cell type, in which an expression amount of a POU5F1 protein has been substantially removed or reduced;

(2) a pluripotent stem cell for differentiation into a desired cell type, in which a gene for a compound having an action of substantially removing or reducing an expression amount of a POU5F1 protein is forcibly expressed;

(3) a pluripotent stem cell for differentiation into a desired cell type, which has a gene construct carrying a gene for a compound having an action of substantially removing or reducing an expression amount of a POU5F1 protein inserted into the genome thereof;

(4) a pluripotent stem cell for differentiation into a desired cell type, in which a POU5F1 gene has been disrupted; and (5) a pluripotent stem cell for differentiation into a desired cell type, in which an expression amount of a POU5F1 protein has been substantially removed or reduced and which has a histone in which H3K27me3 modification has been substantially removed or reduced.

The present invention is more embodied described below by Examples. However, the present invention is not limited to these Examples. All of these Examples have been approved by the Ethics Committee of Keio University School of Medicine.

Example 1

(Materials and Methods)

Examples 2 to 6 were carried out using materials and methods described below. The details are as described below.

(Human Pluripotent Stem Cell Culture and Differentiation Induction Methods)

Human ES cell (hESC) lines SEES-3 and H9 were obtained from the National Center for Child Health and Development (National Research Institute for Child Health and Development) and the Cell Research Institute, USA, respectively. A human induced pluripotent stem cell (hiPSC) line was obtained from RIKEN or the Center for iPS Cell Research and Application, Kyoto University. hESC/iPSCs were cultured using StemFit AK-03 medium (Ajinomoto) on iMatrix-511 (Nippi)-coated plates without use of feeder cells. A ROCK (Rho-associated coiled-coil forming kinase/Rho-associated kinase) inhibitor Y-27632 was added to the medium during cell subculture in order to inhibit apoptosis induced by cell detachment during cell passaging.

For myogenic differentiation, the hESC/iPSCs were cultured in a medium of a MEM (Gibco) supplemented with 5% KSR, 1 mM sodium pyruvate, 0.1 mM non-essential amino acids, 2 mM glutamine, 0.1 mM β-mercaptoethanol, and penicillin/streptomycin (50 U/50 μg/ml) on iMatrix-511-coated plates.

For albumin secretion hepatocyte differentiation, the hESC/iPSCs were cultured in the above-mentioned medium on Matrigel (BD)-coated plates, then cultured in RPMI 1640 medium supplemented with 1 mM NaB, 100 ng/ml Activin A, 50 ng/ml Wnt3a, 1× B27, and 2 mM GlutaMAX for 1 day, subsequently cultured in DMEM medium supplemented with 1% DMSO, 0.5 mM MTG, 1% NEAA, 1 mM GlutaMAX, and 20% KSR for 5 days, and finally cultured in HCM medium (Lonza) supplemented with 20 ng/ml HGF and 20 ng/ml Oncostatin M for 7 days.

(siRNA Transfection)

siRNA against POU5F1 (sense strand: GCCCGAAAGAGAAAGCGAATT: SEQ ID NO: 12, antisense strand: UUCGCUUUCUCUUUCGGGCCT: SEQ ID NO: 13) identical to that used in the literature "Proceeding of national academy of sciences 109, 4485-4490 (2012)" was purchased from Applied Biosystems and used (product number: s10873). siRNA serving as a negative control was also purchased from Applied Biosystems and used. siRNA transfections were performed with Lipofectamine MessengerMax (Invitrogen), according to the instructions of the accompanying manual. The B18R interferon inhibitor (eBioscience) was added to the culture medium to increase the viability of the transfected cells. The medium was replaced 2 hours to 3 hours after each transfection.

(Modified mRNA Synthesis and Transfection)

The protein-coding regions (Open Reading Frames, ORFs) of a red fluorescent protein mCherry, a green fluorescent protein Emerald, and tissue-specific transcription factors {MYOD1 (SEQ ID NO: 26), HNF1A (SEQ ID NO: 27), RUNX2 (SEQ ID NO: 28), SOX9 (SEQ ID NO: 29), SPI1 (SEQ ID NO: 30), and ASCL1 (SEQ ID NO: 31)} were subcloned into a pCRII construct containing the 5' UTR and 3' UTR of mouse α-globin, which increased mRNA stability and translation efficiency, to prepare templates used to synthesize mRNAs.

Modified mRNAs were synthesized on the basis of the description of the literature "Cell stem cell 7, 618-630 (2010)". Briefly speaking, a T7 promoter and a poly(A) tail were added through PCR reaction using a KAPA taq kit (Kapa Biosystems). RNAs were synthesized from PCR products using a MEGAscript T7 kit (Ambion) together with ARCA cap analog (New England Biolabs), ATP, GTP, 5-Methyl-CTP (TriLink), and pseudo-UTP (TriLink). The synthetic mRNAs were purified using a MEGAclear kit (Ambion). Synthetic mRNA transfections were performed with Lipofectamine MessengerMax (Invitrogen) according to the instructions of the accompanying manual. The B18R interferon inhibitor (eBioscience) was added to the culture medium to increase the viability of the transfected cells. The medium was replaced 2 hours to 3 hours after each transfection.

(Antibody)

The following antibodies were used:

POU5F1 (Santa Cruz, sc-5279);

β-ACTIN (Cell Signaling, 4970S);

MyHC (R&D MAB4470);

ALBUMIN (Abcam ab10241); and

AFP (R&D MAB1368).

(Immunostaining)

The cells were fixed in 4% PFA for 10 minutes at room temperature and permeabilized in 0.5% Triton-X-containing PBS for 10 minutes. The cells were treated a blocking in 2% BSA-containing PBS for 10 minutes, and cultured with primary antibodies in a blocking solution (1:500) for from 2 hours to 3 hours at room temperature or overnight at 4° C. The cells were washed twice in PBS, and then cultured with Alexa dye-conjugated secondary antibodies (Invitrogen) in a blocking solution (1:500) for 1 hour at room temperature. Nuclei were counterstained with DAPI (Dako). Immunofluorescence was visualized with an inverted fluorescence microscope IX73 (Olympus). Images were obtained using Olympus cellSens imaging software.

(Immunoblotting Method)

The cells were lysed with a sample buffer (50 mM Tris-HCl, pH 6.8, 2% SDS, 6% 2-mercaptoethanol, and 500 mg/ml urea). The proteins were separated by SDS-PAGE using a 4-15% polyacrylamide gel (Biorad) and were electrically transferred to polyvinylidene fluoride membranes (Biorad). The membranes were blocked for 1 hour in 0.1% Tween-20-containing Tris-buffered saline (TBST) and 5% skimmed milk. The membranes were washed in TBST and then incubated with primary antibodies in 2% BSA-containing TBS (1:1,000 dilution) for from 2 hours to 3 hours at room temperature or overnight at 4° C. The membranes were washed and incubated with horseradish peroxidase-conjugated secondary antibodies (GE) for 1 hour at room temperature. The membranes were washed in TBST, and immunoreactivity was visualized using ECL Prime Detection Kit (GE) and detected using Luminescent Image Analyzer (LAS-4000; Fujifilm).

(qRT-PCR)

Total RNA was isolated with TRIzol reagent (Invitrogen), and cDNAs were generated with random hexamers using a ReverTra Ace kit (Toyobo). Real-time PCR was performed using a SYBR Green PCR system (Takara). The primer sequences used for RT-PCR are listed below.

```
MYOG primer (Forward):
                                   (SEQ ID NO: 14)
gccagactatccccttcctc

MYOG primer (Reverse):
                                   (SEQ ID NO: 15)
gaggccgcgttatgataaaa

AFP primer (Forward):
                                   (SEQ ID NO: 16)
tgggacccgaactttcca

AFP primer (Reverse):
                                   (SEQ ID NO: 17)
ggccacatccaggactagtttc

COL1A1 primer (Forward):
                                   (SEQ ID NO: 18)
cctggatgccatcaaagtct

COL1A1 primer (Reverse):
                                   (SEQ ID NO: 19)
tcttgtccttggggttcttg

COL2A1 primer (Forward):
                                   (SEQ ID NO: 20)
tttcccaggtcaagatggtc

COL2A1 primer (Reverse):
                                   (SEQ ID NO: 21)
cttcagcacctgtctcacca

CD45 primer (Forward):
                                   (SEQ ID NO: 22)
tcctggactcccaaaatctg

CD45 primer (Reverse):
                                   (SEQ ID NO: 23)
accttgaacccgaacatgag

NESTIN primer (Forward):
                                   (SEQ ID NO: 24)
tggttttccagagtcttcagtga

NESTIN primer (Reverse):
                                   (SEQ ID NO: 25)
gaaacagccatagagggcaaa
```

Example 2

(Pluripotent Stem Cells in which Expression Amount of POU5F1 Protein has been Reduced)

In this Example, it was confirmed whether pluripotent stem cells in which the expression amount of a POU5F1 protein had been forcibly reduced were able to be generated or not. The details are as described below.

(Confirmation of Suppression of Expression of POU5F1 by siRNA Transfection)

Figure 6:
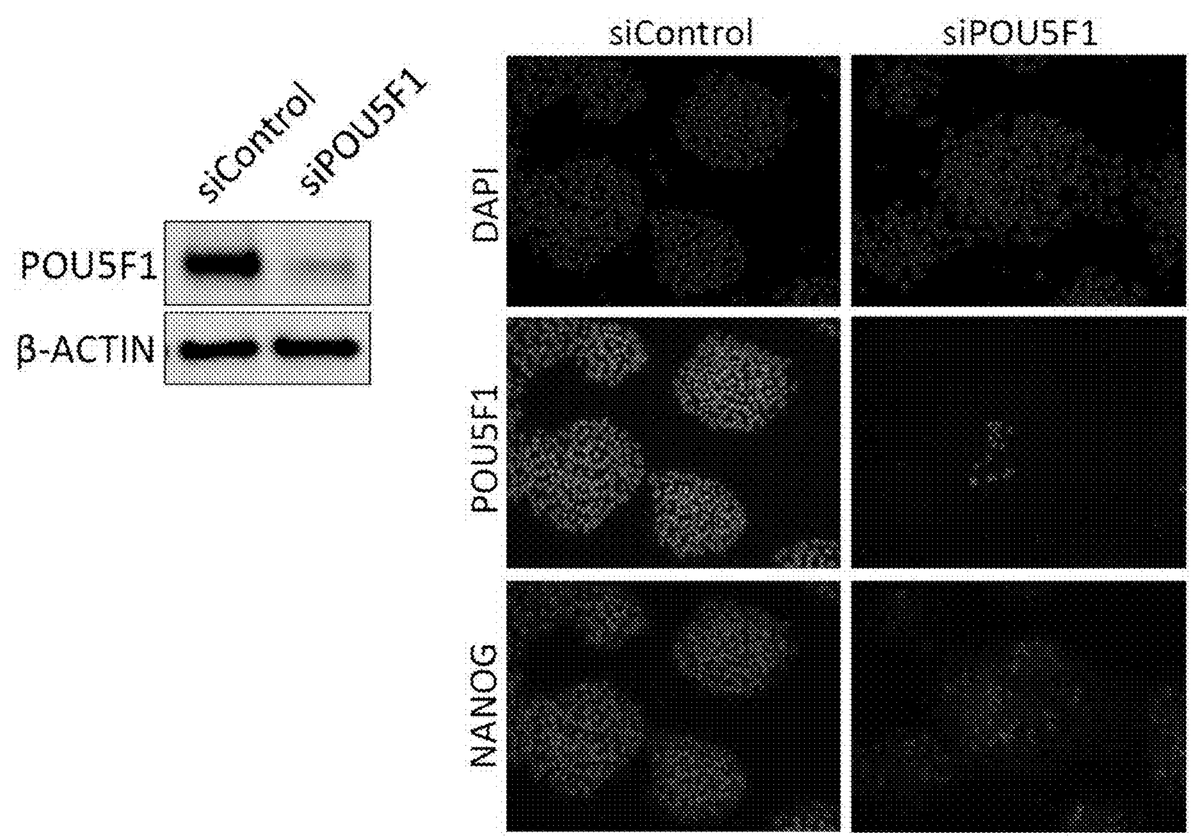
FIG. 6 The suppression of the expression of the POU5F1 protein by siRNA. Human ES cells were transfected with siRNA of POU5F1 (siPOU5F1), and it was confirmed by western blot using a specific antibody that the protein of POU5F1 was decreased (left figures) and it was confirmed by an immunostaining method using a specific antibody that the proteins of POU5F1 and NANOG were decreased (right figures). As a control, scramble siRNA (siControl) not acting on any gene was used. β-ACTIN represents a "loading control", and DAPI represents "cell nuclei".

Effects of siRNA (siPOU5F1) on POU5F1 in human ES cells were confirmed by an immunoblotting method and an immunostaining method (FIG. 6). Cells on Day 3 after siPOU5F1 transfection were analyzed, and as a result, it was confirmed that the POU5F1 protein was significantly decreased as compared to cells transfected with negative control siRNA (scramble siRNA sequence against POU5F1: siControl) (FIG. 6). The siPOU5F1 transfection decreased an NANOG protein serving as a molecular marker for pluripotent stem cells.

Thus, the disappearance of pluripotency by the siPOU5F1 transfection was confirmed.

(Confirmation of Morphological Change of Human ES Cells by siPOU5F1 Transfection)

Figure 7:
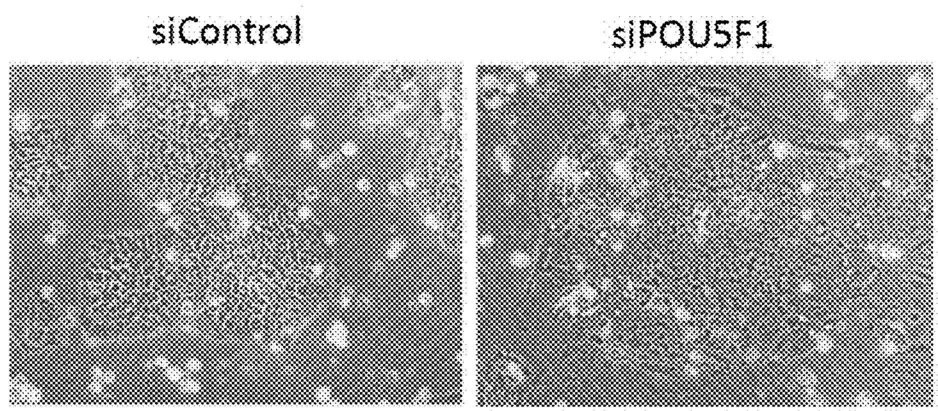
FIG. 7 The morphological change of pluripotent stem cells by siPOU5F1. It is shown that human ES cells changed into flat shapes when transfected with siPOU5F1.

Human ES cells have small round shapes when their undifferentiated state is maintained. It was confirmed that cells underwent a morphological change into flat shapes when transfected with siPOU5F1, and were directed toward differentiation through POU5F1 suppression (FIG. 7).

As this Example's result, it was confirmed that pluripotent stem cells in which the expression amount of the POU5F1 protein had been reduced were able to be generated, and that the cells were promoted toward differentiation.

Example 3

(Confirmation of Induction of Differentiation of Pluripotent Stem Cells in which Expression Amount of POU5F1 Protein has been Reduced into Desired Cell Types)

In this Example, it was confirmed whether differentiation into desired cell types was induced by introducing (adding) transcription factors required for induction of differentiation into the desired cell types to pluripotent stem cells in which the expression amount of the POU5F1 protein had been reduced. The details are as described below.

siPOU5F1 and modified synthetic RNAs (synRNAs) for a tissue-specific transcription factors were introduced into human ES cells, and the expression of differentiation marker genes MYOG (skeletal muscles), AFP (hepatocytes), COL1A1 (bone cells), COL2A1 (cartilage), CD45 (hematopoietic cells), and NESTIN (nerves) was examined by a real-time RT-PCR method.

Figure 8:
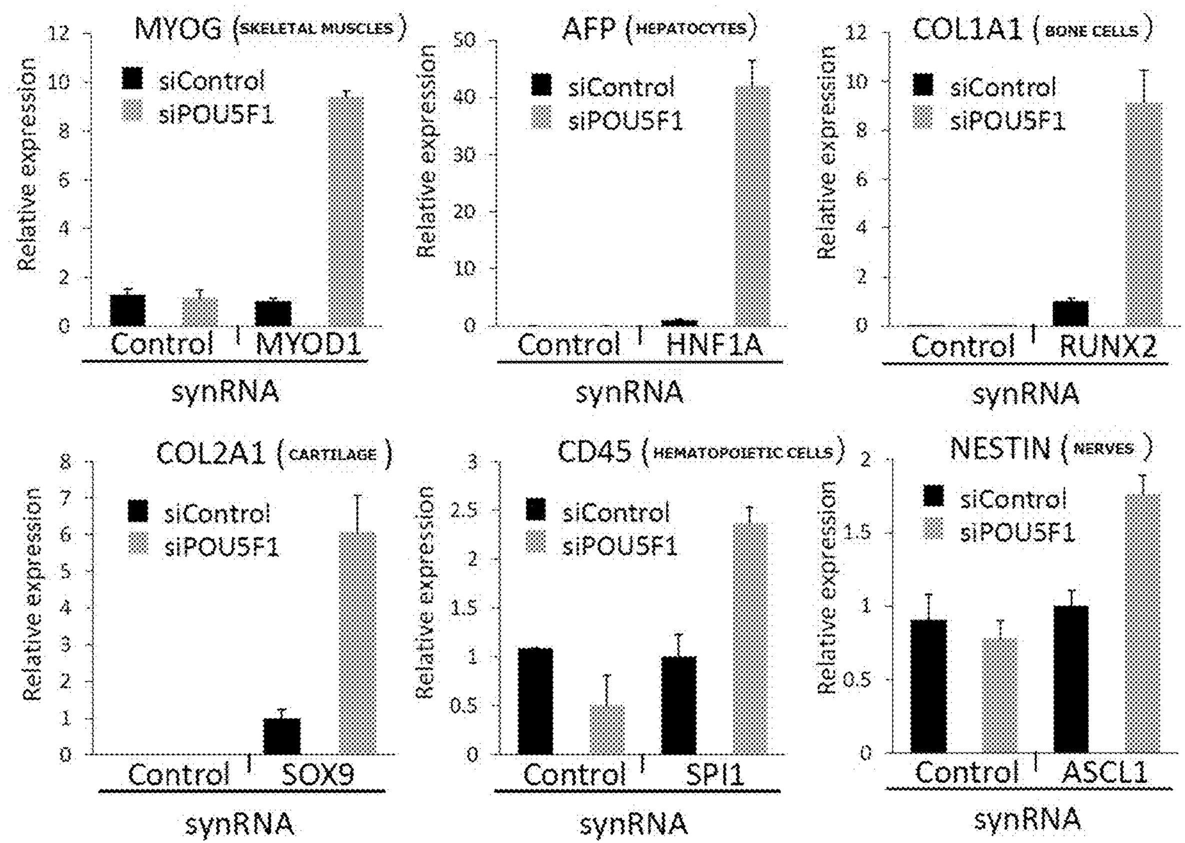
FIG. 8 It is shown that the co-transfection of siPOU5F1 and transcription factor mRNA activates differentiation genes. It was confirmed by a real-time PCR method that the transfection of human ES cells with modified synthetic RNAs (synRNAs) for tissue-specific transcription factors (MYOD1, HNF1A, RUNX2, SOX9, SPI1, and ASCL1) in combination with siPOU5F1 increased the expression of respective differentiation marker genes (MYOG, AFP, COL1A1, COL2A1, CD45, and NESTIN). Right bars represent cases of transfection with siPOU5F1, and left bars represent cases of transfection with siControl. mCherry or Emerald was used as synRNA serving as a negative control.

As the tissue-specific transcription factors, MYOD1 (skeletal muscles), HNF1A (liver), RUNX2 (bone cells), SOX9 (cartilage), SPI1 (blood), and ASCL1 (nerves) were used. As a negative control, synRNA for mCherry or Emerald was introduced.

siControl or siPOU5F1 and synRNA were simultaneously introduced (added) to the cells, and 1 day after that, the synRNA was further introduced thereto twice. The next day (2 days after the first introduction), the cells were sampled and analyzed. The medium used was a medium for undifferentiated state maintenance. As a result, it was confirmed that, when siPOU5F1 was introduced in combination with the transcription factors, the expression of the differentiation markers for the respective tissues was significantly increased (FIG. 8). While, as siControl or the transcription factors were introduced alone, any increases in expression of the differentiation markers were hardly detected (FIG. 8).

As this Example's result, it was confirmed that differentiation into desired cell types was efficiently induced by introducing (adding) the transcription factors required for induction of differentiation into the desired cell types to the pluripotent stem cells in which the expression amount of the POU5F1 protein had been reduced.

Example 4

(Confirmation of Differentiation of Pluripotent Stem Cells in which Expression Amount of POU5F1 Protein has been Reduced into Desired Cell Types)

In this Example, as examples of induction of differentiation into desired cell types, a myogenic differentiation (skeletal muscle cell differentiation) model using a myogenesis-regulating master transcription factor MYOD1, and a hepatocyte differentiation model using hepatocyte nuclear factor-1-alpha (HNF1A) were adopted. It is known that forced expression of MYOD1 alone cannot cause sufficient epigenetic changes and transcriptional changes in hESCs, resulting in poor myogenic conversion (see Cell reports 3, 661-670 (2013)).

(Skeletal Muscle Cell Differentiation)

Human ES cells were co-transfected with siControl or siPOU5F1 and synRNA for MYOD1 (MYOD1-synRNA), and 1 day after that, were further transfected twice with MYOD1-synRNA. In this case, the cells were cultured in a skeletal muscle differentiation medium.

Two days after the last synRNA transfection, which was performed 2 days after the first transfection, the cells were fixed and immunostained. The ES cells transfected with siControl hardly underwent a morphological change even when transfected with MYOD1-synRNA, and few of the cells expressed Myosin Heavy Chain (MyHC) serving as a terminal differentiation marker for a skeletal muscle (FIG. 9).

Figure 9:
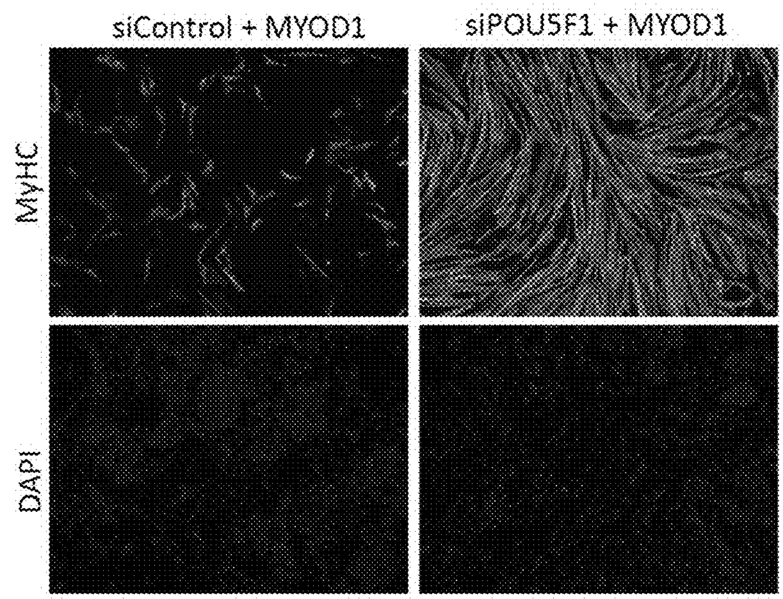
FIG. 9 Skeletal muscle differentiation by siPOU5F1 and MYOD1-synRNA was confirmed by an immunostaining method using an MyHC antibody. It was confirmed that, although MYOD1 alone (siControl+MYOD1) hardly caused muscle differentiation, its combination with siPOU5F1 dramatically induced muscle differentiation. MyHC represents a "terminal differentiation marker", and DAPI represents "cell nuclei".

However, as the ES cells transfected with siPOU5F1 were used, 2 days after the last MYOD1-synRNA transfection, fibrous muscle cells appeared at a high frequency and most of the cells were MyHC-positive, confirming that the cells were differentiated into skeletal muscle cells (FIG. 9).

Figure 10:
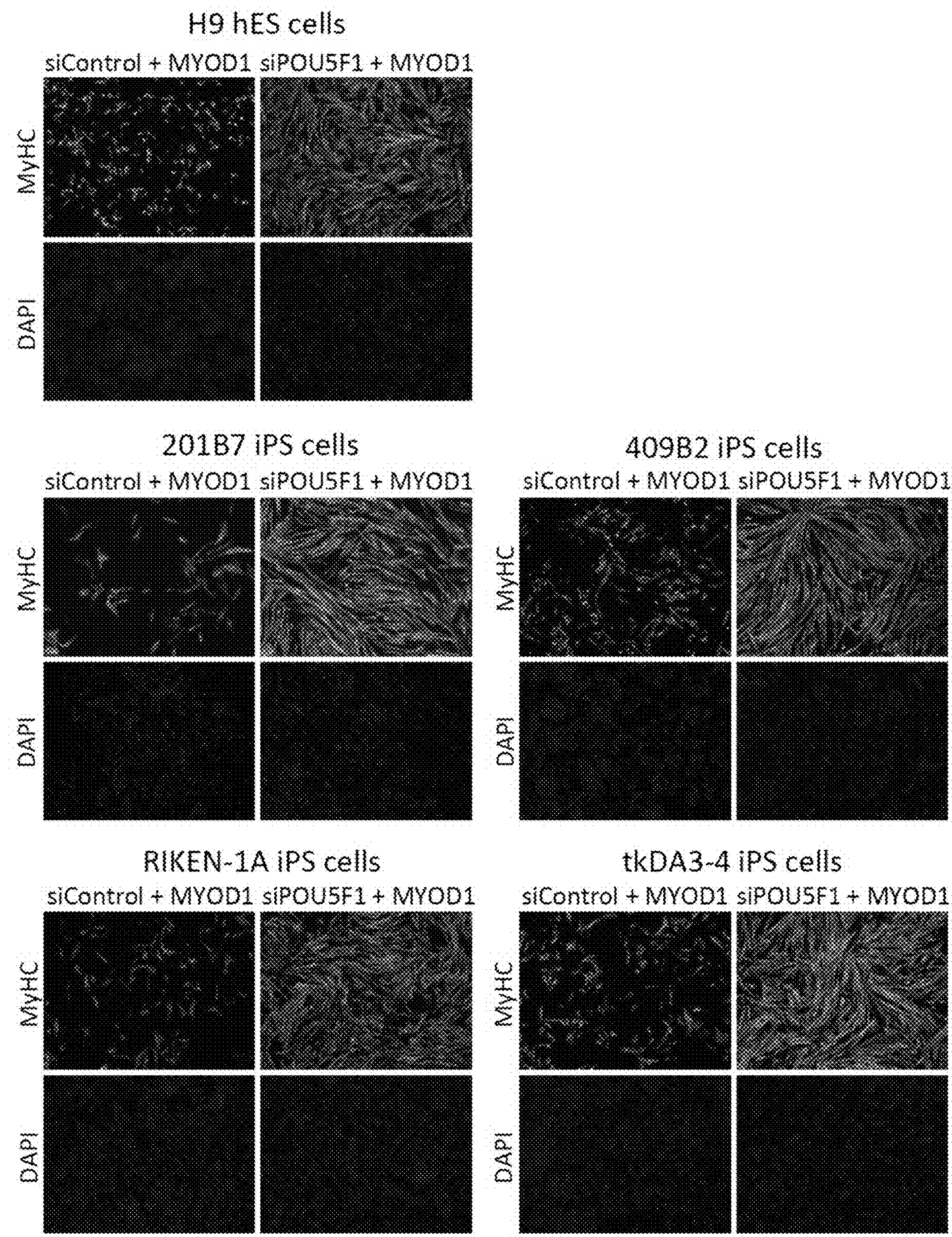
FIG. 10 Skeletal muscle differentiation in more than one ES cell lines and iPS cell lines by siPOU5F1 and MYOD1-synRNA was confirmed by an immunostaining method using an MyHC antibody. The co-expression of siPOU5F1 and MYOD1-synRNA was able to induce skeletal muscle differentiation rapidly and with high efficiency also in an H9 line serving as an ES cell line, and four kinds of iPS cell lines (201B7, 409B2, RIKEN-1A, and tkDA3-4).

In addition, similar effects were also able to be obtained in another ES cell line (H9 hES cell) and a plurality of iPS cell lines (201B7 iPS cell, 409B2 iPS cell, RIKEN-1A iPS cell, and tkDA3-4 iPS cell) (FIG. 10).

(Hepatocyte Differentiation)

Figure 11:
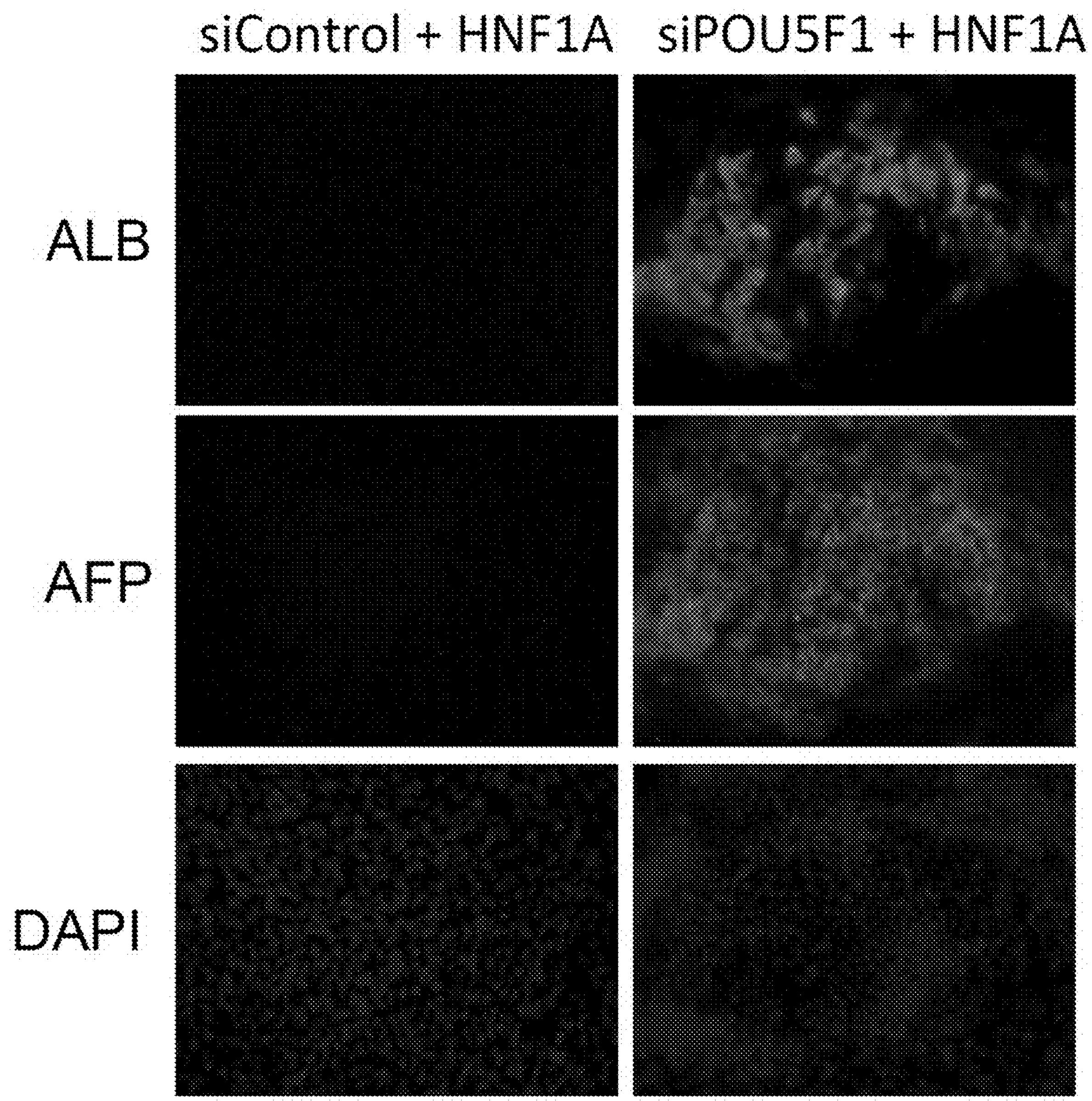
FIG. 11 Hepatocyte differentiation by siPOU5F1 and HNF1A-synRNA is shown by an immunostaining method using an albumin antibody and an AFP antibody. DAPI represents "cell nuclei".

Human ES cells were co-transfected with siControl or siPOU5F1 and synRNA for HNF1A (HNF1A-synRNA), and 1 day after that, were further transfected twice with HNF1A-synRNA. From the day after the last synRNA transfection, which was performed 2 days after the first transfection, the cells were cultured in a hepatocyte differentiation medium, and 13 days later, the cells were fixed and immunostained. While, the ES cells transfected with siControl were transfected with HNF1A-synRNA, cells expressing AFP and albumin (ALB) serving as differentiation markers for hepatocytes were hardly observed (FIG. 11). Beside, in the case of the cells co-transfected with siPOU5F1 and HNF1A-synRNA, many cells expressing albumin and AFP were observed, and thus it was confirmed that the cells were differentiated into hepatocytes (FIG. 11).

As this Example's result, it was confirmed that differentiation into desired cell types was able to be efficiently induced by introducing the transcription factors required for induction of differentiation into the desired cell types into the pluripotent stem cells in which the expression amount of the POU5F1 protein had been reduced.

Example 5

(Confirmation of Induction of Differentiation of Pluripotent Stem Cells in which Expression Amount of POU5F1 Protein has been Reduced and Demethylase is Forcibly Expressed into Desired Cell Types)

The inventors of the present invention have confirmed that pluripotent stem cells in which a demethylase is forcibly expressed allow the differentiation resistance of human pluripotent stem cells to disappear, thereby facilitating differentiation induction. A molecular mechanism by which the expression amount of the POU5F1 protein is reduced is different from a molecular mechanism by which the demethylase is forcibly expressed.

In view of the foregoing, it was confirmed whether differentiation into desired cell types was induced by introducing (adding) transcription factors required for induction of differentiation into the desired cell types to pluripotent stem cells in which the expression amount of the POU5F1 protein had been reduced and the demethylase was forcibly expressed, which were obtained by combining the reduction of the expression amount of the POU5F1 protein and the forced expression of the demethylase. The details are as described below.

Differentiation into the desired cell types was induced using synRNAs for tissue-specific transcription factors MYOD1, HNF1A, SOX9, and SPI1.

Figure 12:
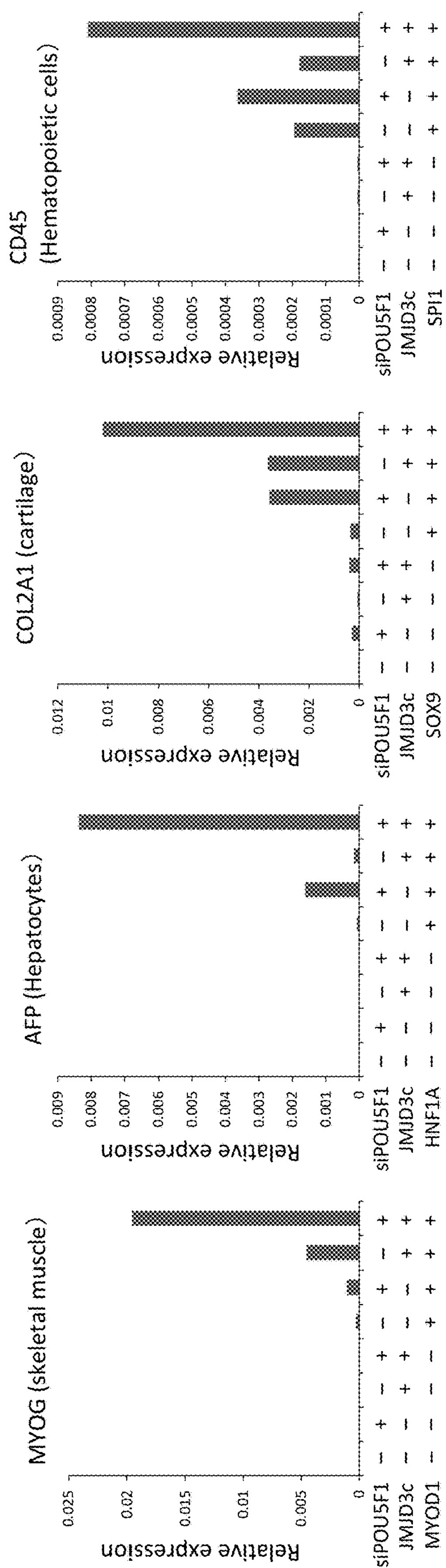
FIG. 12 It was confirmed by a real-time PCR method that differentiation induction by siPOU5F1 was further facilitated by combining forced expression of a demethylase therewith. It was confirmed that the expression of a differentiation marker gene (MYOG, AFP, COL2A, or CD45) activated by siPOU5F1 and a tissue-specific transcription factor (MYOD1, HNF1A, SOX9, or SPI1) was further upregulated by forced expression of the demethylase in a synergistic manner.

It was confirmed that the expression of differentiation marker genes MYOG (skeletal muscle), AFP (hepatocyte), COL2A1 (cartilage), CD45 (hematopoietic cell) was more increased in a synergistic manner in the case of differentiation performed by combining the reduction of the expression amount of the POU5F1 protein and the forced expression of the demethylase than in the case of differentiation performed by only one of the reduction of the expression amount of the POU5F1 protein or the forced expression of the demethylase, and the expression with synRNA (FIG. 12).

More specifically, an about 18.2-fold increase in expression of MYOG, an about 5.2-fold increase in expression of AFP, an about 2.8-fold increase in expression of COL2A1, and an about 2.2-fold increase in expression of CD45 were achieved by combining the reduction of the expression amount of the POU5F1 protein and the forced expression of the demethylase as compared to the case in which the expression amount of the POU5F1 protein was only reduced.

Further, the combination of the reduction of the expression amount of the POU5F1 protein and the forced expression of the demethylase achieved an about 4.3-fold increase in expression of MYOG, an about 54.0-fold increase in expression of AFP, an about 2.8-fold increase in expression of COL2A1, and an about 4.5-fold increase in expression of CD45 as compared to the case in which the demethylase was forcibly expressed.

In addition, in hepatocyte differentiation induction, the reduction of the expression amount of the POU5F1 protein achieved expression about 10.4 times as high as that achieved by the forced expression of the demethylase. Thus, concerning hepatocyte differentiation induction, the reduction of the expression amount of the POU5F1 protein showed a significant effect as compared to the forced expression of the demethylase.

As this Example's result, it was confirmed that the pluripotent stem cells in which the expression amount of the POU5F1 protein had been reduced and the demethylase was forcibly expressed had a synergistic differentiation induction effect (advantageous effect) as compared to the pluripotent stem cells in which the expression amount of the POU5F1 protein had been reduced and the pluripotent stem cells in which the demethylase was forcibly expressed.

Example 6

(Examples of Differentiation into Desired Cell Types Using Pluripotent Stem Cells of the Present Disclosure)

In this Example, differentiation into various desired cell types was confirmed using pluripotent stem cells in which the expression amount of the POU5F1 protein had been substantially removed or reduced on the basis of the example described as Example 3.

(Differentiation into Skeletal Muscle Cells)

During 4-day culture, human pluripotent stem cells were co-transfected with siPOU5F1 and a MYOD1 gene (SEQ ID NO: 33, SEQ ID NO: 34) once, and then transfected with the MYOD1 gene three times. It was confirmed that the cells were differentiated into skeletal muscle cells through the 4-day culture.

(Differentiation into Hepatocytes)

During 12-day culture, human pluripotent stem cells were co-transfected with siPOU5F1 and a HNF1A gene (SEQ ID NO: 35, SEQ ID NO: 36) once, and then transfected with the HNF1A gene twice. It was confirmed that the cells were differentiated into hepatocytes through the 12-day culture.

(Differentiation into Neurons)

During 5-day culture, human pluripotent stem cells are transfected with siPOU5F1 once, and then transfected with a NEUROG1 gene (SEQ ID NO: 37, SEQ ID NO: 38), a NEUROG2 gene (SEQ ID NO: 39, SEQ ID NO: 40), a NEUROG3 gene (SEQ ID NO: 41, SEQ ID NO: 42), a NEUROD1 gene (SEQ ID NO: 43, SEQ ID NO: 44), and a NEUROD2 gene (SEQ ID NO: 45, SEQ ID NO: 46) three times. The cells can be differentiated into neurons through the 5-day culture.

Example 7

(Examples of Differentiation into Desired Cell Types Using Pluripotent Stem Cells of the Present Disclosure by Use of Sendai Virus Vector)

In this Example, unlike Example 3, differentiation into various desired cell types is confirmed using pluripotent stem cells in which the expression amount of the POU5F1 protein has been substantially removed or reduced, through use of a Sendai virus vector instead of synthetic modified mRNA.

(Differentiation into Skeletal Muscle Cells)

A Sendai virus vector known per se (which is active at 33° C. and is inactivated at 37° C.) into which a transcription factor MYOD1 gene (SEQ ID NO: 33, SEQ ID NO: 34) has been cloned is used.

A suspension of human ES cells or iPS cells is infected with the Sendai virus vector at a multiplicity of infection (MOI) of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, skeletal muscle cells can be observed as differentiated cells.

(Differentiation into Hepatocytes)

A Sendai virus vector known per se into which a transcription factor HNF1A gene (SEQ ID NO: 35, SEQ ID NO: 36) has been cloned is used.

A suspension of human ES cells or iPS cells is infected with the Sendai virus vector at a MOI of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, hepatocytes can be observed as differentiated cells.

(Differentiation into Neurons)

A Sendai virus vector known per se into which a transcription factor NEUROG3 gene (SEQ ID NO: 41, SEQ ID NO: 42) has been cloned is used.

A suspension of human ES cells or iPS cells is infected with the Sendai virus vector at a MOI of 1 to 100 (25). After that, the cells are transferred to a culture plate, and the cells are cultured in a $CO_2$ incubator kept at 33° C. for 3 days. After that, the cells are transferred to a $CO_2$ incubator at 37° C., and culture is continued. As a result, neurons (motor neurons) can be observed as differentiated cells.

CONCLUSION

The inventors of the present invention have confirmed by the above-mentioned Examples that the method of differentiating a pluripotent stem cell into a desired cell type with high efficiency and the differentiation induction kit for differentiating a pluripotent stem cell into a desired cell type with high efficiency of the present invention each have at least any one of the following effects.

(1) The period of time required for cell differentiation starting with the pluripotent stem cell is shortened and/or the differentiation induction efficiency is improved.

(2) As modified synthetic mRNA for a gene is used to introduce the gene into the pluripotent stem cell, the introduced gene is not incorporated into the genome of the pluripotent stem cell, with the result that there is no risk of cancellation or the like after cell differentiation induction.

(3) In the introduction of the gene into the pluripotent stem cell using the modified synthetic mRNA, the timing and number of times of the addition of the mRNA for the gene can be easily changed, and hence optimal conditions specific to each of various desired cell types can be selected so as to differentiate the pluripotent stem cell into the desired cell types.

(4) A method of reducing undifferentiated state maintenance of a pluripotent stem cell and a method of reducing differentiation resistance thereof are combined with each other to shorten the period of time required for cell differentiation starting with the pluripotent stem cell and to improve the differentiation induction efficiency in a synergistic manner.

INDUSTRIAL APPLICABILITY

According to the present invention, the novel method of differentiating a pluripotent stem cell into a desired cell type with high efficiency can be provided.

The invention claimed is:

1. A method of differentiating a pluripotent stem cell into a desired cell type, comprising any one of the following steps (1) to (2):

(1) a step of adding an siRNA, shRNA, or antisense RNA having an action of substantially removing or reducing an expression amount of a POU5F1 protein, a demethylase gene, and a modified mRNA encoding a transcription factor required for induction of differentiation into the desired cell type to a pluripotent stem cell; and (2) a step of adding a modified mRNA encoding a transcription factor required for induction of differentiation into the desired cell type and an siRNA, shRNA, or antisense RNA having an action of substantially removing or reducing an expression amount of a POU5F1 protein to a pluripotent stem cell which has a histone in which H3K27me3 modification has been substantially removed or reduced, wherein the differentiation method is of the pluripotent stem cell into a skeletal muscle cell, and the transcription factor of each of the steps (1) to (2) comprises MYOD1, and the removing or reducing of the expression amount of the POU5F1 protein of each of the steps (1) to (2), and production of MYOD1 protein of each of the steps (1) to (2) lead to the differentiation of the pluripotent stem cell and expression of markers of skeletal muscle differentiation.

2. The differentiation method according to claim 1, wherein the pluripotent stem cell is co-transfected with siPOU5F1 and synRNA for MYOD1.

* * * * *

SEQUENCE LISTING

```
<160> NUMBER OF SEQ ID NOS: 46

<210> SEQ ID NO 1
<211> LENGTH: 360
```

```
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360


<210> SEQ ID NO 2
<211> LENGTH: 1083
<212> TYPE: DNA
<213> ORGANISM: Homo sapiens
```

<400> SEQUENCE: 2
atggcgggac acctggcttc ggatttcgcc ttctcgcccc ctccaggtgg tggaggtgat 60
gggccagggg ggccggagcc gggctgggtt gatcctcgga cctggctaag cttccaaggc 120
cctcctggag ggccaggaat cgggccgggg gttgggccag gctctgaggt gtgggggatt 180
cccccatgcc ccccgccgta tgagttctgt ggggggatgg cgtactgtgg gccccaggtt 240
ggagtggggc tagtgcccca aggcggcttg gagacctctc agcctgaggg cgaagcagga 300
gtcggggtgg agagcaactc cgatggggcc tccccggagc cctgcaccgt cacccctggt 360
gccgtgaagc tggagaagga gaagctggag caaaacccgg aggagtccca ggacatcaaa 420
gctctgcaga aagaactcga gcaatttgcc aagctcctga agcagaagag gatcaccctg 480
ggatatacac aggccgatgt ggggctcacc ctgggggttc tatttgggaa ggtattcagc 540
caaacgacca tctgccgctt tgaggctctg cagcttagct tcaagaacat gtgtaagctg 600
cggcccttgc tgcagaagtg ggtggaggaa gctgacaaca atgaaaatct tcaggagata 660
tgcaaagcag aaaccctcgt gcaggcccga aagagaaagc gaaccagtat cgagaaccga 720
gtgagaggca acctggagaa tttgttcctg cagtgcccga aacccacact gcagcagatc 780
agccacatcg cccagcagct tgggctcgag aaggatgtgg tccgagtgtg gttctgtaac 840
cggcgccaga agggcaagcg atcaagcagc gactatgcac aacgagagga ttttgaggct 900
gctgggtctc ctttctcagg gggaccagtg tcctttcctc tggccccagg gccccatttt 960
ggtaccccag gctatgggag ccctcacttc actgcactgt actcctcggt ccctttccct 1020
gagggggaag cctttccccc tgtctccgtc accactctgg gctctcccat gcattcaaac 1080
tga 1083

<210> SEQ ID NO 3
<211> LENGTH: 1682
<212> TYPE: PRT
<213> ORGANISM: Homo sapiens

<400> SEQUENCE: 3

Met His Arg Ala Val Asp Pro Pro Gly Ala Arg Ala Ala Arg Glu Ala
1 5 10 15

Phe Ala Leu Gly Gly Leu Ser Cys Ala Gly Ala Trp Ser Ser Cys Pro
20 25 30

Pro His Pro Pro Pro Arg Ser Ala Trp Leu Pro Gly Gly Arg Cys Ser
35 40 45

Ala Ser Ile Gly Gln Pro Pro Leu Pro Ala Pro Leu Pro Pro Ser His
50 55 60

Gly Ser Ser Ser Gly His Pro Ser Lys Pro Tyr Tyr Ala Pro Gly Ala
65 70 75 80

Pro Thr Pro Arg Pro Leu His Gly Lys Leu Glu Ser Leu His Gly Cys
85 90 95

Val Gln Ala Leu Leu Arg Glu Pro Ala Gln Pro Gly Leu Trp Glu Gln
100 105 110

Leu Gly Gln Leu Tyr Glu Ser Glu His Asp Ser Glu Glu Ala Thr Arg
115 120 125

Cys Tyr His Ser Ala Leu Arg Tyr Gly Gly Ser Phe Ala Glu Leu Gly
130 135 140

Pro Arg Ile Gly Arg Leu Gln Gln Ala Gln Leu Trp Asn Phe His Thr
145 150 155 160

-continued

```
Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Pro Leu Pro Pro Pro Pro Pro
                245                 250                 255

Pro Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
        275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

Arg Met Asp Ser Ser Val Ser Pro Ala Ala Thr Thr Ala Cys Val Pro
    370                 375                 380

Tyr Ala Pro Ser Arg Pro Pro Gly Leu Pro Gly Thr Thr Thr Ser Ser
385                 390                 395                 400

Ser Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445

Phe Leu Gly Ala Pro Ala Ala Thr Pro His Leu Ser Leu Pro Pro Gly
    450                 455                 460

Pro Ser Ser Pro Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
                485                 490                 495

Asp Gly Glu Ile Leu Glu Glu Leu Phe Phe Gly Thr Glu Gly Pro Pro
            500                 505                 510

Arg Pro Ala Pro Pro Pro Leu Pro His Arg Glu Gly Phe Leu Gly Pro
        515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Ser Asn Ser Asn Ser Gly Ser
545                 550                 555                 560

His Ser Ser Ser Pro Ala Gly Pro Val Ser Phe Pro Pro Pro Pro Tyr
                565                 570                 575

Leu Ala Arg Ser Ile Asp Pro Leu Pro Arg Pro Pro Ser Pro Ala Gln
```

```
            580                 585                 590

Asn Pro Gln Asp Pro Pro Leu Val Pro Leu Thr Leu Ala Leu Pro Pro
        595                 600                 605

Ala Pro Pro Ser Ser Cys His Gln Asn Thr Ser Gly Ser Phe Arg Arg
    610                 615                 620

Pro Glu Ser Pro Arg Pro Arg Val Ser Phe Pro Lys Thr Pro Glu Val
625                 630                 635                 640

Gly Pro Gly Pro Pro Pro Gly Pro Leu Ser Lys Ala Pro Gln Pro Val
                645                 650                 655

Pro Pro Gly Val Gly Glu Leu Pro Ala Arg Gly Pro Arg Leu Phe Asp
            660                 665                 670

Phe Pro Pro Thr Pro Leu Glu Asp Gln Phe Glu Glu Pro Ala Glu Phe
        675                 680                 685

Lys Ile Leu Pro Asp Gly Leu Ala Asn Ile Met Lys Met Leu Asp Glu
    690                 695                 700

Ser Ile Arg Lys Glu Glu Glu Gln Gln Gln His Glu Ala Gly Val Ala
705                 710                 715                 720

Pro Gln Pro Pro Leu Lys Glu Pro Phe Ala Ser Leu Gln Ser Pro Phe
                725                 730                 735

Pro Thr Asp Thr Ala Pro Thr Thr Thr Ala Pro Ala Val Ala Val Thr
            740                 745                 750

Thr Thr Thr Thr Thr Thr Thr Thr Thr Thr Ala Thr Gln Glu Glu Glu
        755                 760                 765

Lys Lys Pro Pro Pro Ala Leu Pro Pro Pro Pro Pro Leu Ala Lys Phe
    770                 775                 780

Pro Pro Pro Ser Gln Pro Gln Pro Pro Pro Pro Pro Pro Pro Ser Pro
785                 790                 795                 800

Ala Ser Leu Leu Lys Ser Leu Ala Ser Val Leu Glu Gly Gln Lys Tyr
                805                 810                 815

Cys Tyr Arg Gly Thr Gly Ala Ala Val Ser Thr Arg Pro Gly Pro Leu
            820                 825                 830

Pro Thr Thr Gln Tyr Ser Pro Gly Pro Pro Ser Gly Ala Thr Ala Leu
        835                 840                 845

Pro Pro Thr Ser Ala Ala Pro Ser Ala Gln Gly Ser Pro Gln Pro Ser
    850                 855                 860

Ala Ser Ser Ser Ser Gln Phe Ser Thr Ser Gly Gly Pro Trp Ala Arg
865                 870                 875                 880

Glu Arg Arg Ala Gly Glu Glu Pro Val Pro Gly Pro Met Thr Pro Thr
                885                 890                 895

Gln Pro Pro Pro Pro Leu Ser Leu Pro Pro Ala Arg Ser Glu Ser Glu
            900                 905                 910

Val Leu Glu Glu Ile Ser Arg Ala Cys Glu Thr Leu Val Glu Arg Val
        915                 920                 925

Gly Arg Ser Ala Thr Asp Pro Ala Asp Pro Val Asp Thr Ala Glu Pro
    930                 935                 940

Ala Asp Ser Gly Thr Glu Arg Leu Leu Pro Pro Ala Gln Ala Lys Glu
945                 950                 955                 960

Glu Ala Gly Gly Val Ala Ala Val Ser Gly Ser Cys Lys Arg Arg Gln
                965                 970                 975

Lys Glu His Gln Lys Glu His Arg Arg His Arg Arg Ala Cys Lys Asp
            980                 985                 990

Ser Val Gly Arg Arg Pro Arg Glu  Gly Arg Ala Lys Ala  Lys Ala Lys
        995                 1000                1005
```

```
Val Pro  Lys Glu Lys Ser Arg  Arg Val Leu Gly Asn  Leu Asp Leu
    1010                 1015                 1020

Gln Ser  Glu Glu Ile Gln Gly  Arg Glu Lys Ser Arg  Pro Asp Leu
    1025                 1030                 1035

Gly Gly  Ala Ser Lys Ala Lys  Pro Pro Thr Ala Pro  Ala Pro Pro
    1040                 1045                 1050

Ser Ala  Pro Ala Pro Ser Ala  Gln Pro Thr Pro Pro  Ser Ala Ser
    1055                 1060                 1065

Val Pro  Gly Lys Lys Ala Arg  Glu Glu Ala Pro Gly  Pro Pro Gly
    1070                 1075                 1080

Val Ser  Arg Ala Asp Met Leu  Lys Leu Arg Ser Leu  Ser Glu Gly
    1085                 1090                 1095

Pro Pro  Lys Glu Leu Lys Ile  Arg Leu Ile Lys Val  Glu Ser Gly
    1100                 1105                 1110

Asp Lys  Glu Thr Phe Ile Ala  Ser Glu Val Glu Glu  Arg Arg Leu
    1115                 1120                 1125

Arg Met  Ala Asp Leu Thr Ile  Ser His Cys Ala Ala  Asp Val Val
    1130                 1135                 1140

Arg Ala  Ser Arg Asn Ala Lys  Val Lys Gly Lys Phe  Arg Glu Ser
    1145                 1150                 1155

Tyr Leu  Ser Pro Ala Gln Ser  Val Lys Pro Lys Ile  Asn Thr Glu
    1160                 1165                 1170

Glu Lys  Leu Pro Arg Glu Lys  Leu Asn Pro Pro Thr  Pro Ser Ile
    1175                 1180                 1185

Tyr Leu  Glu Ser Lys Arg Asp  Ala Phe Ser Pro Val  Leu Leu Gln
    1190                 1195                 1200

Phe Cys  Thr Asp Pro Arg Asn  Pro Ile Thr Val Ile  Arg Gly Leu
    1205                 1210                 1215

Ala Gly  Ser Leu Arg Leu Asn  Leu Gly Leu Phe Ser  Thr Lys Thr
    1220                 1225                 1230

Leu Val  Glu Ala Ser Gly Glu  His Thr Val Glu Val  Arg Thr Gln
    1235                 1240                 1245

Val Gln  Gln Pro Ser Asp Glu  Asn Trp Asp Leu Thr  Gly Thr Arg
    1250                 1255                 1260

Gln Ile  Trp Pro Cys Glu Ser  Ser Arg Ser His Thr  Thr Ile Ala
    1265                 1270                 1275

Lys Tyr  Ala Gln Tyr Gln Ala  Ser Ser Phe Gln Glu  Ser Leu Gln
    1280                 1285                 1290

Glu Glu  Lys Glu Ser Glu Asp  Glu Glu Ser Glu Glu  Pro Asp Ser
    1295                 1300                 1305

Thr Thr  Gly Thr Pro Pro Ser  Ser Ala Pro Asp Pro  Lys Asn His
    1310                 1315                 1320

His Ile  Ile Lys Phe Gly Thr  Asn Ile Asp Leu Ser  Asp Ala Lys
    1325                 1330                 1335

Arg Trp  Lys Pro Gln Leu Gln  Glu Leu Leu Lys Leu  Pro Ala Phe
    1340                 1345                 1350

Met Arg  Val Thr Ser Thr Gly  Asn Met Leu Ser His  Val Gly His
    1355                 1360                 1365

Thr Ile  Leu Gly Met Asn Thr  Val Gln Leu Tyr Met  Lys Val Pro
    1370                 1375                 1380

Gly Ser  Arg Thr Pro Gly His  Gln Glu Asn Asn Asn  Phe Cys Ser
    1385                 1390                 1395
```

```
Val Asn  Ile Asn Ile Gly Pro  Gly Asp Cys Glu Trp  Phe Ala Val
    1400                 1405                 1410

His Glu  His Tyr Trp Glu Thr  Ile Ser Ala Phe Cys  Asp Arg His
    1415                 1420                 1425

Gly Val  Asp Tyr Leu Thr Gly  Ser Trp Trp Pro Ile  Leu Asp Asp
    1430                 1435                 1440

Leu Tyr  Ala Ser Asn Ile Pro  Val Tyr Arg Phe Val  Gln Arg Pro
    1445                 1450                 1455

Gly Asp  Leu Val Trp Ile Asn  Ala Gly Thr Val His  Trp Val Gln
    1460                 1465                 1470

Ala Thr  Gly Trp Cys Asn Asn  Ile Ala Trp Asn Val  Gly Pro Leu
    1475                 1480                 1485

Thr Ala  Tyr Gln Tyr Gln Leu  Ala Leu Glu Arg Tyr  Glu Trp Asn
    1490                 1495                 1500

Glu Val  Lys Asn Val Lys Ser  Ile Val Pro Met Ile  His Val Ser
    1505                 1510                 1515

Trp Asn  Val Ala Arg Thr Val  Lys Ile Ser Asp Pro  Asp Leu Phe
    1520                 1525                 1530

Lys Met  Ile Lys Phe Cys Leu  Leu Gln Ser Met Lys  His Cys Gln
    1535                 1540                 1545

Val Gln  Arg Glu Ser Leu Val  Arg Ala Gly Lys Lys  Ile Ala Tyr
    1550                 1555                 1560

Gln Gly  Arg Val Lys Asp Glu  Pro Ala Tyr Tyr Cys  Asn Glu Cys
    1565                 1570                 1575

Asp Val  Glu Val Phe Asn Ile  Leu Phe Val Thr Ser  Glu Asn Gly
    1580                 1585                 1590

Ser Arg  Asn Thr Tyr Leu Val  His Cys Glu Gly Cys  Ala Arg Arg
    1595                 1600                 1605

Arg Ser  Ala Gly Leu Gln Gly  Val Val Val Leu Glu  Gln Tyr Arg
    1610                 1615                 1620

Thr Glu  Glu Leu Ala Gln Ala  Tyr Asp Ala Phe Thr  Leu Val Arg
    1625                 1630                 1635

Ala Arg  Arg Ala Arg Gly Gln  Arg Arg Arg Ala Leu  Gly Gln Ala
    1640                 1645                 1650

Ala Gly  Thr Gly Phe Gly Ser  Pro Ala Ala Pro Phe  Pro Glu Pro
    1655                 1660                 1665

Pro Pro  Ala Phe Ser Pro Gln  Ala Pro Ala Ser Thr  Ser Arg
    1670                 1675                 1680


<210> SEQ ID NO 4
<211> LENGTH: 659
<212> TYPE: PRT
<213> ORGANISM: Homo sapiens

<400> SEQUENCE: 4

Gln Ser Glu Glu Ile Gln Gly Arg Glu Lys Ser Arg Pro Asp Leu Gly
1               5                   10                  15

Gly Ala Ser Lys Ala Lys Pro Pro Thr Ala Pro Ala Pro Pro Ser Ala
            20                  25                  30

Pro Ala Pro Ser Ala Gln Pro Thr Pro Pro Ser Ala Ser Val Pro Gly
        35                  40                  45

Lys Lys Ala Arg Glu Glu Ala Pro Gly Pro Pro Gly Val Ser Arg Ala
    50                  55                  60

Asp Met Leu Lys Leu Arg Ser Leu Ser Glu Gly Pro Pro Lys Glu Leu
65                  70                  75                  80
```

-continued

```
Lys Ile Arg Leu Ile Lys Val Glu Ser Gly Asp Lys Glu Thr Phe Ile
                85                  90                  95

Ala Ser Glu Val Glu Glu Arg Arg Leu Arg Met Ala Asp Leu Thr Ile
            100                 105                 110

Ser His Cys Ala Ala Asp Val Val Arg Ala Ser Arg Asn Ala Lys Val
        115                 120                 125

Lys Gly Lys Phe Arg Glu Ser Tyr Leu Ser Pro Ala Gln Ser Val Lys
    130                 135                 140

Pro Lys Ile Asn Thr Glu Glu Lys Leu Pro Arg Glu Lys Leu Asn Pro
145                 150                 155                 160

Pro Thr Pro Ser Ile Tyr Leu Glu Ser Lys Arg Asp Ala Phe Ser Pro
                165                 170                 175

Val Leu Leu Gln Phe Cys Thr Asp Pro Arg Asn Pro Ile Thr Val Ile
            180                 185                 190

Arg Gly Leu Ala Gly Ser Leu Arg Leu Asn Leu Gly Leu Phe Ser Thr
        195                 200                 205

Lys Thr Leu Val Glu Ala Ser Gly Glu His Thr Val Glu Val Arg Thr
    210                 215                 220

Gln Val Gln Gln Pro Ser Asp Glu Asn Trp Asp Leu Thr Gly Thr Arg
225                 230                 235                 240

Gln Ile Trp Pro Cys Glu Ser Ser Arg Ser His Thr Thr Ile Ala Lys
                245                 250                 255

Tyr Ala Gln Tyr Gln Ala Ser Ser Phe Gln Glu Ser Leu Gln Glu Glu
            260                 265                 270

Lys Glu Ser Glu Asp Glu Glu Ser Glu Glu Pro Asp Ser Thr Thr Gly
        275                 280                 285

Thr Pro Pro Ser Ser Ala Pro Asp Pro Lys Asn His His Ile Ile Lys
    290                 295                 300

Phe Gly Thr Asn Ile Asp Leu Ser Asp Ala Lys Arg Trp Lys Pro Gln
305                 310                 315                 320

Leu Gln Glu Leu Leu Lys Leu Pro Ala Phe Met Arg Val Thr Ser Thr
                325                 330                 335

Gly Asn Met Leu Ser His Val Gly His Thr Ile Leu Gly Met Asn Thr
            340                 345                 350

Val Gln Leu Tyr Met Lys Val Pro Gly Ser Arg Thr Pro Gly His Gln
        355                 360                 365

Glu Asn Asn Asn Phe Cys Ser Val Asn Ile Asn Ile Gly Pro Gly Asp
    370                 375                 380

Cys Glu Trp Phe Ala Val His Glu His Tyr Trp Glu Thr Ile Ser Ala
385                 390                 395                 400

Phe Cys Asp Arg His Gly Val Asp Tyr Leu Thr Gly Ser Trp Trp Pro
                405                 410                 415

Ile Leu Asp Asp Leu Tyr Ala Ser Asn Ile Pro Val Tyr Arg Phe Val
            420                 425                 430

Gln Arg Pro Gly Asp Leu Val Trp Ile Asn Ala Gly Thr Val His Trp
        435                 440                 445

Val Gln Ala Thr Gly Trp Cys Asn Asn Ile Ala Trp Asn Val Gly Pro
    450                 455                 460

Leu Thr Ala Tyr Gln Tyr Gln Leu Ala Leu Glu Arg Tyr Glu Trp Asn
465                 470                 475                 480

Glu Val Lys Asn Val Lys Ser Ile Val Pro Met Ile His Val Ser Trp
                485                 490                 495
```

-continued

```
Asn Val Ala Arg Thr Val Lys Ile Ser Asp Pro Asp Leu Phe Lys Met
            500                 505                 510

Ile Lys Phe Cys Leu Leu Gln Ser Met Lys His Cys Gln Val Gln Arg
        515                 520                 525

Glu Ser Leu Val Arg Ala Gly Lys Lys Ile Ala Tyr Gln Gly Arg Val
    530                 535                 540

Lys Asp Glu Pro Ala Tyr Tyr Cys Asn Glu Cys Asp Val Glu Val Phe
545                 550                 555                 560

Asn Ile Leu Phe Val Thr Ser Glu Asn Gly Ser Arg Asn Thr Tyr Leu
                565                 570                 575

Val His Cys Glu Gly Cys Ala Arg Arg Arg Ser Ala Gly Leu Gln Gly
            580                 585                 590

Val Val Val Leu Glu Gln Tyr Arg Thr Glu Glu Leu Ala Gln Ala Tyr
        595                 600                 605

Asp Ala Phe Thr Leu Val Arg Ala Arg Arg Ala Arg Gly Gln Arg Arg
    610                 615                 620

Arg Ala Leu Gly Gln Ala Ala Gly Thr Gly Phe Gly Ser Pro Ala Ala
625                 630                 635                 640

Pro Phe Pro Glu Pro Pro Pro Ala Phe Ser Pro Gln Ala Pro Ala Ser
                645                 650                 655

Thr Ser Arg


<210> SEQ ID NO 5
<211> LENGTH: 109
<212> TYPE: PRT
<213> ORGANISM: Homo sapiens

<400> SEQUENCE: 5

Gln Leu Tyr Met Lys Val Pro Gly Ser Arg Thr Pro Gly His Gln Glu
1               5                   10                  15

Asn Asn Asn Phe Cys Ser Val Asn Ile Asn Ile Gly Pro Gly Asp Cys
            20                  25                  30

Glu Trp Phe Ala Val His Glu His Tyr Trp Glu Thr Ile Ser Ala Phe
        35                  40                  45

Cys Asp Arg His Gly Val Asp Tyr Leu Thr Gly Ser Trp Trp Pro Ile
    50                  55                  60

Leu Asp Asp Leu Tyr Ala Ser Asn Ile Pro Val Tyr Arg Phe Val Gln
65                  70                  75                  80

Arg Pro Gly Asp Leu Val Trp Ile Asn Ala Gly Thr Val His Trp Val
                85                  90                  95

Gln Ala Thr Gly Trp Cys Asn Asn Ile Ala Trp Asn Val
            100                 105


<210> SEQ ID NO 6
<211> LENGTH: 5049
<212> TYPE: DNA
<213> ORGANISM: Homo sapiens

<400> SEQUENCE: 6

atgcatcggg cagtggatcc tccaggggcc cgcgctgcac gggaagcctt tgcccttggg      60

ggcctgagct gtgctggggc ctggagctcc tgcccgcctc atcccccctcc tcgtagcgca     120

tggctgcctg gaggcagatg ctcagccagc attgggcagc cccgcttcc tgctccccta     180

ccccttcac atggcagtag ttctgggcac cccagcaaac catattatgc tccaggggcg     240

cccactccaa gacccctcca tgggaagctg gaatccctgc atggctgtgt gcaggcattg     300
```

```
ctccgggagc cagcccagcc agggctttgg gaacagcttg ggcaactgta cgagtcagag    360
cacgatagtg aggaggccac acgctgctac cacagcgccc ttcgatacgg aggaagcttc    420
gctgagctgg ggccccgcat tggccgactg cagcaggccc agctctggaa ctttcatact    480
ggctcctgcc agcaccgagc caaggtcctg cccccactgg agcaagtgtg gaacttgcta    540
caccttgagc acaaacggaa ctatggagcc aagcggggag gtcccccggt gaagcgagct    600
gctgaacccc cagtggtgca gcctgtgcct cctgcagcac tctcaggccc ctcaggggag    660
gagggcctca gccctggagg caagcgaagg agaggctgca actctgaaca gactggcctt    720
cccccagggc tgccactgcc tccaccacca ttaccaccac caccaccacc accaccacca    780
ccaccaccac ccctgcctgg cctggctacc agccccccat ttcagctaac caagccaggg    840
ctgtggagta ccctgcatgg agatgcctgg ggcccagagc gcaagggttc agcaccccca    900
gagcgccagg agcagcggca ctcgctgcct cacccatatc catacccagc tccagcgtac    960
accgcgcacc cccctggcca ccggctggtc ccggctgctc ccccaggccc aggcccccgc   1020
cccccaggag cagagagcca tggctgcctg cctgccaccc gtccccccgg aagtgacctt   1080
agagagagca gagttcagag gtcgcggatg gactccagcg tttcaccagc agcaaccacc   1140
gcctgcgtgc cttacgcccc ttcccggccc cctggcctcc ccggcaccac caccagcagc   1200
agcagtagca gcagcagcaa cactggtctc cggggcgtgg agccgaaccc aggcattccc   1260
ggcgctgacc attaccaaac tcccgcgctg gaggtctctc accatggccg cctggggccc   1320
tcggcacaca gcagtcggaa accgttcttg gggggctcccg ctgccactcc ccacctatcc   1380
ctgccacctg gaccttcctc accccctcca ccccccctgtc cccgcctctt acgcccccca   1440
ccacccccctg cctggttgaa gggtccggcc tgccgggcag cccgagagga tggagagatc   1500
ttagaagagc tcttctttgg gactgaggga cccccccgcc ctgccccacc acccctcccc   1560
catcgcgagg gcttcttggg gcctccggcc tcccgctttt ctgtgggcac tcaggattct   1620
cacacccctc ccactccccc aaccccaacc accagcagta gcaacagcaa cagtggcagc   1680
cacagcagca gccctgctgg gcctgtgtcc tttcccccac caccctatct ggccagaagt   1740
atagaccccc ttccccggcc tcccagccca gcacagaacc cccaggaccc acctcttgta   1800
cccctgactc ttgccctgcc tccagcccct ccttcctcct gccaccaaaa tacctcagga   1860
agcttcaggc gcccggagag cccccggccc agggtctcct tcccaaagac cccccgaggtg   1920
gggccggggc cacccccagg ccccctgagt aaagcccccc agcctgtgcc gcccggggtt   1980
ggggagctgc ctgcccgagg ccctcgactc tttgattttc cccccactcc gctggaggac   2040
cagtttgagg agccagccga attcaagatc ctacctgatg ggctggccaa catcatgaag   2100
atgctggacg aatccattcg caaggaagag gaacagcaac aacacgaagc aggcgtggcc   2160
ccccaacccc cgctgaagga gcccttgca tctctgcagt ctcctttccc caccgacaca   2220
gcccccacca ctactgctcc tgctgtcgcc gtcaccacca ccaccaccac caccaccacc   2280
accacggcca cccaggaaga ggagaagaag ccaccaccag ccctaccacc accaccgcct   2340
ctagccaagt tccctccacc ctctcagcca cagccaccac cacccccacc ccccagcccg   2400
gccagcctgc tcaaatcctt ggcctccgtg ctggagggac aaaagtactg ttatcggggg   2460
actggagcag ctgtttccac ccggcctggg cccttgccca ccactcagta ttcccctggc   2520
cccccatcag gtgctaccgc cctgccgccc acctcagcgg cccctagcgc ccagggctcc   2580
ccacagccct ctgcttcctc gtcatctcag ttctctacct caggcgggcc ctgggcccgg   2640
gagcgcaggg cgggcgaaga gccagtcccg ggccccatga cccccaccca accgccccca   2700
```

```
cccctatctc tgccccctgc tcgctctgag tctgaggtgc tagaagagat cagccgggct   2760
tgcgagaccc ttgtggagcg ggtgggccgg agtgccactg acccagccga cccagtggac   2820
acagcagagc cagcggacag tgggactgag cgactgctgc cccccgcaca ggccaaggag   2880
gaggctggcg gggtggcggc agtgtcaggc agctgtaagc ggcgacagaa ggagcatcag   2940
aaggagcatc ggcggcacag gcgggcctgt aaggacagtg tgggtcgtcg gccccgtgag   3000
ggcagggcaa aggccaaggc caaggtcccc aaagaaaaga gccgccgggt gctggggaac   3060
ctggacctgc agagcgagga gatccagggt cgtgagaagt cccggcccga tcttggcggg   3120
gcctccaagg ccaagccacc cacagctcca gcccctccat cagctcctgc accttctgcc   3180
cagcccacac ccccgtcagc ctctgtccct ggaaagaagg ctcgggagga agccccaggg   3240
ccaccgggtg tcagccgggc cgacatgctg aagctgcgct cacttagtga ggggcccccc   3300
aaggagctga agatccggct catcaaggta gagagtggtg acaaggagac ctttatcgcc   3360
tctgaggtgg aagagcggcg gctgcgcatg gcagacctca ccatcagcca ctgtgctgct   3420
gacgtcgtgc gcgccagcag gaatgccaag gtgaaaggga agtttcgaga gtcctacctt   3480
tcccctgccc agtctgtgaa accgaagatc aacactgagg agaagctgcc ccgggaaaaa   3540
ctcaaccccc ctacacccag catctatctg gagagcaaac gggatgcctt ctcacctgtc   3600
ctgctgcagt tctgtacaga ccctcgaaat cccatcacag tgatccgggg cctggcgggc   3660
tccctgcggc tcaacttggg cctcttctcc accaagaccc tggtggaagc gagtggcgaa   3720
cacaccgtgg aagttcgcac ccaggtgcag cagccctcag atgagaactg ggatctgaca   3780
ggcactcggc agatctggcc ttgtgagagc tcccgttccc acaccaccat tgccaagtac   3840
gcacagtacc aggcctcatc cttccaggag tctctgcagg aggagaagga gagtgaggat   3900
gaggagtcag aggagccaga cagcaccact ggaacccctc ctagcagcgc accagacccg   3960
aagaaccatc acatcatcaa gtttggcacc aacatcgact tgtctgatgc taagcggtgg   4020
aagccccagc tgcaggagct gctgaagctg cccgccttca tgcgggtaac atccacgggc   4080
aacatgctga gccacgtggg ccacaccatc ctgggcatga acacggtgca gctgtacatg   4140
aaggtgcccg gcagccgaac gccaggccac caggagaata acaacttctg ctccgtcaac   4200
atcaacattg gcccaggcga ctgcgagtgg ttcgcggtgc acgagcacta ctgggagacc   4260
atcagcgctt tctgtgatcg gcacggcgtg gactacttga cgggttcctg gtggccaatc   4320
ctggatgatc tctatgcatc caatattcct gtgtaccgct tcgtgcagcg acccggagac   4380
ctcgtgtgga ttaatgcggg gactgtgcac tgggtgcagg ccaccggctg gtgcaacaac   4440
attgcctgga acgtggggcc cctcaccgcc tatcagtacc agctggccct ggaacgatac   4500
gagtggaatg aggtgaagaa cgtcaaatcc atcgtgccca tgattcacgt gtcatggaac   4560
gtggctcgca cggtcaaaat cagcgacccc gacttgttca agatgatcaa gttctgcctg   4620
ctgcagtcca tgaagcactg ccaggtgcaa cgcgagagcc tggtgcgggc agggaagaaa   4680
atcgcttacc agggccgtgt caaggacgag ccagcctact actgcaacga gtgcgatgtg   4740
gaggtgttta acatcctgtt cgtgacaagt gagaatggca gccgcaacac gtacctggta   4800
cactgcgagg gctgtgcccg gcgccgcagc gcaggcctgc agggcgtggt ggtgctggag   4860
cagtaccgca ctgaggagct ggctcaggcc tacgacgcct tcacgctggt gagggcccgg   4920
cgggcgcgcg ggcagcggag gagggcactg ggcaggctgg cagggacggg cttcgggagc   4980
ccggccgcgc ctttccctga gccccccgccg gctttctccc cccaggcccc agccagcacg   5040
```

tcgcgatga 5049

<210> SEQ ID NO 7
<211> LENGTH: 1980
<212> TYPE: DNA
<213> ORGANISM: Homo sapiens

<400> SEQUENCE: 7
cagagcgagg agatccaggg tcgtgagaag tcccggcccg atcttggcgg ggcctccaag 60
gccaagccac ccacagctcc agcccctcca tcagctcctg caccttctgc ccagcccaca 120
cccccgtcag cctctgtccc tggaaagaag gctcgggagg aagccccagg gccaccgggt 180
gtcagccggg ccgacatgct gaagctgcgc tcacttagtg aggggccccc caaggagctg 240
aagatccggc tcatcaaggt agagagtggt gacaaggaga cctttatcgc ctctgaggtg 300
gaagagcggc ggctgcgcat ggcagacctc accatcagcc actgtgctgc tgacgtcgtg 360
cgcgccagca ggaatgccaa ggtgaaaggg aagtttcgag agtcctacct ttcccctgcc 420
cagtctgtga aaccgaagat caacactgag gagaagctgc cccgggaaaa actcaacccc 480
cctacaccca gcatctatct ggagagcaaa cgggatgcct tctcacctgt cctgctgcag 540
ttctgtacag accctcgaaa tcccatcaca gtgatccggg gcctggcggg ctccctgcgg 600
ctcaacttgg gcctcttctc caccaagacc ctggtggaag cgagtggcga acacaccgtg 660
gaagttcgca cccaggtgca gcagccctca gatgagaact gggatctgac aggcactcgg 720
cagatctggc cttgtgagag ctcccgttcc cacaccacca ttgccaagta cgcacagtac 780
caggcctcat ccttccagga gtctctgcag gaggagaagg agagtgagga tgaggagtca 840
gaggagccag acagcaccac tggaacccct cctagcagcg caccagaccc gaagaaccat 900
cacatcatca agtttggcac caacatcgac ttgtctgatg ctaagcggtg gaagccccag 960
ctgcaggagc tgctgaagct gcccgccttc atgcgggtaa catccacggg caacatgctg 1020
agccacgtgg gccacaccat cctgggcatg aacacggtgc agctgtacat gaaggtgccc 1080
ggcagccgaa cgccaggcca ccaggagaat aacaacttct gctccgtcaa catcaacatt 1140
ggcccaggcg actgcgagtg gttcgcggtg cacgagcact actgggagac catcagcgct 1200
ttctgtgatc ggcacggcgt ggactacttg acgggttcct ggtggccaat cctggatgat 1260
ctctatgcat ccaatattcc tgtgtaccgc ttcgtgcagc gacccggaga cctcgtgtgg 1320
attaatgcgg ggactgtgca ctgggtgcag gccaccggct ggtgcaacaa cattgcctgg 1380
aacgtggggc ccctcaccgc ctatcagtac cagctggccc tggaacgata cgagtggaat 1440
gaggtgaaga acgtcaaatc catcgtgccc atgattcacg tgtcatggaa cgtggctcgc 1500
acggtcaaaa tcagcgaccc cgacttgttc aagatgatca agttctgcct gctgcagtcc 1560
atgaagcact gccaggtgca acgcgagagc ctggtgcggg cagggaagaa aatcgcttac 1620
cagggccgtg tcaaggacga gccagcctac tactgcaacg agtgcgatgt ggaggtgttt 1680
aacatcctgt tcgtgacaag tgagaatggc agccgcaaca cgtacctggt acactgcgag 1740
ggctgtgccc ggcgccgcag cgcaggcctg cagggcgtgg tggtgctgga gcagtaccgc 1800
actgaggagc tggctcaggc ctacgacgcc ttcacgctgg tgagggcccg gcgggcgcgc 1860
gggcagcgga ggagggcact ggggcaggct gcagggacgg gcttcgggag cccggccgcg 1920
cctttccctg agcccccgcc ggctttctcc ccccaggccc cagccagcac gtcgcgatga 1980

<210> SEQ ID NO 8
<211> LENGTH: 327

<212> TYPE: DNA
<213> ORGANISM: Homo sapiens

<400> SEQUENCE: 8
cagctgtaca tgaaggtgcc cggcagccga acgccaggcc accaggagaa taacaacttc 60
tgctccgtca acatcaacat tggcccaggc gactgcgagt ggttcgcggt gcacgagcac 120
tactgggaga ccatcagcgc tttctgtgat cggcacggcg tggactactt gacgggttcc 180
tggtggccaa tcctggatga tctctatgca tccaatattc ctgtgtaccg cttcgtgcag 240
cgacccggag acctcgtgtg gattaatgcg gggactgtgc actgggtgca ggccaccggc 300
tggtgcaaca acattgcctg gaacgtg 327

<210> SEQ ID NO 9
<211> LENGTH: 12
<212> TYPE: PRT
<213> ORGANISM: Human immunodeficiency virus

<400> SEQUENCE: 9

Gly Arg Lys Lys Arg Arg Gln Arg Arg Arg Pro Gln
1 5 10

<210> SEQ ID NO 10
<211> LENGTH: 8
<212> TYPE: PRT
<213> ORGANISM: Artificial Sequence
<220> FEATURE:
<223> OTHER INFORMATION: r8

<400> SEQUENCE: 10

Arg Arg Arg Arg Arg Arg Arg Arg
1 5

<210> SEQ ID NO 11
<211> LENGTH: 21
<212> TYPE: PRT
<213> ORGANISM: Artificial Sequence
<220> FEATURE:
<223> OTHER INFORMATION: MPG-8 (The first amino acid "Ala" is modified into "bAla.")

<400> SEQUENCE: 11

Ala Phe Leu Gly Trp Leu Gly Ala Trp Gly Thr Met Gly Trp Ser Pro
1 5 10 15

Lys Lys Lys Arg Lys
20

<210> SEQ ID NO 12
<211> LENGTH: 21
<212> TYPE: DNA
<213> ORGANISM: Artificial Sequence
<220> FEATURE:
<223> OTHER INFORMATION: sense strand of siRNA against POU5F1

<400> SEQUENCE: 12
gcccgaaaga gaaagcgaat t 21

<210> SEQ ID NO 13
<211> LENGTH: 21
<212> TYPE: DNA
<213> ORGANISM: Artificial Sequence
<220> FEATURE:
<223> OTHER INFORMATION: antisense strand of siRNA against POU5F1

<400> SEQUENCE: 13

```
uucgcuuucu cuuucgggcc t                                              21


<210> SEQ ID NO 14
<211> LENGTH: 20
<212> TYPE: DNA
<213> ORGANISM: Artificial Sequence
<220> FEATURE:
<223> OTHER INFORMATION: qRT-PCR forward primer for MYOG

<400> SEQUENCE: 14

gccagactat ccccttcctc                                                20


<210> SEQ ID NO 15
<211> LENGTH: 20
<212> TYPE: DNA
<213> ORGANISM: Artificial Sequence
<220> FEATURE:
<223> OTHER INFORMATION: qRT-PCR reverse primer for MYOG

<400> SEQUENCE: 15

gaggccgcgt tatgataaaa                                                20


<210> SEQ ID NO 16
<211> LENGTH: 18
<212> TYPE: DNA
<213> ORGANISM: Artificial Sequence
<220> FEATURE:
<223> OTHER INFORMATION: qRT-PCR forward primer for AFP

<400> SEQUENCE: 16

tgggacccga actttcca                                                  18


<210> SEQ ID NO 17
<211> LENGTH: 22
<212> TYPE: DNA
<213> ORGANISM: Artificial Sequence
<220> FEATURE:
<223> OTHER INFORMATION: qRT-PCR reverse primer for AFP

<400> SEQUENCE: 17

ggccacatcc aggactagtt tc                                             22


<210> SEQ ID NO 18
<211> LENGTH: 20
<212> TYPE: DNA
<213> ORGANISM: Artificial Sequence
<220> FEATURE:
<223> OTHER INFORMATION: qRT-PCR forward primer for COL1A1

<400> SEQUENCE: 18

cctggatgcc atcaaagtct                                                20


<210> SEQ ID NO 19
<211> LENGTH: 20
<212> TYPE: DNA
<213> ORGANISM: Artificial Sequence
<220> FEATURE:
<223> OTHER INFORMATION: qRT-PCR reverse primer for COL1A1

<400> SEQUENCE: 19

tcttgtcctt ggggttcttg                                                20


<210> SEQ ID NO 20
<211> LENGTH: 20
<212> TYPE: DNA
```

<213> ORGANISM: Artificial Sequence
<220> FEATURE:
<223> OTHER INFORMATION: qRT-PCR forward primer for COL2A1

<400> SEQUENCE: 20
tttcccaggt caagatggtc 20

<210> SEQ ID NO 21
<211> LENGTH: 20
<212> TYPE: DNA
<213> ORGANISM: Artificial Sequence
<220> FEATURE:
<223> OTHER INFORMATION: qRT-PCR reverse primer for COL2A1

<400> SEQUENCE: 21
cttcagcacc tgtctcacca 20

<210> SEQ ID NO 22
<211> LENGTH: 20
<212> TYPE: DNA
<213> ORGANISM: Artificial Sequence
<220> FEATURE:
<223> OTHER INFORMATION: qRT-PCR forward primer for CD45

<400> SEQUENCE: 22
tcctggactc ccaaaatctg 20

<210> SEQ ID NO 23
<211> LENGTH: 20
<212> TYPE: DNA
<213> ORGANISM: Artificial Sequence
<220> FEATURE:
<223> OTHER INFORMATION: qRT-PCR reverse primer for CD45

<400> SEQUENCE: 23
accttgaacc cgaacatgag 20

<210> SEQ ID NO 24
<211> LENGTH: 23
<212> TYPE: DNA
<213> ORGANISM: Artificial Sequence
<220> FEATURE:
<223> OTHER INFORMATION: qRT-PCR forward primer for NESTIN

<400> SEQUENCE: 24
tggttttcca gagtcttcag tga 23

<210> SEQ ID NO 25
<211> LENGTH: 21
<212> TYPE: DNA
<213> ORGANISM: Artificial Sequence
<220> FEATURE:
<223> OTHER INFORMATION: qRT-PCR reverse primer for NESTIN

<400> SEQUENCE: 25
gaaacagcca tagagggcaa a 21

<210> SEQ ID NO 26
<211> LENGTH: 960
<212> TYPE: DNA
<213> ORGANISM: Homo sapiens

<400> SEQUENCE: 26
atggagctac tgtcgccacc gctccgcgac gtagacctga cggcccccga cggctctctc 60
tgctcctttg ccacaacgga cgacttctat gacgacccgt gtttcgactc cccggacctg 120

```
cgcttcttcg aagacctgga cccgcgcctg atgcacgtgg gcgcgctcct gaaacccgaa    180

gagcactcgc acttccccgc ggcggtgcac ccggccccgg gcgcacgtga ggacgagcat    240

gtgcgcgcgc ccagcgggca ccaccaggcg ggccgctgcc tactgtgggc ctgcaaggcg    300

tgcaagcgca agaccaccaa cgccgaccgc cgcaaggccg ccaccatgcg cgagcggcgc    360

cgcctgagca aagtaaatga ggcctttgag acactcaagc gctgcacgtc gagcaatcca    420

aaccagcggt tgcccaaggt ggagatcctg cgcaacgcca tccgctatat cgagggcctg    480

caggctctgc tgcgcgacca ggacgccgcg ccccctggcg ccgcagccgc cttctatgcg    540

ccgggcccgc tgcccccggg ccgcggcggc gagcactaca gcggcgactc cgacgcgtcc    600

agcccgcgct ccaactgctc cgacggcatg atggactaca gcggcccccc gagcggcgcc    660

cggcggcgga actgctacga aggcgcctac tacaacgagg cgcccagcga acccaggccc    720

gggaagagtg cggcggtgtc gagcctagac tgcctgtcca gcatcgtgga gcgcatctcc    780

accgagagcc ctgcggcgcc cgccctcctg ctggcggacg tgccttctga gtcgcctccg    840

cgcaggcaag aggctgccgc ccccagcgag ggagagagca gcggcgaccc cacccagtca    900

ccggacgccg ccccgcagtg ccctgcgggt gcgaacccca acccgatata ccaggtgctc    960
```

<210> SEQ ID NO 27
<211> LENGTH: 1896
<212> TYPE: DNA
<213> ORGANISM: Homo sapiens

<400> SEQUENCE: 27

```
atggtttcta aactgagcca gctgcagacg gagctcctgg cggccctgct ggagtcaggg     60

ctgagcaaag aggcactgct ccaggcactg ggtgagccgg ggccctacct cctggctgga    120

gaaggccccc tggacaaggg ggagtcctgc ggcggcggtc gaggggagct ggctgagctg    180

cccaatgggc tgggggagac tcggggctcc gaggacgaga cggacgacga tggggaagac    240

ttcacgccac ccatcctcaa agagctggag aacctcagcc ctgaggaggc ggcccaccag    300

aaagccgtgg tggagaccct tctgcaggag gacccgtggc gtgtggcgaa gatggtcaag    360

tcctacctgc agcagcacaa catcccacag cgggaggtgg tcgataccac tggcctcaac    420

cagtcccacc tgtcccaaca cctcaacaag ggcactccca tgaagacgca gaagcgggcc    480

gccctgtaca cctggtacgt ccgcaagcag cgagaggtgg cgcagcagtt cacccatgca    540

gggcagggag ggctgattga agagcccaca ggtgatgagc taccaaccaa gaaggggcgg    600

aggaaccgtt tcaagtgggg cccagcatcc cagcagatcc tgttccaggc ctatgagagg    660

cagaagaacc ctagcaagga ggagcgagag acgctagtgg aggagtgcaa tagggcggaa    720

tgcatccaga gaggggtgtc cccatcacag gcacaggggc tgggctccaa cctcgtcacg    780

gaggtgcgtg tctacaactg gtttgccaac cggcgcaaag aagaagcctt ccggcacaag    840

ctggccatgg acacgtacag cgggcccccc ccagggccag gcccgggacc tgcgctgccc    900

gctcacagct cccctggcct gcctccacct gccctctccc ccagtaaggt ccacggtgtg    960

cgctatggac agcctgcgac cagtgagact gcagaagtac cctcaagcag cggcggtccc   1020

ttagtgacag tgtctacacc cctccaccaa gtgtccccca cgggcctgga gcccagccac   1080

agcctgctga gtacagaagc caagctggtc tcagcagctg gggcccccct ccccccctgtc   1140

agcaccctga cagcactgca cagcttggag cagacatccc caggcctcaa ccagcagccc   1200

cagaacctca tcatggcctc acttcctggg gtcatgacca tcgggcctgg tgagcctgcc   1260
```

```
tccctgggtc ctacgttcac caacacaggt gcctccaccc tggtcatcgg cctggcctcc   1320
acgcaggcac agagtgtgcc ggtcatcaac agcatgggca gcagcctgac caccctgcag   1380
cccgtccagt tctcccagcc gctgcacccc tcctaccagc agccgctcat gccacctgtg   1440
cagagccatg tgacccagag ccccttcatg gccaccatgg ctcagctgca gagcccccac   1500
gccctctaca gccacaagcc cgaggtggcc cagtacaccc acacaggcct gctcccgcag   1560
actatgctca tcaccgacac caccaacctg agcgccctgg ccagcctcac gcccaccaag   1620
caggtcttca cctcagacac tgaggcctcc agtgagtccg ggcttcacac gccggcatct   1680
caggccacca ccctccacgt ccccagccag gaccctgccg gcatccagca cctgcagccg   1740
gcccaccggc tcagcgccag ccccacagtg tcctccagca gcctggtgct gtaccagagc   1800
tcagactcca gcaatggcca gagccacctg ctgccatcca accacagcgt catcgagacc   1860
ttcatctcca cccagatggc ctcttcctcc cagttg                             1896
```

<210> SEQ ID NO 28
<211> LENGTH: 1521
<212> TYPE: DNA
<213> ORGANISM: Homo sapiens

<400> SEQUENCE: 28

```
atgcgtattc ccgtagatcc gagcaccagc cggcgcttca gccccccctc cagcagcctg     60
cagcccggca aaatgagcga cgtgagcccg gtggtggctg cgcaacagca gcagcaacag    120
cagcagcagc aacagcagca gcagcagcag caacagcagc agcagcagca ggaggcggcg    180
gcggcggctg cggcggcggc ggcggctgcg gcggcggcag ctgcagtgcc ccggttgcgg    240
ccgccccacg acaaccgcac catggtggag atcatcgccg accacccggc cgaactcgtc    300
cgcaccgaca gccccaactt cctgtgctcg gtgctgccct cgcactggcg ctgcaacaag    360
accctgcccg tggccttcaa ggtggtagcc ctcggagagg taccagatgg gactgtggtt    420
actgtcatgg cgggtaacga tgaaaattat tctgctgagc tccggaatgc ctctgctgtt    480
atgaaaaacc aagtagcaag gttcaacgat ctgagatttg tgggccggag tggacgaggc    540
aagagtttca ccttgaccat aaccgtcttc acaaatcctc cccaagtagc tacctatcac    600
agagcaatta aagttacagt agatggacct cgggaaccca gaaggcacag acagaagctt    660
gatgactcta aacctagttt gttctctgac cgcctcagtg atttagggcg cattcctcat    720
cccagtatga gagtaggtgt cccgcctcag aacccacggc cctccctgaa ctctgcacca    780
agtcctttta atccacaagg acagagtcag attacagacc ccaggcaggc acagtcttcc    840
ccgccgtggt cctatgacca gtcttacccc tcctacctga gccagatgac gtccccgtcc    900
atccactcta ccaccccgct gtcttccaca cggggcactg ggcttcctgc catcaccgat    960
gtgcctaggc gcatttcaga tgatgacact gccacctctg acttctgcct ctggccttcc   1020
actctcagta agaagagcca ggcaggtgct tcagaactgg gcccttttc agaccccagg    1080
cagttcccaa gcatttcatc cctcactgag agccgcttct ccaacccacg aatgcactat   1140
ccagccacct ttacttacac cccgccagtc acctcaggca tgtccctcgg tatgtccgcc   1200
accactcact accacaccta cctgccacca ccctaccccg gctcttccca aagccagagt   1260
ggacccttcc agaccagcag cactccatat ctctactatg gcacttcgtc aggatcctat   1320
cagtttccca tggtgccggg gggagaccgg tctccttcca gaatgcttcc gccatgcacc   1380
accacctcga atggcagcac gctattaaat ccaaatttgc ctaaccagaa tgatggtgtt   1440
gacgctgatg gaagccacag cagttcccca actgttttga attctagtgg cagaatggat   1500
```

gaatctgttt ggcgaccata t 1521

<210> SEQ ID NO 29
<211> LENGTH: 1527
<212> TYPE: DNA
<213> ORGANISM: Homo sapiens

<400> SEQUENCE: 29
atgaatctcc tggacccctt catgaagatg accgacgagc aggagaaggg cctgtccggc 60
gcccccagcc ccaccatgtc cgaggactcc gcgggctcgc cctgcccgtc gggctccggc 120
tcggacaccg agaacacgcg gccccaggag aacacgttcc ccaagggcga gcccgatctg 180
aagaaggaga gcgaggagga caagttcccc gtgtgcatcc gcgaggcggt cagccaggtg 240
ctcaaaggct acgactggac gctggtgccc atgccggtgc gcgtcaacgg ctccagcaag 300
aacaagccgc acgtcaagcg gcccatgaac gccttcatgg tgtgggcgca ggcggcgcgc 360
aggaagctcg cggaccagta cccgcacttg cacaacgccg agctcagcaa gacgctgggc 420
aagctctgga gacttctgaa cgagagcgag aagcggccct tcgtggagga ggcggagcgg 480
ctgcgcgtgc agcacaagaa ggaccacccg gattacaagt accagccgcg gcggaggaag 540
tcggtgaaga acgggcaggc ggaggcagag gaggccacgg agcagacgca catctccccc 600
aacgccatct tcaaggcgct gcaggccgac tcgccacact cctcctccgg catgagcgag 660
gtgcactccc ccggcgagca ctcggggcaa tcccagggcc caccgacccc acccaccacc 720
cccaaaaccg acgtgcagcc gggcaaggct gacctgaagc gagaggggcg cccccttgcca 780 gaggggggca gacagccccc tatcgacttc cgcgacgtgg acatcggcga gctgagcagc 840
gacgtcatct ccaacatcga gaccttcgat gtcaacgagt ttgaccagta cctgccgccc 900
aacggccacc cgggggtgcc ggccacgcac ggccaggtca cctacacggg cagctacggc 960
atcagcagca ccgcggccac ccggcgagc gcgggccacg tgtggatgtc caagcagcag 1020
gcgccgccgc cacccccgca gcagccccca caggccccgc cggccccgca ggcgcccccg 1080
cagccgcagg cggcgccccc acagcagccg gcggcacccc cgcagcagcc acaggcgcac 1140
acgctgacca cgctgagcag cgagccgggc cagtcccagc gaacgcacat caagacggag 1200
cagctgagcc ccagccacta cagcgagcag cagcagcact cgccccaaca gatcgcctac 1260
agccccttca acctcccaca ctacagcccc tcctacccgc ccatcacccg ctcacagtac 1320
gactacaccg accaccagaa ctccagctcc tactacagcc acgcggcagg ccagggcacc 1380
ggcctctact ccaccttcac ctacatgaac cccgctcagc gccccatgta cacccccatc 1440
gccgacacct ctggggtccc ttccatcccg cagacccaca gcccccagca ctgggaacaa 1500
cccgtctaca cacagctcac tcgacct 1527

<210> SEQ ID NO 30
<211> LENGTH: 792
<212> TYPE: DNA
<213> ORGANISM: Homo sapiens

<400> SEQUENCE: 30
atggaagggt ttccccctcgt ccccccctcca tcagaagacc tggtgcccta tgacacggat 60
ctataccaac gccaaacgca cgagtattac ccctatctca gcagtgatgg ggagagccat 120
agcgaccatt actgggactt ccacccccac cacgtgcaca gcgagttcga gagcttcgcc 180
gagaacaact tcacggagct ccagagcgtg cagcccccgc agctgcagca gctctaccgc 240

```
cacatggagc tggagcagat gcacgtcctc gatacccccca tggtgccacc ccatcccagt    300

cttggccacc aggtctccta cctgccccgg atgtgcctcc agtacccatc cctgtcccca    360

gcccagccca gctcagatga ggaggagggc gagcggcaga gccccccact ggaggtgtct    420

gacggcgagg cggatggcct ggagcccggg cctgggctcc tgcctgggga gacaggcagc    480

aagaagaaga tccgcctgta ccagttcctg ttggacctgc tccgcagcgg cgacatgaag    540

gacagcatct ggtgggtgga caaggacaag ggcaccttcc agttctcgtc caagcacaag    600

gaggcgctgg cgcaccgctg gggcatccag aagggcaacc gcaagaagat gacctaccag    660

aagatggcgc gcgcgctgcg caactacggc aagacgggcg aggtcaagaa ggtgaagaag    720

aagctcacct accagttcag cggcgaagtg ctgggccgcg ggggcctggc cgagcggcgc    780

cacccgcccc ac                                                        792
```

<210> SEQ ID NO 31
<211> LENGTH: 708
<212> TYPE: DNA
<213> ORGANISM: Homo sapiens

<400> SEQUENCE: 31

```
atggaaagct ctgccaagat ggagagcggc ggcgccggcc agcagcccca gccgcagccc     60

cagcagccct tcctgccgcc cgcagcctgt ttctttgcca cggccgcagc cgcggcggcc    120

gcagccgccg cagcggcagc gcagagcgcg cagcagcagc agcagcagca gcagcagcag    180

cagcaggcgc cgcagctgag accggcggcc gacggccagc cctcaggggg cggtcacaag    240

tcagcgccca agcaagtcaa gcgacagcgc tcgtcttcgc ccgaactgat gcgctgcaaa    300

cgccggctca acttcagcgg ctttggctac agcctgccgc agcagcagcc ggccgccgtg    360

gcgcgccgca acgagcgcga gcgcaaccgc gtcaagttgg tcaacctggg ctttgccacc    420

cttcgggagc acgtccccaa cggcgcggcc aacaagaaga tgagtaaggt ggagacactg    480

cgctcggcgg tcgagtacat ccgcgcgctg cagcagctgc tggacgagca tgacgcggtg    540

agcgccgcct tccaggcagg cgtcctgtcg cccaccatct cccccaacta ctccaacgac    600

ttgaactcca tggccggctc gccggtctca tcctactcgt cggacgaggg ctcttacgac    660

ccgctcagcc ccgaggagca ggagcttctc gacttcacca actggttc                 708
```

<210> SEQ ID NO 32
<211> LENGTH: 2541
<212> TYPE: DNA
<213> ORGANISM: Homo sapiens

<400> SEQUENCE: 32

```
gggttggacc ctcgtacaga agctaatacg actcactata gggaaataag agagaaaaga     60

agagtaagaa gaaatataag agccaccccg cggtggcggc cgctctagaa ctagtggatc    120

ccccgggctg caggaattcg ataaaagcga tcgcccatca caagtttgta caaaaaagca    180

ggcttagcca ccatgtaccc atacgatgtt ccagattacg ctcctaagaa aaagaggaag    240

gtgcagagcg aggagatcca gggtcgtgag aagtcccggc ccgatcttgg cggggcctcc    300

aaggccaagc cacccacagc tccagcccct ccatcagctc ctgcaccttc tgcccagccc    360

acacccccgt cagcctctgt ccctggaaag aaggctcggg aggaagcccc agggccaccg    420

ggtgtcagcc gggccgacat gctgaagctg cgctcactta gtgaggggcc ccccaaggag    480

ctgaagatcc ggctcatcaa ggtagagagt ggtgacaagg agacctttat cgcctctgag    540

gtggaagagc ggcggctgcg catggcagac ctcaccatca gccactgtgc tgctgacgtc    600
```

```
gtgcgcgcca gcaggaatgc caaggtgaaa gggaagtttc gagagtccta cctttcccct    660

gcccagtctg tgaaaccgaa gatcaacact gaggagaagc tgccccggga aaaactcaac    720

ccccctacac ccagcatcta tctggagagc aaacgggatg ccttctcacc tgtcctgctg    780

cagttctgta cagaccctcg aaatcccatc acagtgatcc ggggcctggc gggctccctg    840

cggctcaact tgggcctctt ctccaccaag accctggtgg aagcgagtgg cgaacacacc    900

gtggaagttc gcacccaggt gcagcagccc tcagatgaga actgggatct gacaggcact    960

cggcagatct ggccttgtga gagctcccgt tcccacacca ccattgccaa gtacgcacag   1020

taccaggcct catccttcca ggagtctctg caggaggaga aggagagtga ggatgaggag   1080

tcagaggagc cagacagcac cactggaacc cctcctagca gcgcaccaga cccgaagaac   1140

catcacatca tcaagtttgg caccaacatc gacttgtctg atgctaagcg gtggaagccc   1200

cagctgcagg agctgctgaa gctgcccgcc ttcatgcggg taacatccac gggcaacatg   1260

ctgagccacg tgggccacac catcctgggc atgaacacgg tgcagctgta catgaaggtg   1320

cccggcagcc gaacgccagg ccaccaggag aataacaact tctgctccgt caacatcaac   1380

attggcccag gcgactgcga gtggttcgcg gtgcacgagc actactggga gaccatcagc   1440

gctttctgtg atcggcacgg cgtggactac ttgacgggtt cctggtggcc aatcctggat   1500

gatctctatg catccaatat tcctgtgtac cgcttcgtgc agcgacccgg agacctcgtg   1560

tggattaatg cggggactgt gcactgggtg caggccaccg gctggtgcaa caacattgcc   1620

tggaacgtgg ggcccctcac cgcctatcag taccagctgg ccctggaacg atacgagtgg   1680

aatgaggtga agaacgtcaa atccatcgtg cccatgattc acgtgtcatg gaacgtggct   1740

cgcacggtca aaatcagcga ccccgacttg ttcaagatga tcaagttctg cctgctgcag   1800

tccatgaagc actgccaggt gcaacgcgag agcctggtgc gggcagggaa gaaaatcgct   1860

taccagggcc gtgtcaagga cgagccagcc tactactgca acgagtgcga tgtggaggtg   1920

tttaacatcc tgttcgtgac aagtgagaat ggcagccgca acacgtacct ggtacactgc   1980

gagggctgtg cccggcgccg cagcgcaggc ctgcagggcg tggtggtgct ggagcagtac   2040

cgcactgagg agctggctca ggcctacgac gccttcacgc tggtgagggc ccggcgggcg   2100

cgcgggcagc ggaggagggc actggggcag gctgcaggga cgggcttcgg gagcccggcc   2160

gcgcctttcc ctgagccccc gccggctttc tccccccagg ccccagccag cacgtcgcga   2220

tgaacccagc tttcttgtac aaagtggtga tggccgctgt ttaaaacttt tatcaagctt   2280

atcgataccg tcgacctcga atgctgcctt ctgcggggct tgccttctgg ccatgccctt   2340

cttctctccc ttgcacctgt acctcttggt ctttgaataa agcctgagta ggaagtgagg   2400

gtctagaact agtgtcgacg caaaaaaaaa aaaaaaaaaa aaaaaaaaaa aaaaaaaaaa   2460

aaaaaaaaaa aaaaaaaaaa aaaaaaaaaa aaaaaaaaaa aaaaaaaaaa aaaaaaaaaa   2520

aaaaaaaaaa aaaaaaaaaa a                                             2541


<210> SEQ ID NO 33
<211> LENGTH: 1574
<212> TYPE: DNA
<213> ORGANISM: Homo sapiens

<400> SEQUENCE: 33

gggttggacc ctcgtacaga agctaatacg actcactata gggaaataag agagaaaaga     60

agagtaagaa gaaatataag agccaccccg cggtggcggc cgctctagaa ctagtggatc    120
```

```
ccccgggctg caggaattcg ataaaagcga tcgcccatca caagtttgta caaaaaagca    180

ggctccgcgg ccgcccccctt caccgctagg gataacaggg taatagaagg agccgccacc    240

atggagctac tgtcgccacc gctccgcgac gtagacctga cggcccccga cggctctctc    300

tgctcctttg ccacaacgga cgacttctat gacgacccgt gtttcgactc cccggacctg    360

cgcttcttcg aagacctgga cccgcgcctg atgcacgtgg gcgcgctcct gaaacccgaa    420

gagcactcgc acttccccgc ggcggtgcac ccggccccgg gcgcacgtga ggacgagcat    480

gtgcgcgcgc ccagcgggca ccaccaggcg ggccgctgcc tactgtgggc ctgcaaggcg    540

tgcaagcgca agaccaccaa cgccgaccgc cgcaaggccg ccaccatgcg cgagcggcgc    600

cgcctgagca aagtaaatga ggcctttgag acactcaagc gctgcacgtc gagcaatcca    660

aaccagcggt tgcccaaggt ggagatcctg cgcaacgcca tccgctatat cgagggcctg    720

caggctctgc tgcgcgacca ggacgccgcg ccccctggcg ccgcagccgc cttctatgcg    780

ccgggcccgc tgcccccggg ccgcggcggc gagcactaca gcggcgactc cgacgcgtcc    840

agcccgcgct ccaactgctc cgacggcatg atggactaca gcggcccccc gagcggcgcc    900

cggcggcgga actgctacga aggcgcctac tacaacgagg cgcccagcga acccaggccc    960

gggaagagtg cggcggtgtc gagcctagac tgcctgtcca gcatcgtgga gcgcatctcc   1020

accgagagcc ctgcggcgcc cgccctcctg ctggcggacg tgccttctga gtcgcctccg   1080

cgcaggcaag aggctgccgc cccagcgag ggagagagca gcggcgaccc cacccagtca    1140

ccggacgccg ccccgcagtg ccctgcgggt gcgaacccca acccgatata ccaggtgctc   1200

tgagtttcct gtgaacaatt gctcctctct taaggtagca aagggtgggc gcgccgaccc   1260

agctttcttg tacaaagtgg tgatggccgc tgtttaaaac ttttatcaag cttatcgata   1320

ccgtcgacct cgaatgctgc cttctgcggg gcttgccttc tggccatgcc cttcttctct   1380

cccttgcacc tgtacctctt ggtctttgaa taaagcctga gtaggaagtg agggtctaga   1440

actagtgtcg acgcaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaa                                                     1574


<210> SEQ ID NO 34
<211> LENGTH: 320
<212> TYPE: PRT
<213> ORGANISM: Homo sapiens

<400> SEQUENCE: 34

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110
```

```
Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
            180                 185                 190

Tyr Ser Gly Asp Ser Asp Ala Ser Ser Pro Arg Ser Asn Cys Ser Asp
        195                 200                 205

Gly Met Met Asp Tyr Ser Gly Pro Pro Ser Gly Ala Arg Arg Arg Asn
    210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
            260                 265                 270

Asp Val Pro Ser Glu Ser Pro Pro Arg Arg Gln Glu Ala Ala Ala Pro
        275                 280                 285

Ser Glu Gly Glu Ser Ser Gly Asp Pro Thr Gln Ser Pro Asp Ala Ala
    290                 295                 300

Pro Gln Cys Pro Ala Gly Ala Asn Pro Asn Pro Ile Tyr Gln Val Leu
305                 310                 315                 320


<210> SEQ ID NO 35
<211> LENGTH: 2414
<212> TYPE: DNA
<213> ORGANISM: Homo sapiens

<400> SEQUENCE: 35

gggttggacc ctcgtacaga agctaatacg actcactata gggaaataag agagaaaaga      60

agagtaagaa gaaatataag agccaccccg cggtggcggc cgctctagaa ctagtggatc     120

ccccgggctg caggaattcg ataaaagcga tcgcccatca caagtttgta caaaaaagca     180

ggctccacca tggtttctaa actgagccag ctgcagacgg agctcctggc ggccctgctg     240

gagtcagggc tgagcaaaga ggcactgctc caggcactgg gtgagccggg gccctacctc     300

ctggctggag aaggcccccct ggacaagggg gagtcctgcg gcggcggtcg aggggagctg     360

gctgagctgc ccaatgggct gggggagact cggggctccg aggacgagac ggacgacgat     420

ggggaagact tcacgccacc catcctcaaa gagctggaga acctcagccc tgaggaggcg     480

gcccaccaga aagccgtggt ggagaccctt ctgcaggagg acccgtggcg tgtggcgaag     540

atggtcaagt cctacctgca gcagcacaac atcccacagc gggaggtggt cgataccact     600

ggcctcaacc agtcccacct gtcccaacac ctcaacaagg gcactcccat gaagacgcag     660

aagcgggccg ccctgtacac ctggtacgtc cgcaagcagc gagaggtggc gcagcagttc     720

acccatgcag ggcagggagg gctgattgaa gagcccacag gtgatgagct accaaccaag     780

aaggggcgga ggaaccgttt caagtggggc ccagcatccc agcagatcct gttccaggcc     840

tatgagaggc agaagaaccc tagcaaggag gagcgagaga cgctagtgga ggagtgcaat     900

agggcggaat gcatccagag aggggtgtcc ccatcacagg cacaggggct gggctccaac     960
```

```
ctcgtcacgg aggtgcgtgt ctacaactgg tttgccaacc ggcgcaaaga agaagccttc   1020

cggcacaagc tggccatgga cacgtacagc gggccccccc cagggccagg cccgggacct   1080

gcgctgcccg ctcacagctc ccctggcctg cctccacctg ccctctcccc cagtaaggtc   1140

cacggtgtgc gctatggaca gcctgcgacc agtgagactg cagaagtacc ctcaagcagc   1200

ggcggtccct tagtgacagt gtctacaccc ctccaccaag tgtcccccac gggcctggag   1260

cccagccaca gcctgctgag tacagaagcc aagctggtct cagcagctgg gggccccctc   1320

ccccctgtca gcaccctgac agcactgcac agcttggagc agacatcccc aggcctcaac   1380

cagcagcccc agaacctcat catggcctca cttcctgggg tcatgaccat cgggcctggt   1440

gagcctgcct ccctgggtcc tacgttcacc aacacaggtg cctccaccct ggtcatcggc   1500

ctggcctcca cgcaggcaca gagtgtgccg gtcatcaaca gcatgggcag cagcctgacc   1560

accctgcagc ccgtccagtt ctcccagccg ctgcacccct cctaccagca gccgctcatg   1620

ccacctgtgc agagccatgt gacccagagc cccttcatgg ccaccatggc tcagctgcag   1680

agcccccacg ccctctacag ccacaagccc gaggtggccc agtacaccca cacaggcctg   1740

ctcccgcaga ctatgctcat caccgacacc accaacctga gcgccctggc cagcctcacg   1800

cccaccaagc aggtcttcac ctcagacact gaggcctcca gtgagtccgg gcttcacacg   1860

ccggcatctc aggccaccac cctccacgtc cccagccagg accctgccgg catccagcac   1920

ctgcagccgg cccaccggct cagcgccagc cccacagtgt cctccagcag cctggtgctg   1980

taccagagct cagactccag caatggccag agccacctgc tgccatccaa ccacagcgtc   2040

atcgagacct tcatctccac ccagatggcc tcttcctccc agttgtgagc ggccgcaccc   2100

agctttcttg tacaaagtgg tgatggccgc tgtttaaaac ttttatcaag cttatcgata   2160

ccgtcgacct cgaatgctgc cttctgcggg gcttgccttc tggccatgcc cttcttctct   2220

cccttgcacc tgtacctctt ggtctttgaa taaagcctga gtaggaagtg agggtctaga   2280

actagtgtcg acgcaaaaaa aaaaaaaaaa aaaaaaaaaa aaaaaaaaaa aaaaaaaaaa   2340

aaaaaaaaaa aaaaaaaaaa aaaaaaaaaa aaaaaaaaaa aaaaaaaaaa aaaaaaaaaa   2400

aaaaaaaaaa aaaa                                                     2414
```

<210> SEQ ID NO 36
<211> LENGTH: 632
<212> TYPE: PRT
<213> ORGANISM: Homo sapiens

<400> SEQUENCE: 36

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Leu Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110
```

```
Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
```

```
    530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln Leu
625                 630
```

<210> SEQ ID NO 37
<211> LENGTH: 1222
<212> TYPE: DNA
<213> ORGANISM: Homo sapiens

<400> SEQUENCE: 37

```
gggttggacc ctcgtacaga agctaatacg actcactata gggaaataag agagaaaaga     60

agagtaagaa gaaatataag agccaccccg cggtggcggc cgctctagaa ctagtggatc    120

ccccgggctg caggaattcg ataaaagcga tcgcccatca caagtttgta caaaaaagca    180

ggctccacca tgccagcccg ccttgagacc tgcatctccg acctcgactg cgccagcagc    240

agcggcagtg acctatccgg cttcctcacc gacgaggaag actgtgccag actccaacag    300

gcagcctccg cttcggggcc gcccgcgccg gcccgcaggg gcgcgcccaa tatctcccgg    360

gcgtctgagg ttccaggggc acaggacgac gagcaggaga ggcggcggcg ccgcggccgg    420

acgcgggtcc gctccgaggc gctgctgcac tcgctgcgca ggagccggcg cgtcaaggcc    480

aacgatcgcg agcgcaaccg catgcacaac ttgaacgcgg ccctggacgc actgcgcagc    540

gtgctgccct cgttccccga cgacaccaag ctcaccaaaa tcgagacgct gcgcttcgcc    600

tacaactaca tctgggctct ggccgagaca ctgcgcctgg cggatcaagg gctgcccgga    660

ggcggtgccc gggagcgcct cctgccgccg cagtgcgtcc cctgcctgcc cggtccccca    720

agccccgcca gcgacgcgga gtcctggggc tcaggtgccg ccgccgcctc cccgctctct    780

gaccccagta gcccagccgc ctccgaagac ttcacctacc gccccggcga ccctgttttc    840

tccttcccaa gcctgcccaa agacttgctc cacacaacgc cctgtttcat tccttaccac    900

taggacccag ctttcttgta caaagtggtg atggccgctg tttaaaactt ttatcaagct    960

tatcgatacc gtcgacctcg aatgctgcct tctgcggggc ttgccttctg gccatgccct   1020

tcttctctcc cttgcacctg tacctcttgg tctttgaata aagcctgagt aggaagtgag   1080

ggtctagaac tagtgtcgac gcaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aa                                             1222
```

<210> SEQ ID NO 38
<211> LENGTH: 237
<212> TYPE: PRT
<213> ORGANISM: Homo sapiens

<400> SEQUENCE: 38

```
Met Pro Ala Arg Leu Glu Thr Cys Ile Ser Asp Leu Asp Cys Ala Ser
```

```
1               5                   10                  15

Ser Ser Gly Ser Asp Leu Ser Gly Phe Leu Thr Asp Glu Glu Asp Cys
            20                  25                  30

Ala Arg Leu Gln Gln Ala Ala Ser Ala Ser Gly Pro Pro Ala Pro Ala
        35                  40                  45

Arg Arg Gly Ala Pro Asn Ile Ser Arg Ala Ser Glu Val Pro Gly Ala
    50                  55                  60

Gln Asp Asp Glu Gln Glu Arg Arg Arg Arg Arg Gly Arg Thr Arg Val
65                  70                  75                  80

Arg Ser Glu Ala Leu Leu His Ser Leu Arg Arg Ser Arg Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Asp Thr Lys Leu
        115                 120                 125

Thr Lys Ile Glu Thr Leu Arg Phe Ala Tyr Asn Tyr Ile Trp Ala Leu
    130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235
```

<210> SEQ ID NO 39
<211> LENGTH: 1357
<212> TYPE: DNA
<213> ORGANISM: Homo sapiens

<400> SEQUENCE: 39

```
gggttggacc ctcgtacaga agctaatacg actcactata gggaaataag agagaaaaga     60

agagtaagaa gaaatataag agccaccccg cggtggcggc cgctctagaa ctagtggatc    120

ccccgggctg caggaattcg ataaaagcga tcgcccatca caagtttgta caaaaaagca    180

ggctccgcgg ccgccccctt caccatgttc gtcaaatccg agaccttgga gttgaaggag    240

gaagaggacg tgttagtgct gctcggatcg gcctccccg ccttggcggc cctgaccccg     300

ctgtcatcca gcgccgacga agaagaggag gaggagccgg gcgcgtcagg tggggcgcgt    360

cggcagcgcg gggctgaggc cgggcagggg gcgcggggcg gcgtggctgc gggtgcggag    420

ggctgccggc ccgcacggct gctgggtctg gtacacgatt gcaaacggcg cccttcccgg    480

gcgcgggccg tctcccgagg cgccaagacg gccgagacgg tgcagcgcat caagaagacc    540

cgtagactga aggccaacaa ccgcgagcga aaccgcatgc acaacctcaa cgcggcactg    600

gacgcgctgc gcgaggtgct ccccacgttc cccgaggacg ccaagctcac caagatcgag    660

accctgcgct tcgcccacaa ctacatctgg gcactcaccg agaccctgcg cctggcggat    720

cactgcgggg gcggcggcgg gggcctgccg ggggcgctct tctccgaggc agtgttgctg    780

agcccgggag gcgccagcgc cgccctgagc agcagcggag acagccccctc gcccgcctcc    840
```

```
acgtggagtt gcaccaacag ccccgcgccg tcctcctccg tgtcctccaa ttccacctcc    900

ccctacagct gcactttatc gcccgccagc ccggccgggt cagacatgga ctattggcag    960

cccccacctc ccgacaagca ccgctatgca cctcacctcc ccatagccag ggattgtatc   1020

tagaagggtg ggcgcgccga cccagctttc ttgtacaaag tggtgatggc cgctgtttaa   1080

aacttttatc aagcttatcg ataccgtcga cctcgaatgc tgccttctgc ggggcttgcc   1140

ttctggccat gcccttcttc tctcccttgc acctgtacct cttggtcttt gaataaagcc   1200

tgagtaggaa gtgagggtct agaactagtg tcgacgcaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaa                            1357


<210> SEQ ID NO 40
<211> LENGTH: 272
<212> TYPE: PRT
<213> ORGANISM: Homo sapiens

<400> SEQUENCE: 40

Met Phe Val Lys Ser Glu Thr Leu Glu Leu Lys Glu Glu Glu Asp Val
1               5                   10                  15

Leu Val Leu Leu Gly Ser Ala Ser Pro Ala Leu Ala Ala Leu Thr Pro
            20                  25                  30

Leu Ser Ser Ser Ala Asp Glu Glu Glu Glu Glu Glu Pro Gly Ala Ser
        35                  40                  45

Gly Gly Ala Arg Arg Gln Arg Gly Ala Glu Ala Gly Gln Gly Ala Arg
    50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Gly Gly
                165                 170                 175

Gly Gly Gly Gly Leu Pro Gly Ala Leu Phe Ser Glu Ala Val Leu Leu
            180                 185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
    210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro Pro
                245                 250                 255

Asp Lys His Arg Tyr Ala Pro His Leu Pro Ile Ala Arg Asp Cys Ile
            260                 265                 270
```

<210> SEQ ID NO 41
<211> LENGTH: 1153
<212> TYPE: DNA
<213> ORGANISM: Homo sapiens

<400> SEQUENCE: 41
gggttggacc ctcgtacaga agctaatacg actcactata gggaaataag agagaaaaga 60
agagtaagaa gaaatataag agccaccccg cggtggcggc cgctctagaa ctagtggatc 120
ccccgggctg caggaattcg ataaaagcga tcgcccatca caagtttgta caaaaaagca 180
ggcttcacca tgacgcctca accctcgggt gcgcccactg tccaagtgac ccgtgagacg 240
gagcggtcct tccccagagc ctcggaagac gaagtgacct gccccacgtc cgccccgccc 300
agccccactc gcacacgggg gaactgcgca gaggcggaag agggaggctg ccgaggggcc 360
ccgaggaagc tccgggcacg gcgcggggga cgcagccggc ctaagagcga gttggcactg 420
agcaagcagc gacggagtcg gcgaaagaag gccaacgacc gcgagcgcaa tcgaatgcac 480
aacctcaact cggcactgga cgccctgcgc ggtgtcctgc ccaccttccc agacgacgcg 540
aagctcacca agatcgagac gctgcgcttc gcccacaact acatctgggc gctgactcaa 600
acgctgcgca tagcggacca cagcttgtac gcgctggagc cgccggcgcc gcactgcggg 660
gagctgggca gcccaggcgg ttcccccggg gactgggggt ccctctactc cccagtctcc 720
caggctggca gcctgagtcc cgccgcgtcg ctggaggagc gacccgggct gctgggggcc 780 acctttccg cctgcttgag cccaggcagt ctggctttct cagattttct gtgagaccca 840
gctttcttgt acaaagtggt gatggccgct gtttaaaact tttatcaagc ttatcgatac 900
cgtcgacctc gaatgctgcc ttctgcgggg cttgccttct ggccatgccc ttcttctctc 960
ccttgcacct gtacctcttg gtctttgaat aaagcctgag taggaagtga gggtctagaa 1020
ctagtgtcga cgcaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaa 1153

<210> SEQ ID NO 42
<211> LENGTH: 214
<212> TYPE: PRT
<213> ORGANISM: Homo sapiens

<400> SEQUENCE: 42

Met Thr Pro Gln Pro Ser Gly Ala Pro Thr Val Gln Val Thr Arg Glu
1 5 10 15

Thr Glu Arg Ser Phe Pro Arg Ala Ser Glu Asp Glu Val Thr Cys Pro
20 25 30

Thr Ser Ala Pro Pro Ser Pro Thr Arg Thr Arg Gly Asn Cys Ala Glu
35 40 45

Ala Glu Glu Gly Gly Cys Arg Gly Ala Pro Arg Lys Leu Arg Ala Arg
50 55 60

Arg Gly Gly Arg Ser Arg Pro Lys Ser Glu Leu Ala Leu Ser Lys Gln
65 70 75 80

Arg Arg Ser Arg Arg Lys Lys Ala Asn Asp Arg Glu Arg Asn Arg Met
85 90 95

His Asn Leu Asn Ser Ala Leu Asp Ala Leu Arg Gly Val Leu Pro Thr
100 105 110

Phe Pro Asp Asp Ala Lys Leu Thr Lys Ile Glu Thr Leu Arg Phe Ala
115 120 125

```
His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Phe Ser Ala Cys Leu Ser Pro Gly Ser Leu
        195                 200                 205

Ala Phe Ser Asp Phe Leu
    210


<210> SEQ ID NO 43
<211> LENGTH: 1609
<212> TYPE: DNA
<213> ORGANISM: Homo sapiens

<400> SEQUENCE: 43

gggttggacc ctcgtacaga agctaatacg actcactata gggaaataag agagaaaaga     60

agagtaagaa gaaatataag agccaccccg cggtggcggc cgctctagaa ctagtggatc    120

ccccgggctg caggaattcg ataaaagcga tcgcccatca caagtttgta caaaaaagca    180

ggctccgcgg ccgccccctt caccatgacc aaatcgtaca gcgagagtgg gctgatgggc    240

gagcctcagc cccaaggtcc tccaagctgg acagacgagt gtctcagttc tcaggacgag    300

gagcacgagg cagacaagaa ggaggacgac ctcgaagcca tgaacgcaga ggaggactca    360

ctgaggaacg gggagagga ggaggacgaa gatgaggacc tggaagagga ggaagaagag    420

gaagaggagg atgacgatca aaagcccaag agacgcggcc ccaaaaagaa gaagatgact    480

aaggctcgcc tggagcgttt taaattgaga cgcatgaagg ctaacgcccg ggagcggaac    540

cgcatgcacg gactgaacgc ggcgctagac aacctgcgca aggtggtgcc ttgctattct    600

aagacgcaga agctgtccaa aatcgagact ctgcgcttgg ccaagaacta catctgggct    660

ctgtcggaga tcctgcgctc aggcaaaagc ccagacctgg tctccttcgt tcagacgctt    720

tgcaagggct tatcccaacc caccaccaac ctggttgcgg gctgcctgca actcaatcct    780

cggacttttc tgcctgagca gaaccaggac atgccccccc acctgccgac ggccagcgct    840

tccttccctg tacaccccta ctcctaccag tcgcctgggc tgcccagtcc gccttacggt    900

accatggaca gctcccatgt cttccacgtt aagcctccgc cgcacgccta cagcgcagcg    960

ctggagccct tctttgaaag ccctctgact gattgcacca gcccttcctt tgatggaccc   1020

ctcagcccgc cgctcagcat caatggcaac ttctctttca aacacgaacc gtccgccgag   1080

tttgagaaaa attatgcctt taccatgcac tatcctgcag cgacactggc aggggcccaa   1140

agccacggat caatcttctc aggcaccgct gcccctcgct gcgagatccc catagacaat   1200

attatgtcct tcgatagcca ttcacatcat gagcgagtca tgagtgccca gctcaatgcc   1260

atatttcatg attagaaggg tgggcgcgcc gacccagctt tcttgtacaa agtggtgatg   1320

gccgctgttt aaaactttta tcaagcttat cgataccgtc gacctcgaat gctgccttct   1380

gcggggcttg ccttctggcc atgcccttct tctctccctt gcacctgtac ctcttggtct   1440

ttgaataaag cctgagtagg aagtgagggt ctagaactag tgtcgacgca aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaa               1609
```

```
<210> SEQ ID NO 44
<211> LENGTH: 356
<212> TYPE: PRT
<213> ORGANISM: Homo sapiens

<400> SEQUENCE: 44

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355
```

<210> SEQ ID NO 45
<211> LENGTH: 1687
<212> TYPE: DNA
<213> ORGANISM: Homo sapiens

<400> SEQUENCE: 45

```
gggttggacc ctcgtacaga agctaatacg actcactata gggaaataag agagaaaaga     60
agagtaagaa gaaatataag agccaccccg cggtggcggc cgctctagaa ctagtggatc    120
ccccgggctg caggaattcg ataaaagcga tcgcccatca caagtttgta caaaaaagca    180
ggctccgcgg ccgccccctt caccatgctg acccgcctgt tcagcgagcc cggccttctc    240
tcggacgtgc ccaagttcgc cagctggggc gacggcgaag acgacgagcc gaggagcgac    300
aagggcgacg cgccgccacc gccaccgcct gcgcccgggc caggggctcc ggggccagcc    360
cgggcggcca agccagtccc tctccgtgga gaagagggga cggaggccac gttggccgag    420
gtcaaggagg aaggcgagct gggggggagag gaggaggagg aagaggagga ggaagaagga    480
ctggacgagg cggagggcga gcggcccaag aagggcgggc ccaagaagcg caagatgacc    540
aaggcgcgct tggagcgctc caagcttcgg cggcagaagg cgaacgcgcg ggagcgcaac    600
cgcatgcacg acctgaacgc agccctggac aacctgcgca aggtggtgcc ctgctactcc    660
aagacgcaga agctgtccaa gatcgagacg ctgcgcctag ccaagaacta tatctgggcg    720
ctctcggaga tcctgcgctc cggcaagcgg ccagacctag tgtcctacgt gcagactctg    780
tgcaagggtc tgtcgcagcc caccaccaat ctggtggccg gctgtctgca gctcaactct    840
cgcaacttcc tcacggagca aggcgccgac ggtgccggcc gcttccacgg ctcgggcggc    900
ccgttcgcca tgcaccccta cccgtacccg tgctcgcgcc tggcgggcgc acagtgccag    960
gcggccggcg gcctgggcgg cggcgcggcg cacgccctgc ggacccacgg ctactgcgca   1020
gcctacgaga cgctgtatgc ggcggcaggc ggtggcggcg cgagcccgga ctacaacagc   1080
tccgagtacg agggcccgct cagccccccg ctctgtctca atggcaactt ctcactcaag   1140
caggactcct cgcccgacca cgagaaaagc taccactact ctatgcacta ctcggcgctg   1200
cccggttcgc ggcccacggg ccacgggcta gtcttcggct cgtcggctgt gcgcgggggc   1260
gtccactcgg agaatctctt gtcttacgat atgcaccttc accacgaccg gggccccatg   1320
tacgaggagc tcaatgcgtt ttttcataac tgaaagggtg ggcgcgccga cccagctttc   1380
ttgtacaaag tggtgatggc cgctgtttaa aacttttatc aagcttatcg ataccgtcga   1440
cctcgaatgc tgccttctgc ggggcttgcc ttctggccat gcccttcttc tctcccttgc   1500
acctgtacct cttggtcttt gaataaagcc tgagtaggaa gtgagggtct agaactagtg   1560
tcgacgcaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaa                                                             1687
```

<210> SEQ ID NO 46
<211> LENGTH: 382
<212> TYPE: PRT
<213> ORGANISM: Homo sapiens

<400> SEQUENCE: 46

```
Met Leu Thr Arg Leu Phe Ser Glu Pro Gly Leu Leu Ser Asp Val Pro
1               5                   10                  15

Lys Phe Ala Ser Trp Gly Asp Gly Glu Asp Asp Glu Pro Arg Ser Asp
            20                  25                  30
```

-continued

```
Lys Gly Asp Ala Pro Pro Pro Pro Pro Pro Ala Pro Gly Pro Gly Ala
        35                  40                  45

Pro Gly Pro Ala Arg Ala Ala Lys Pro Val Pro Leu Arg Gly Glu Glu
    50                  55                  60

Gly Thr Glu Ala Thr Leu Ala Glu Val Lys Glu Glu Gly Glu Leu Gly
65                  70                  75                  80

Gly Glu Glu Glu Glu Glu Glu Glu Glu Glu Glu Gly Leu Asp Glu Ala
                85                  90                  95

Glu Gly Glu Arg Pro Lys Lys Gly Gly Pro Lys Lys Arg Lys Met Thr
            100                 105                 110

Lys Ala Arg Leu Glu Arg Ser Lys Leu Arg Arg Gln Lys Ala Asn Ala
        115                 120                 125

Arg Glu Arg Asn Arg Met His Asp Leu Asn Ala Ala Leu Asp Asn Leu
    130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
            180                 185                 190

Cys Lys Gly Leu Ser Gln Pro Thr Thr Asn Leu Val Ala Gly Cys Leu
        195                 200                 205

Gln Leu Asn Ser Arg Asn Phe Leu Thr Glu Gln Gly Ala Asp Gly Ala
    210                 215                 220

Gly Arg Phe His Gly Ser Gly Gly Pro Phe Ala Met His Pro Tyr Pro
225                 230                 235                 240

Tyr Pro Cys Ser Arg Leu Ala Gly Ala Gln Cys Gln Ala Ala Gly Gly
                245                 250                 255

Leu Gly Gly Gly Ala Ala His Ala Leu Arg Thr His Gly Tyr Cys Ala
            260                 265                 270

Ala Tyr Glu Thr Leu Tyr Ala Ala Ala Gly Gly Gly Gly Ala Ser Pro
        275                 280                 285

Asp Tyr Asn Ser Ser Glu Tyr Glu Gly Pro Leu Ser Pro Pro Leu Cys
    290                 295                 300

Leu Asn Gly Asn Phe Ser Leu Lys Gln Asp Ser Ser Pro Asp His Glu
305                 310                 315                 320

Lys Ser Tyr His Tyr Ser Met His Tyr Ser Ala Leu Pro Gly Ser Arg
                325                 330                 335

Pro Thr Gly His Gly Leu Val Phe Gly Ser Ser Ala Val Arg Gly Gly
            340                 345                 350

Val His Ser Glu Asn Leu Leu Ser Tyr Asp Met His Leu His His Asp
        355                 360                 365

Arg Gly Pro Met Tyr Glu Glu Leu Asn Ala Phe Phe His Asn
    370                 375                 380
```